(12) United States Patent
Gephart

(10) Patent No.: US 9,265,543 B2
(45) Date of Patent: Feb. 23, 2016

(54) BONE PLATE SYSTEM AND METHOD

(71) Applicant: Pioneer Surgical Technology, Inc., Marquette, MI (US)

(72) Inventor: Matthew P. Gephart, Marquette, MI (US)

(73) Assignee: PIONEER SURGICAL TECHNOLOGY, INC., Marquette, MI (US)

( * ) Notice: Subject to any disclaimer, the term of this patent is extended or adjusted under 35 U.S.C. 154(b) by 398 days.

(21) Appl. No.: 13/728,878

(22) Filed: Dec. 27, 2012

(65) Prior Publication Data

US 2013/0165933 A1 Jun. 27, 2013

Related U.S. Application Data

(60) Provisional application No. 61/580,560, filed on Dec. 27, 2011, provisional application No. 61/710,354, filed on Oct. 5, 2012.

(51) Int. Cl.
*A61B 17/80* (2006.01)
*A61B 17/82* (2006.01)
*A61B 17/84* (2006.01)

(52) U.S. Cl.
CPC .......... *A61B 17/8076* (2013.01); *A61B 17/809* (2013.01); *A61B 17/8052* (2013.01); *A61B 17/823* (2013.01); *A61B 17/842* (2013.01)

(58) Field of Classification Search
CPC ............. A61B 17/8076; A61B 17/823; A61B 17/842; A61B 17/683; A61B 17/72; A61B 17/86
See application file for complete search history.

(56) References Cited

U.S. PATENT DOCUMENTS

| 4,050,464 A | 9/1977 | Hall |
| 4,269,180 A | 5/1981 | Dall |
| 4,327,715 A | 5/1982 | Corvisier |

(Continued)

FOREIGN PATENT DOCUMENTS

| AU | 743254 | 1/2002 |
| TW | 314764 | 9/1997 |

(Continued)

OTHER PUBLICATIONS

Acute Innovation—Quick and Easy Installation & Re-entry, Acute Innovation, LLC, htto://www.acuteinnovations.com/oroducts/AcuTie/Installtion, May 16, 2012, 7 pages.

(Continued)

*Primary Examiner* — Samuel Hanna
(74) *Attorney, Agent, or Firm* — Fitch, Even, Tabin & Flannery LLP

(57) ABSTRACT

In one aspect, a bone plate system is provided including a bone plate and a plurality of cable connector devices configured to be inserted into throughbores formed in bone portions and through openings of the bone plate member aligned therewith. The cable connector devices each include opposite end portions with one end portion configured to abut against the bone adjacent the throughbore and the other end portion configured to be operatively fixed to the bone plate member with the cable portion extending therebetween and in the bone throughbore for securing the bone plate member to the bone portion with the cable connector devices including a cable portion thereof extending in the bone throughbore.

14 Claims, 77 Drawing Sheets

(56) References Cited

U.S. PATENT DOCUMENTS

| | | | |
|---|---|---|---|
| 4,583,541 A | 4/1986 | Barry | |
| 4,959,065 A | 9/1990 | Arnett | |
| 5,015,248 A | 5/1991 | Burstein et al. | |
| 5,139,498 A | 8/1992 | Astudillo | |
| 5,312,410 A | 5/1994 | Miller | |
| 5,395,374 A | 3/1995 | Miller | |
| 5,415,658 A | 5/1995 | Kilpela et al. | |
| 5,449,361 A | 9/1995 | Preissman | |
| 5,456,722 A | 10/1995 | McLeod | |
| 5,536,270 A | 7/1996 | Songer | |
| 5,568,865 A | 10/1996 | Mase | |
| 5,569,253 A | 10/1996 | Farris | |
| 5,660,091 A | 8/1997 | Stone | |
| 5,702,399 A | 12/1997 | Kilpela | |
| 5,752,959 A | 5/1998 | Korhonen | |
| 5,810,825 A | 9/1998 | Huebner | |
| 5,849,012 A | 12/1998 | Abboudi | |
| 5,902,305 A | 5/1999 | Beger | |
| 5,935,133 A | 8/1999 | Wagner | |
| 6,017,347 A | 1/2000 | Huebner | |
| 6,077,268 A | 6/2000 | Farris | |
| 6,086,590 A | 7/2000 | Margulies | |
| 6,099,527 A | 8/2000 | Hochschuler | |
| 6,120,506 A | 9/2000 | Kohrs | |
| 6,123,709 A | 9/2000 | Jones | |
| 6,277,120 B1 * | 8/2001 | Lawson | 606/263 |
| 6,387,099 B1 | 5/2002 | Lange | |
| 6,398,787 B1 | 6/2002 | Itoman | |
| 6,454,770 B1 | 9/2002 | Klaue | |
| 6,475,220 B1 | 11/2002 | Whiteside | |
| 6,520,965 B2 * | 2/2003 | Chervitz | A61B 17/842 606/103 |
| 6,605,091 B1 | 8/2003 | Iwanski | |
| 6,629,975 B1 | 10/2003 | Kilpela | |
| 6,730,091 B1 | 5/2004 | Pfefferle | |
| 6,832,532 B2 | 12/2004 | Kilpela | |
| 6,872,210 B2 | 3/2005 | Hearn | |
| 7,052,499 B2 | 5/2006 | Steger | |
| 7,156,847 B2 | 1/2007 | Abramson | |
| 7,207,993 B1 | 4/2007 | Baldwin | |
| 7,229,444 B2 | 6/2007 | Boyd | |
| 7,250,054 B2 * | 7/2007 | Allen | A61B 17/82 606/103 |
| 7,635,365 B2 | 12/2009 | Ellis et al. | |
| 7,695,501 B2 | 4/2010 | Ellis et al. | |
| 7,785,355 B2 | 8/2010 | Mohr et al. | |
| 7,803,176 B2 | 9/2010 | Teague | |
| 8,282,675 B2 | 10/2012 | Maguire | |
| 8,298,247 B2 | 10/2012 | Sterrett | |
| 8,313,517 B2 | 11/2012 | Mohr et al. | |
| 8,337,497 B2 | 12/2012 | Deslauriers | |
| 8,372,123 B2 | 2/2013 | Smisson, III | |
| 8,460,295 B2 | 6/2013 | McClellan | |
| 8,460,345 B2 | 6/2013 | Steger | |
| 2002/0072753 A1 | 6/2002 | Cohen | |
| 2004/0199169 A1 | 10/2004 | Koons | |
| 2005/0171547 A1 | 8/2005 | Aram | |
| 2005/0177179 A1 | 8/2005 | Baynham | |
| 2006/0089646 A1 | 4/2006 | Bonutti | |
| 2006/0167464 A1 | 7/2006 | Allen | |
| 2007/0225715 A1 * | 9/2007 | Deffenbaugh | A61B 17/683 606/304 |
| 2008/0195145 A1 | 8/2008 | Bonutti | |
| 2008/0287951 A1 | 11/2008 | Stoneburner | |
| 2009/0069812 A1 | 3/2009 | Gillard et al. | |
| 2009/0069851 A1 | 3/2009 | Gillard | |
| 2009/0105717 A1 | 4/2009 | Bluechel | |
| 2009/0171402 A1 | 7/2009 | DellOca | |
| 2010/0042106 A1 | 2/2010 | Bryant | |
| 2010/0057091 A1 | 3/2010 | Oosterom | |
| 2010/0094294 A1 | 4/2010 | Gillard | |
| 2010/0179595 A1 | 7/2010 | Jackson | |
| 2010/0305571 A1 | 12/2010 | Pratt | |
| 2010/0318137 A1 | 12/2010 | Stucki | |
| 2010/0331844 A1 | 12/2010 | Ellis et al. | |
| 2010/0331892 A1 | 12/2010 | Fell et al. | |
| 2011/0218580 A1 | 9/2011 | Schwager | |
| 2012/0089193 A1 | 4/2012 | Stone | |
| 2012/0215224 A1 | 8/2012 | Songer | |
| 2012/0226321 A1 | 9/2012 | Gonzalez-Hernandez | |
| 2012/0303065 A1 * | 11/2012 | Larroque-Lahitette et al. | 606/277 |
| 2013/0167334 A1 | 7/2013 | Gephart | |
| 2013/0289564 A1 | 10/2013 | Bernstein | |
| 2014/0142638 A1 | 5/2014 | Goodwin et al. | |

FOREIGN PATENT DOCUMENTS

| | | |
|---|---|---|
| WO | 9428812 | 12/1994 |
| WO | 0149191 | 7/2001 |
| WO | 0234120 | 5/2002 |
| WO | 2006088452 | 8/2006 |
| WO | 2011041624 | 4/2011 |
| WO | 2011116364 | 9/2011 |
| WO | 2013003719 | 1/2013 |

OTHER PUBLICATIONS

Ease of Wire with the Stability of a Plate, AcuTie Sternal Closure System, Oct. 2010, 12 pages.

Re-Entry Options, AcuTie Sternal Closure System, accessed May 16, 2012, 1 page.

SternaLock Blu Primary Closure System, Biomet Microfixation, Form No. BMF00-3265, Rev 05k1110, 2011, 10 pages.

Technique Guide, Modular Sternal Cable System Flexibility and Strength in Sternal Closure and Repair, Synthes CMF, Jul. 2008, 39 pages.

Technique Guide, Titanium Sternal Fixation System for Stable Internal Fixation of the Sternum, Synthes, Inc., Oct. 2010, 36 pages.

* cited by examiner

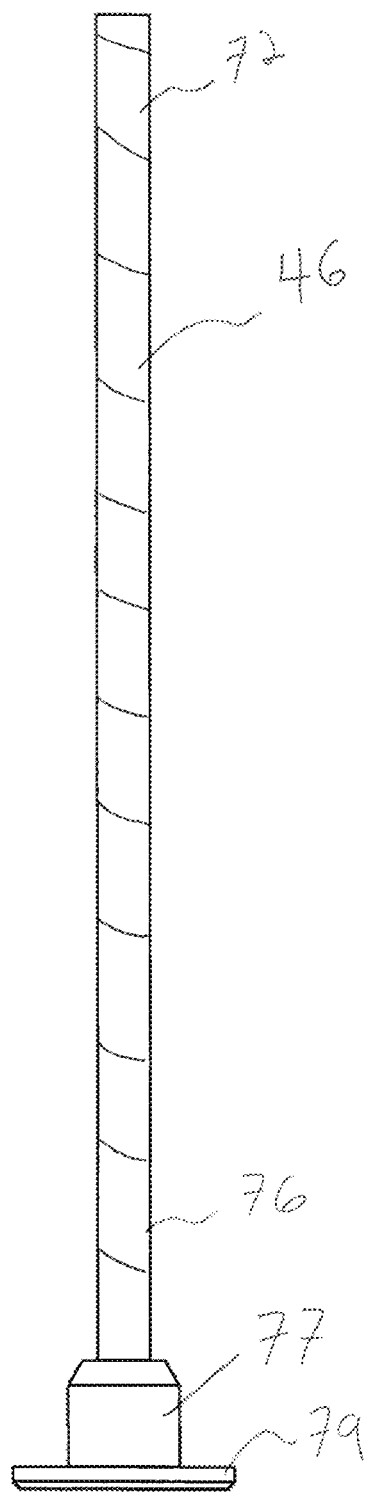

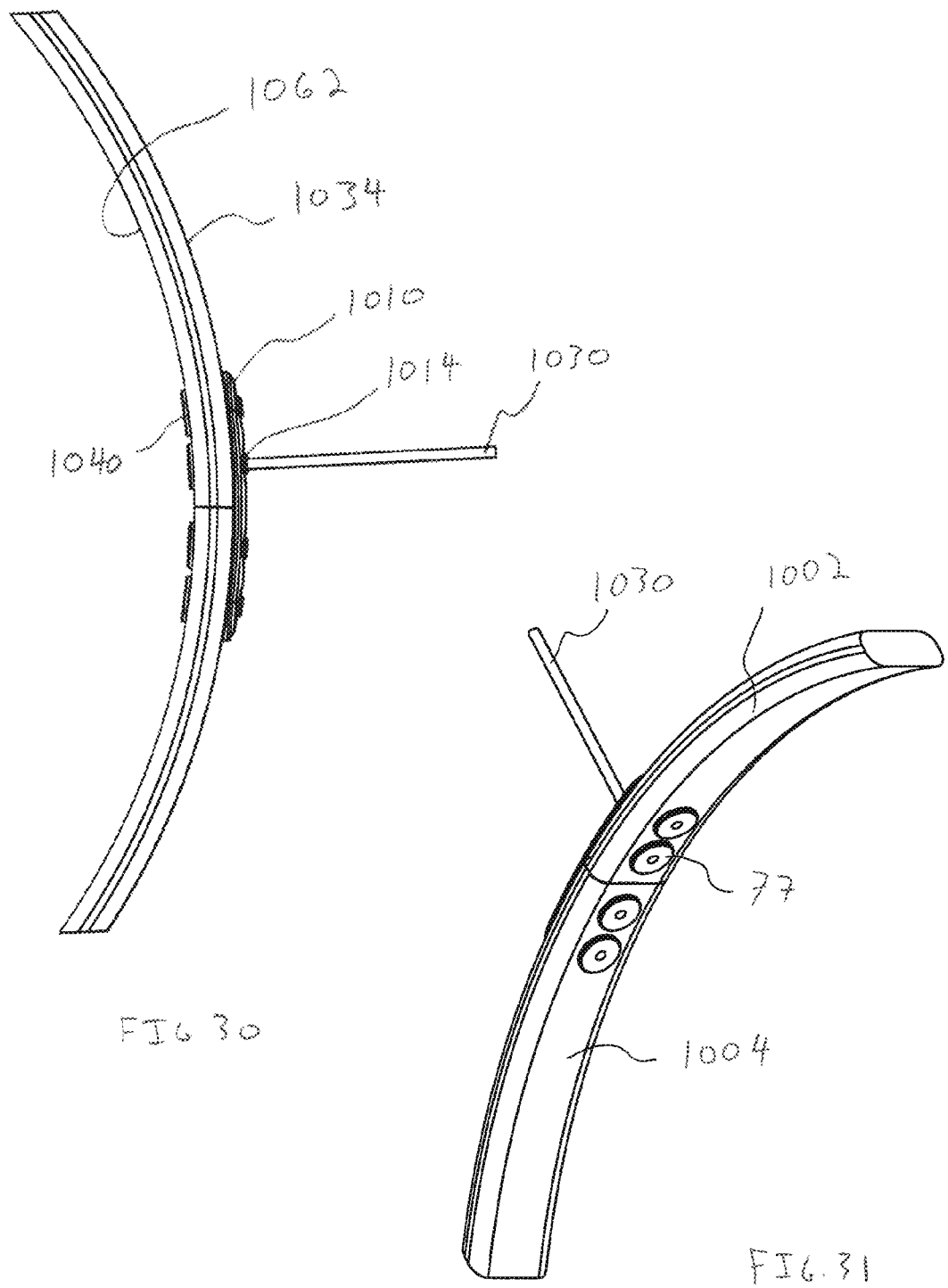

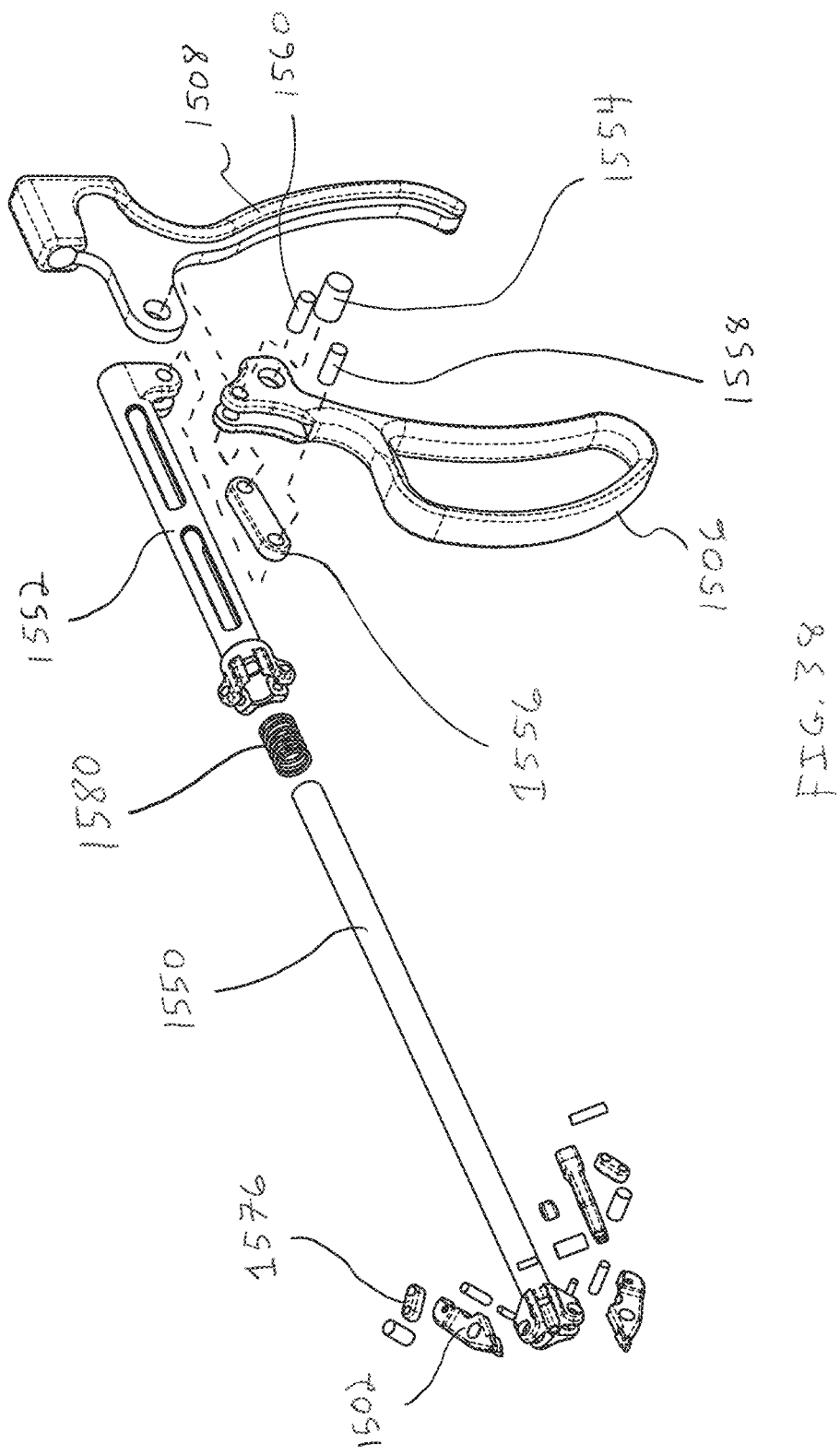

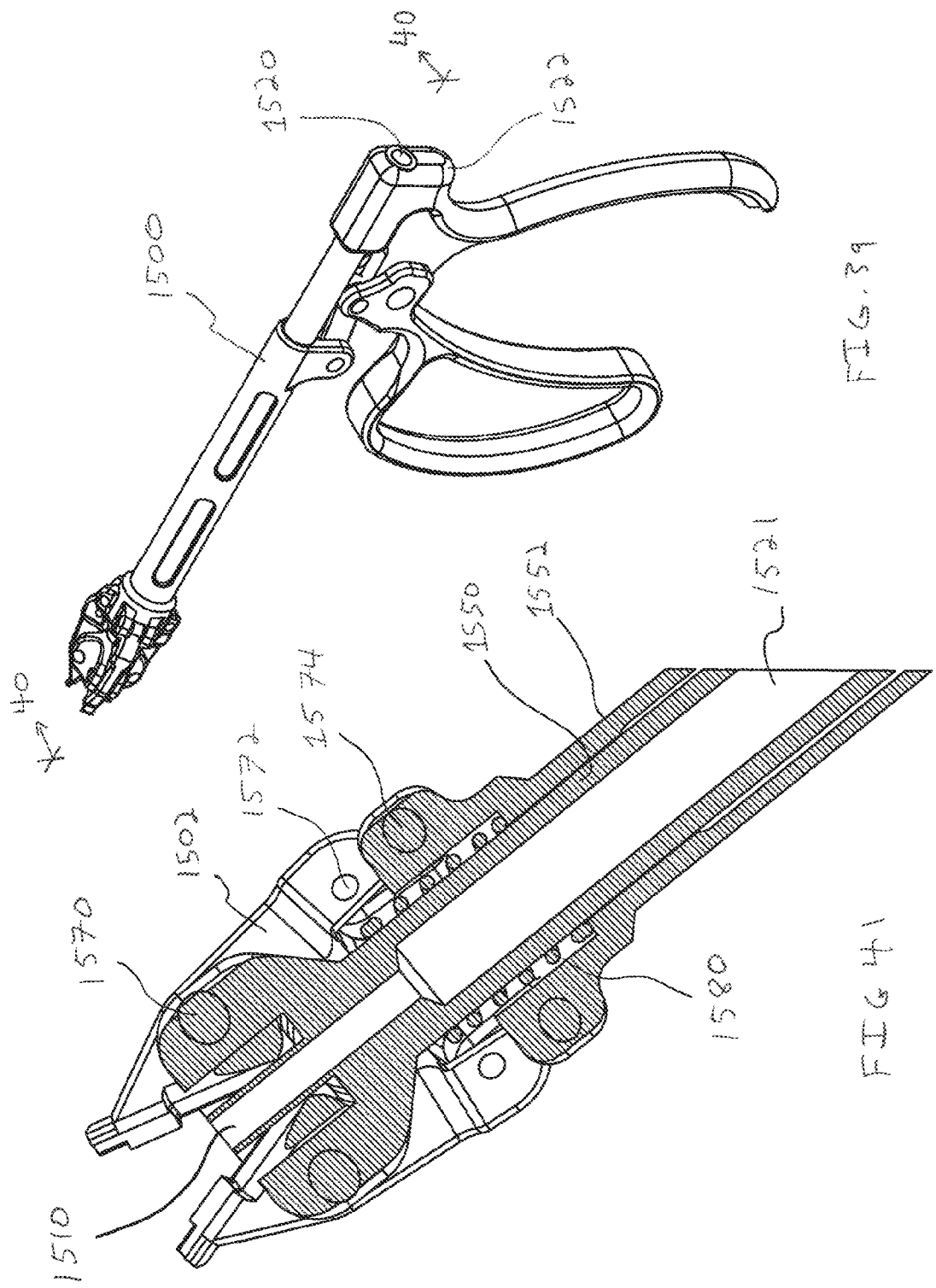

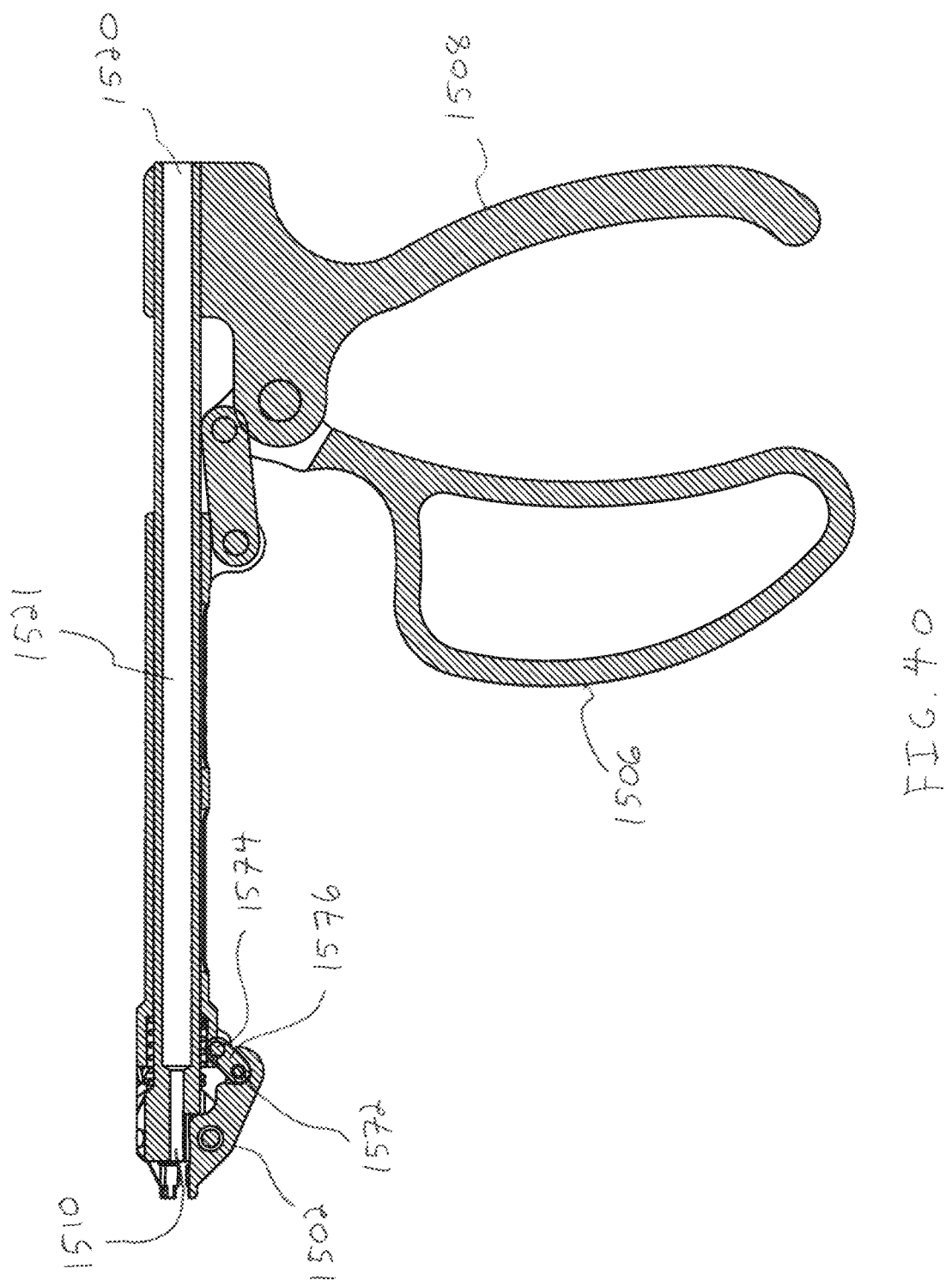

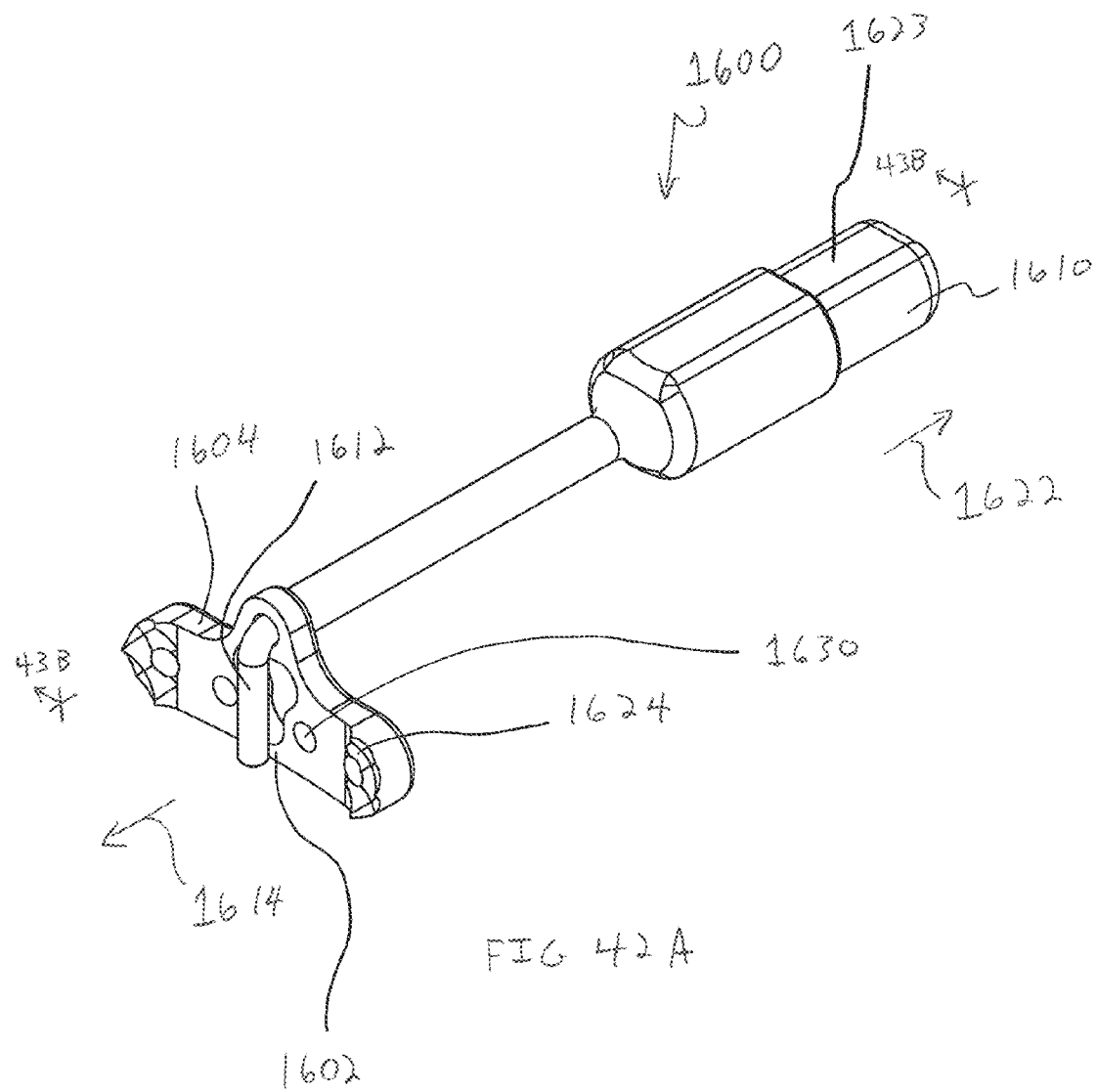

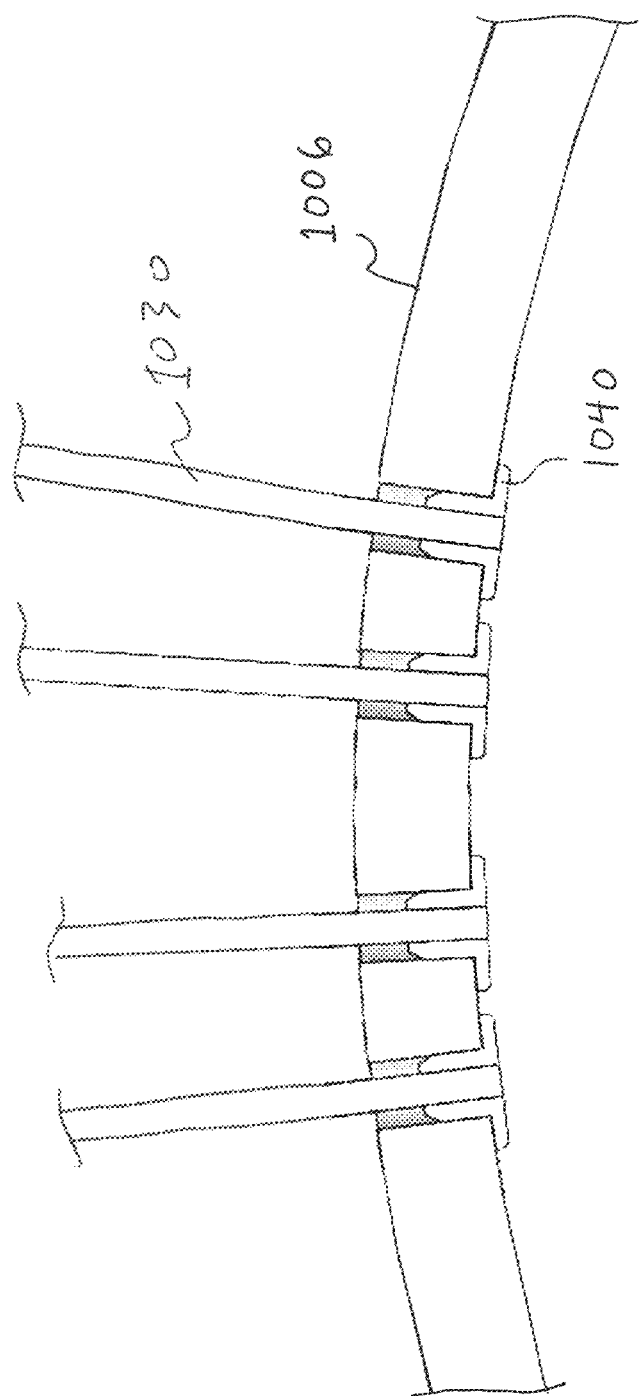

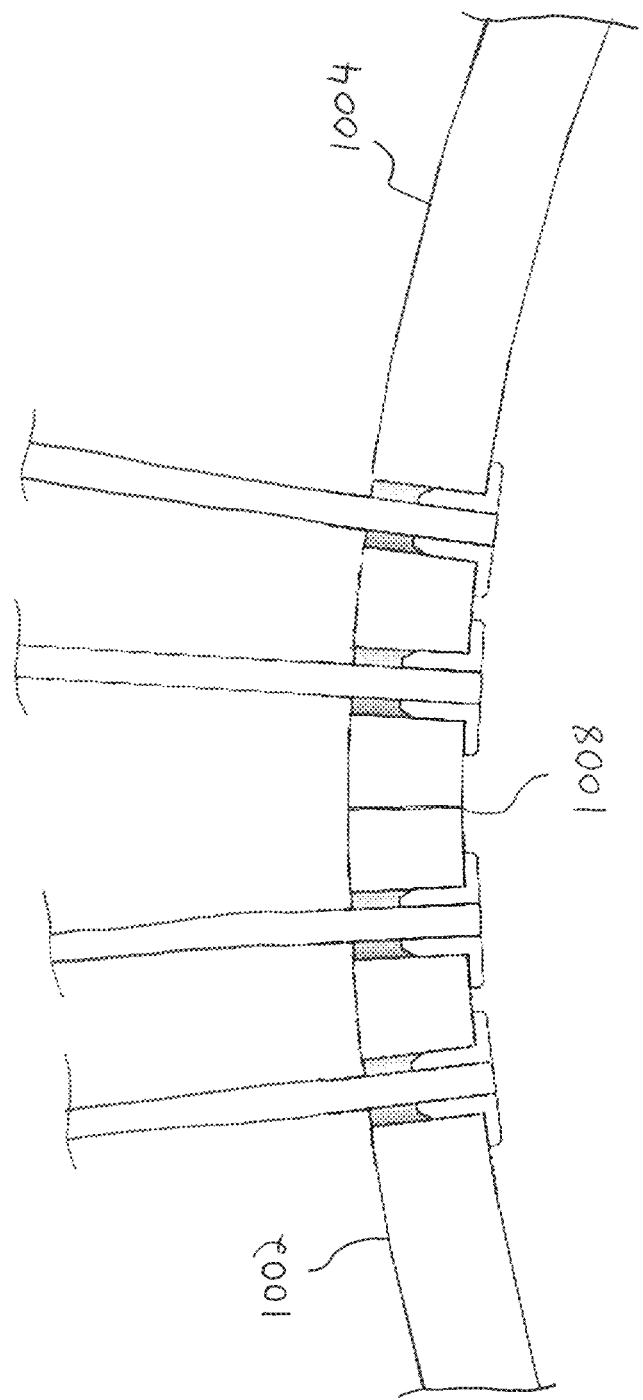

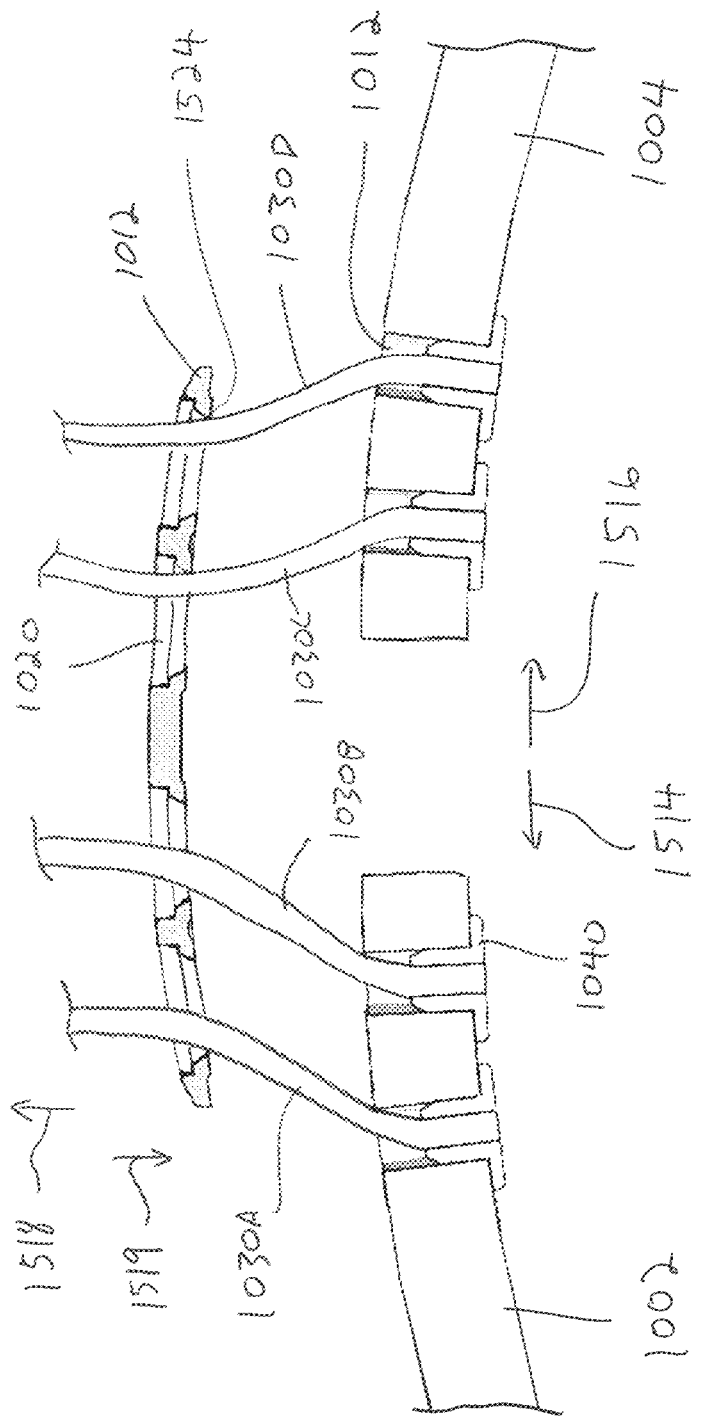

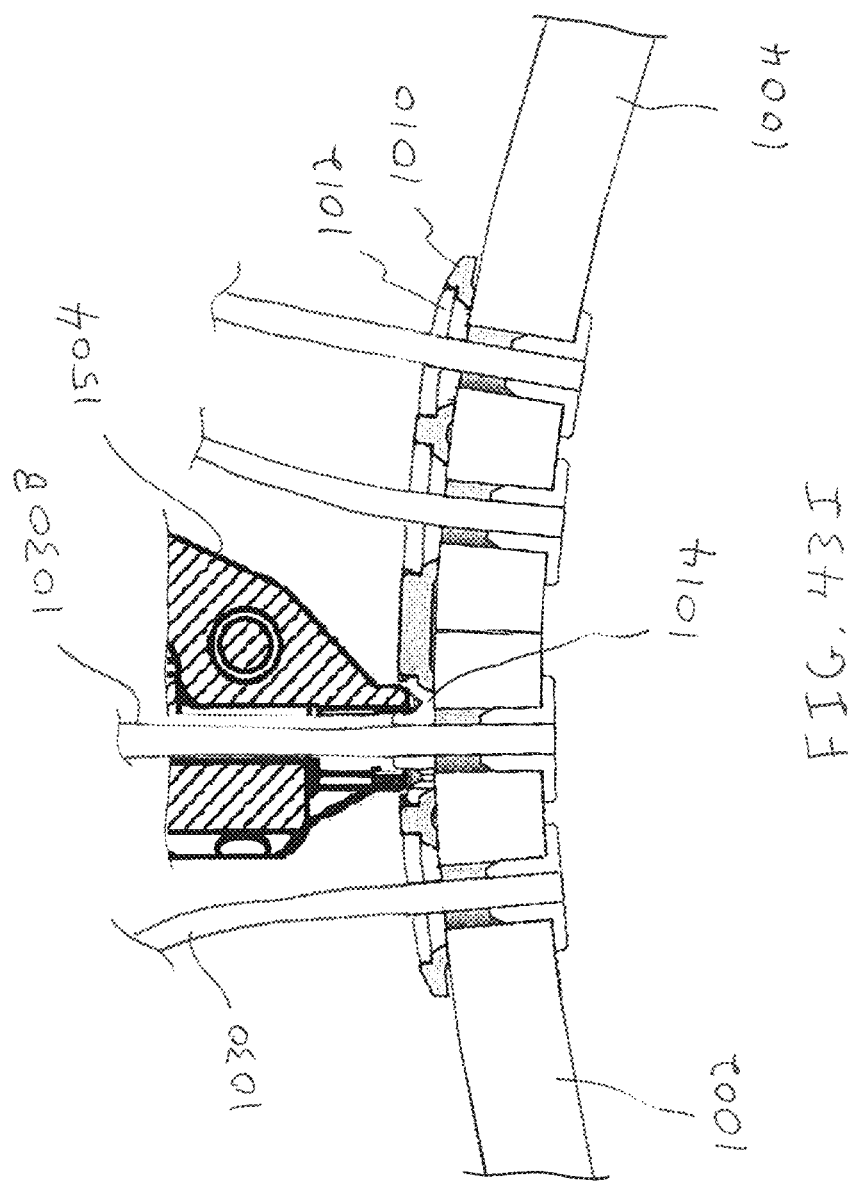

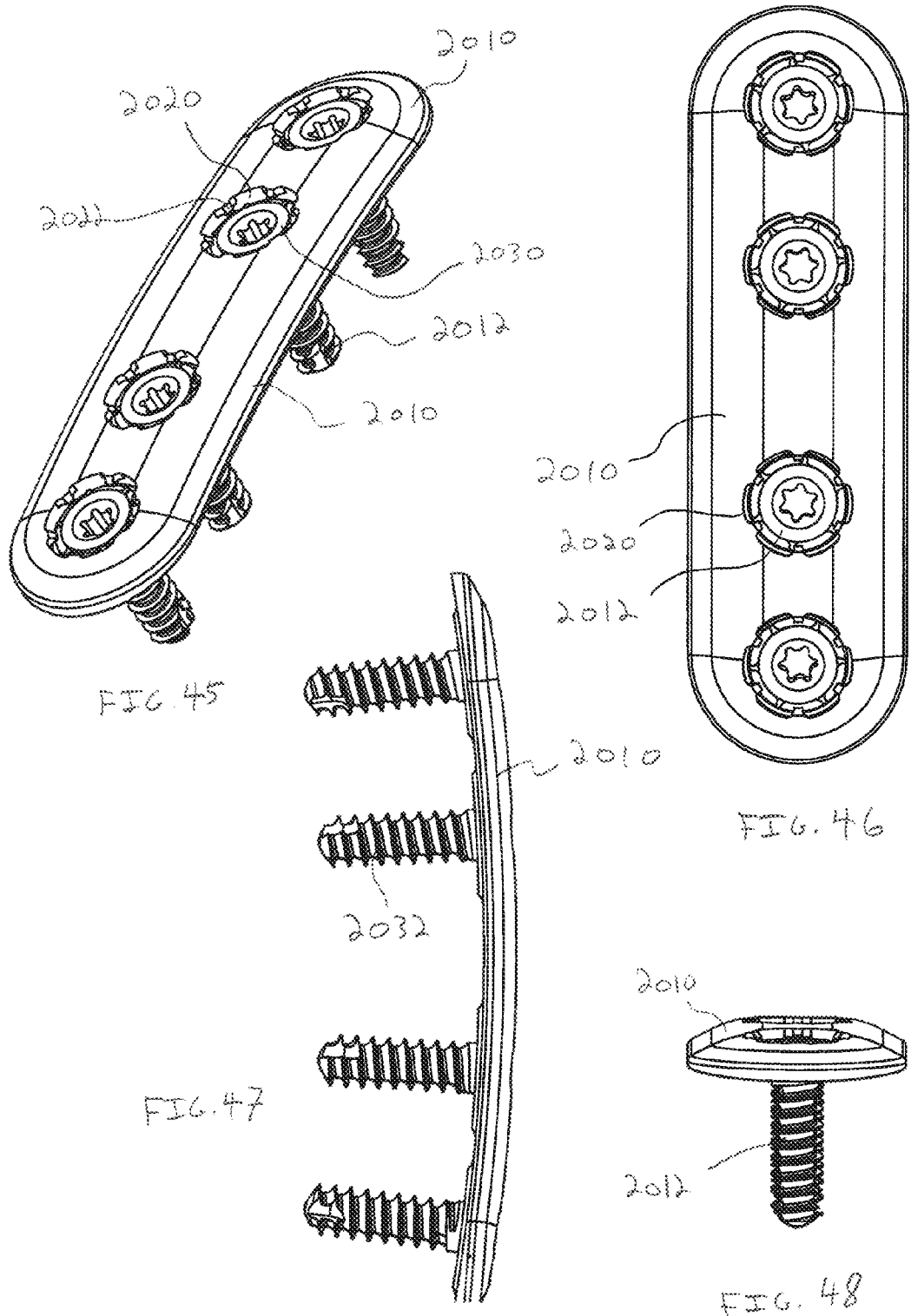

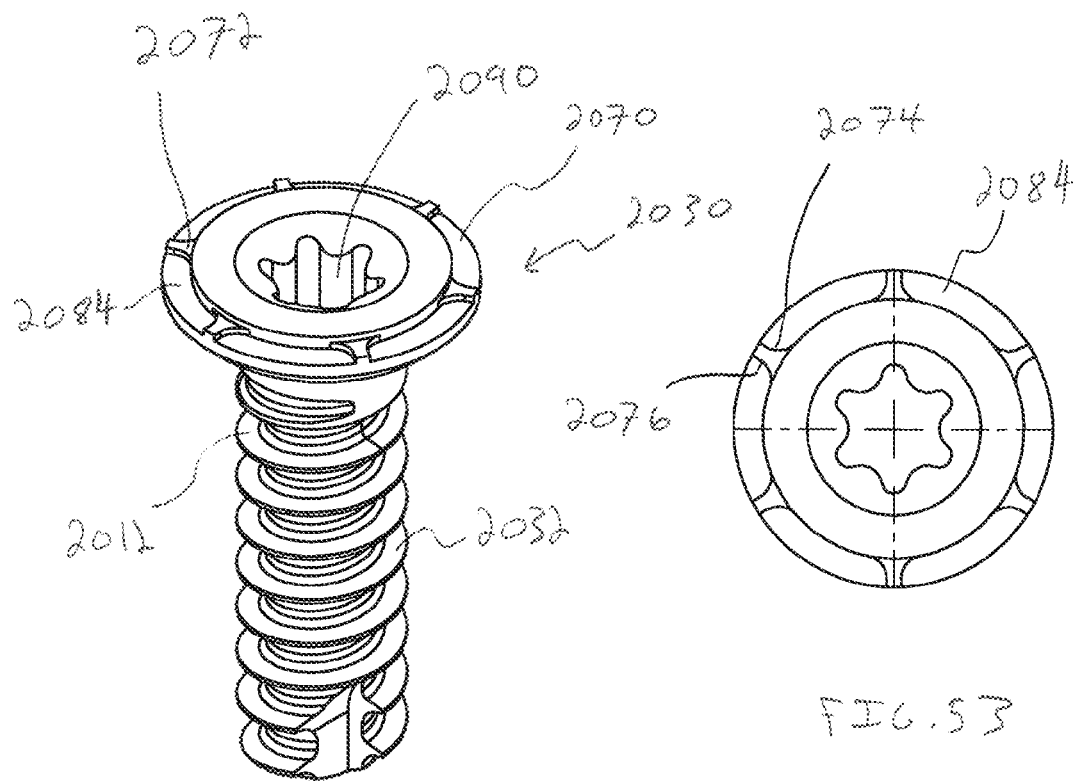

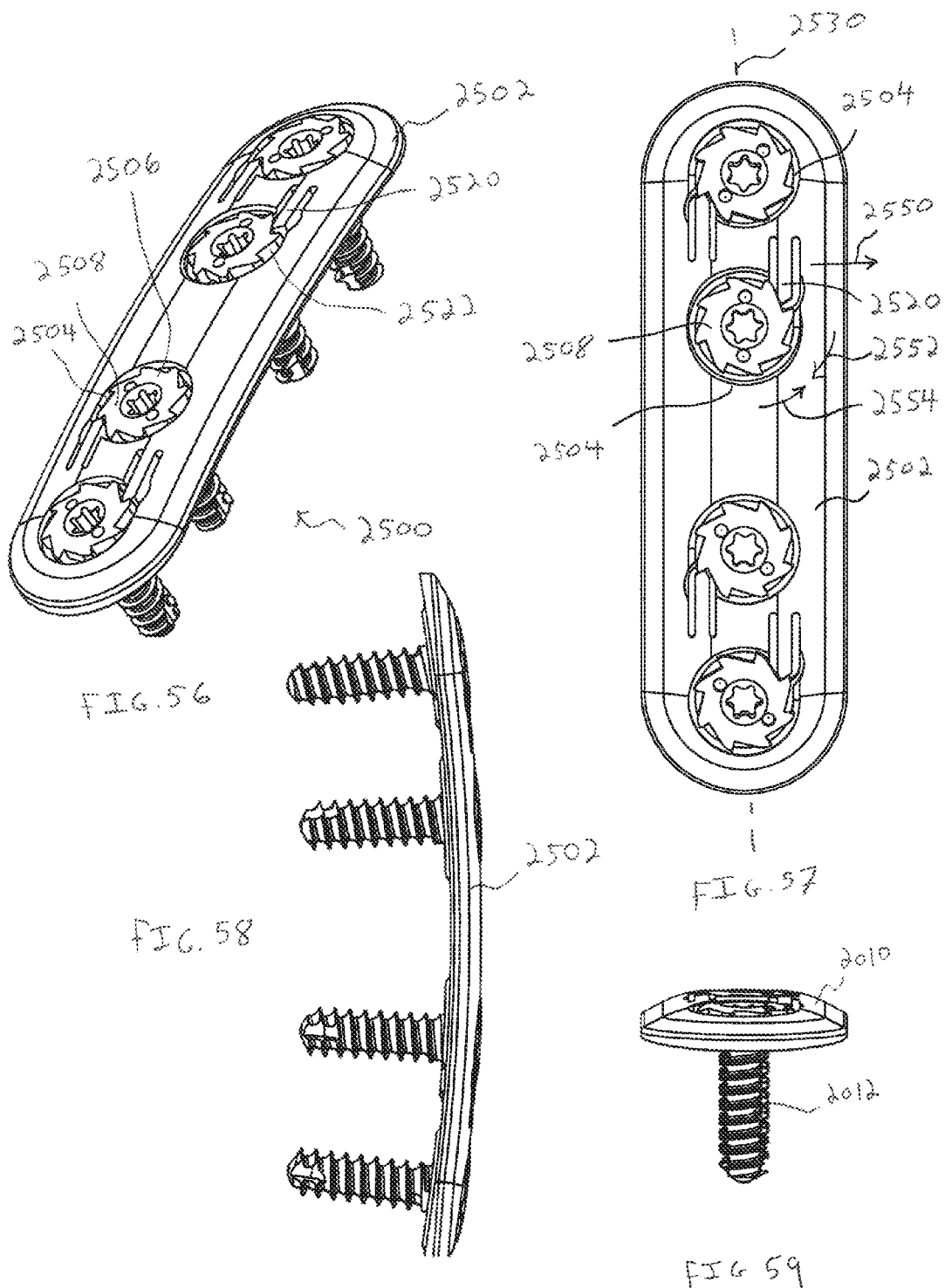

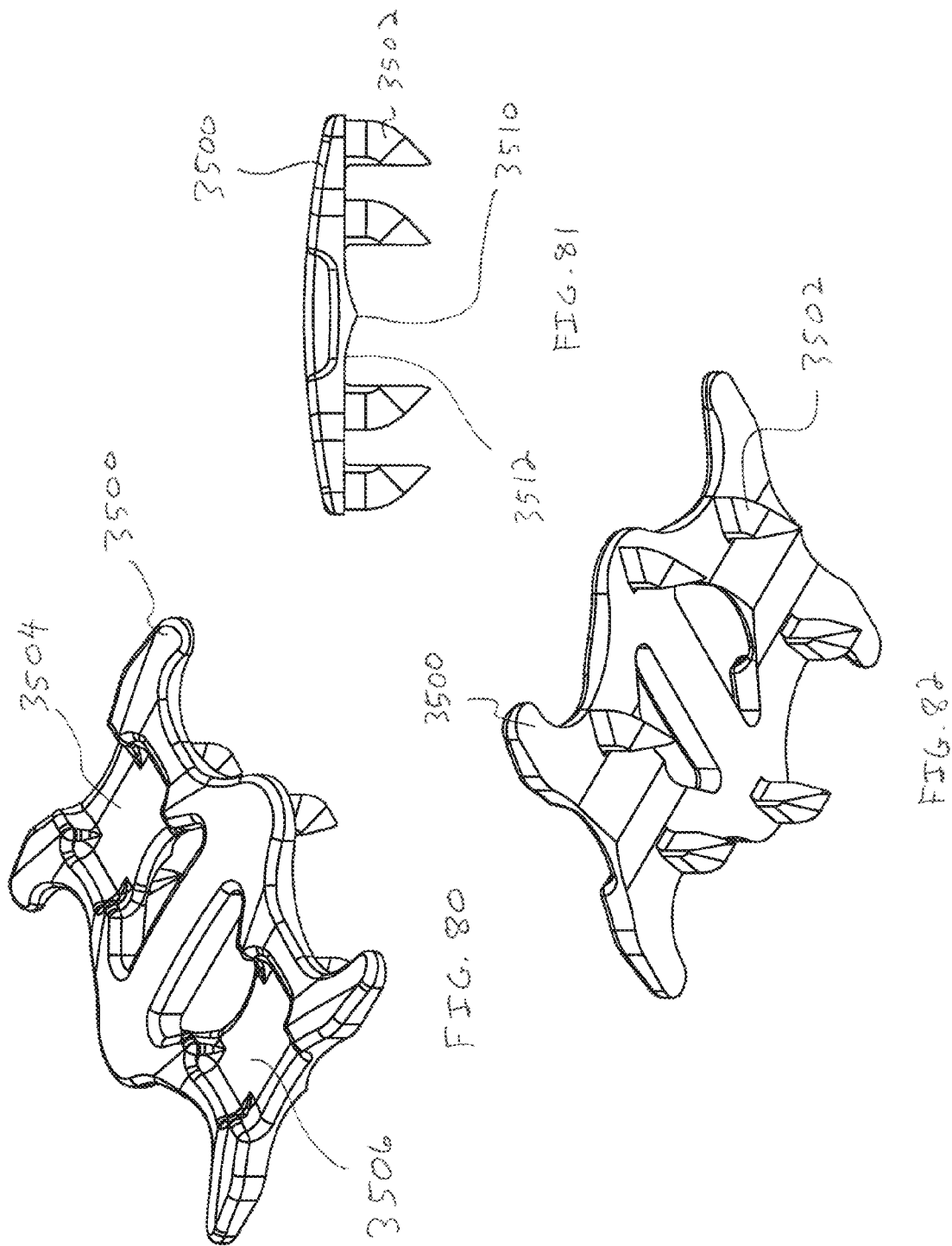

BONE PLATE SYSTEM AND METHOD

CROSS-REFERENCE TO RELATED APPLICATIONS

This application claims the benefit of U.S. Provisional Patent Application No. 61/580,560, filed Dec. 27, 2011, and U.S. Provisional Patent Application No. 61/710,354, filed Oct. 5, 2012, which are both hereby incorporated by reference in their entireties.

FIELD OF THE INVENTION

The invention relates to bone plate systems and, more particularly, to a bone plate system for stabilizing one or more bones.

BACKGROUND OF THE INVENTION

There are presently many different types of bone plate systems for securing bones so that the secured bones may fuse or heal. As used herein, the term bone may refer to a bone, a bone fragment, or a portion of a bone. One application for bone plate systems is repairing one or more ribs after a thoracotomy. A thoracotomy may involve cutting a rib or, in some instances, removing a section of a rib in order to provide access to tissues and organs within the chest cavity of a patient.

After the tissues or organs within the chest cavity have been operated upon, the ribs of the patient may need to be repaired. For example, if one of the ribs has been cut, a bone plate and screws may be used to secure the portions of the cut rib together. However, rib bones are relatively thin such that driving the screws into the portions of the cut rib exerts an outward pressure upon the bone which may splinter the bone. Further, rib bones consist of soft cancellous bone enclosed in a thin, compact layer of hard cortical bone. In order to achieve sufficient purchase in the bone, the screws may need to be driven completely through both layers of cortical bone and the cancellous bone therebetween. This may cause a portion of a screw shank to extend beyond the rib and irritate tissues within the chest cavity of the patient.

A thoracotomy may also involve using a retraction device to retract a pair of ribs of a patient apart in order to provide access to the tissues or organs within a patient's chest cavity. The retracted ribs may not return to their original position after the retraction device has been removed, which may be due to breaking of the surrounding bones and/or cartilage. In one approach, suture wire is looped around the pair of ribs and tightened to approximate the pair of ribs back together. However, each rib has a delicate neurovascular bundle of a vein, an aertery, and a nerve extending along the underside of the rib such that tightening the looped suture wire around the ribs may undesirably pinch the neurovascular bundle of one or more of the ribs.

In some thoracotomy procedures, a rib is cut and the portions of the cut rib are manipulated in order to gain access to a patient's chest cavity and, after the chest cavity has been accessed, a bone plate is used to promote post-operative fusion of the rib portions. More specifically, once the tissues or organs within the chest cavity have been accessed, the rib portions are approximated to return the rib portions to their initial positions. Pilot holes are drilled in the rib portions near the cut ends of the rib portions. Next, a bone plate is positioned on the rib portions so that throughbores of the bone plate are aligned with the pilot holes and the bone plate extends across the cut in the rib. Bone screws are driven through the bone plate throughbores to secure the bone plate to the rib portions and stabilize the rib and bone plate construct. One problem with this approach is that drilling the pilot holes in the rib portions may be difficult because the rib portions are hard to manipulate after being cut. Another problem is that obtaining a precise alignment of the pilot holes in the rib portions and the throughbores of the bone plate is challenging due to the difficulty in drilling properly spaced and oriented pilot holes in the cut rib portions.

SUMMARY OF THE INVENTION

In accordance with one aspect of the present invention, a bone plate system is provided for stabilizing one or more bone portions, such as a pair of rib portions. The bone plate system includes a bone plate member, a plurality of through openings of the bone plate member, and a plurality of cable connector devices including cable portions thereof. The cable connector devices are each configured to be inserted into a throughbore formed in one of the bone portions and one of the through openings of the plate member aligned therewith.

The cable connector devices have opposite end portions with one end portion configured to abut bone adjacent the respective throughbore and the other end portion configured to be operatively fixed to the bone plate member. By utilizing cable connector devices including a cable portion, each cable connector device can be advanced through one of the bone portion throughbores and secured to the bone plate member without exerting outward forces on the bone portion that may fracture the bone portion. Another advantage of this approach is that the cable connector devices eliminates the rigid, complex geometry often present with conventional bone plate/bone screw assemblies. More specifically, the other end portion of the cable connector device may permit the location at which the cable connector device is fixed to the bone plate member to be selected along the cable connector device to permit the orientations of the bone plate member and cable connector assemblies to be conformed to patient anatomy.

In one form, the cable portion of one of the cable connector devices includes a cable member and the other end portion comprises an end of the cable member which has been cut to a desired length. By permitting the cable member to be cut to length, the bone plate system provides a "one-size-fits all" approach wherein the cable member is cut to a length to fit the bone portion to which the cable connector device is being secured. This permits a single length of the cable connector devices to be provided with the bone plate system and then cut to length as needed to fit a particular patient anatomy, rather than providing a range of differently sized cable connector devices.

In accordance with another aspect of the present invention, a bone plate system is provided for securing one or more bone portions. The bone plate system includes a connector device having an elongate, flexible portion intermediate leading and trailing end portions of the connector device. The system further includes a plate member having through openings and a locking device associated with the plate member. The locking device has a receiving portion disposed in the plate member throughbore that is sized to permit the leading end portion of the connector device to be advanced therethrough when the locking device is in the unlocked configuration and sized to fix the connector device in the receiving portion when the locking device is in the locked configuration. By positioning the receiving portion in the plate member throughbore, the connector device may be easily advanced into the receiving portion and fixed thereto once the plate member throughbore has been aligned with a bone throughbore. Further, the receiving portion of the locking mechanism provides a lower profile of the bone plate system on the bone when compared to some prior systems where a locking device is located above the plate member which increases the height of those systems.

In accordance with another aspect of the present invention, a bone plate system is provided for stabilizing one or more bone portions, such as a pair of ribs that have been manipulated during a thoracotomy. The bone plate system includes a plurality of connector devices, such as surgical cables, having leading end portions for advancing through pre-drilled holes in the bones and trailing end portions for securing to the bones. The bone plate system includes a bone plate having a plurality of through openings sized to receive the leading end portions of the connector devices and locking devices with unlocked configurations that permit the leading end portions of the connector devices to be advanced into the locking devices. Once the leading end portions of the connector devices have been advanced into the locking devices, the locking devices can be reconfigured to a locked configuration to fix the bone plate to the bones using the connector devices.

In one form, the locking devices of the bone plate system include crimp members having crimpable portions positioned in the through openings of the bone plate between upper and lower surfaces of the bone plate. The crimpable portions have through apertures sized to receive the leading end portions of the connector devices and the crimpable portions may be crimped to fix the crimp members to the connector devices. By positioning the crimpable portions within the through openings of the plate member, the crimp members can be contained substantially entirely within the profile of the bone plate while still permitting rapid connection of the bone plate to the connector devices. Further, the trailing end portions of the connector devices may include plugs configured to engage the pre-drilled holes. The plugs may have outer surfaces that are generally even with or below the outer surface of the bone surrounding the pre-drilled holes when the trailing end portions of the connector devices are secured to the bones. Thus, the compact configuration of the crimp members and the bone plate, in combination with the plugs of the connector devices, minimizes the profile of the bone plate system on both sides of the bones once the bone plate system has been secured to the bones.

In accordance with another aspect of the present invention, a method is provided for approximating and securing a plurality of bones using a stabilization member, such as a bone plate. The method includes securing a first end of the stabilization member to a generally non-displaced bone and forming a hole in a displaced bone that has been retracted away from the non-displaced bone. The method further includes advancing a leading end portion of a surgical cable through the hole in the displaced bone and connecting a trailing end portion of the surgical cable to the displaced bone. Next, the leading end portion of the surgical cable is advanced through an opening at a second end of the stabilization member for subsequent connection thereto. By advancing the leading end portion of the surgical cable through the hole in the displaced bone, the trailing end portion of the surgical cable can be connected to the displaced bone without applying radially outward pressure on the bone, such as is caused by driving bone screws into bone, and possibly causing damage to the displaced bone.

The method further includes tensioning the surgical cable such that the stabilization member redirects the tension force in the surgical cable and pulls the trailing end portion of the surgical cable and the displaced bone connected thereto toward the non-displaced bone. This approach permits the bones to be rapidly and easily approximated by tensioning the surgical cable. In one form, the method further includes reconfiguring a locking device of the stabilization member to a locked configuration to fix the second end of the stabilization member to the surgical cable connected to the displaced bone such that the stabilization member is secured to the bones. This provides a secure construct of the stabilization member and the bones and utilizes a single surgical cable to both approximate the bones and fix the stabilization member to the bones.

In one approach, the non-displaced bone is a first rib and the displaced bone is a second rib that has been retracted away from the first rib during a thoracotomy procedure. The method includes forming a hole in the second rib before or after retraction that is spaced away from a neurovascular bundle running along the underside of the second rib. The method further includes advancing a leading end portion of a surgical cable through the hole in the second rib and tensioning the surgical cable to draw a plug on a trailing end portion of the surgical cable into engagement with the second rib to connect the trailing end portion of the surgical cable to the second rib. In this manner, the surgical cable can be connected to the second rib without pinching or otherwise damaging the neurovascular bundle thereof.

BRIEF DESCRIPTION OF THE DRAWINGS

FIGS. 2A and 2B are elevational and perspective views of one of the surgical cables of the bone plate system of FIG. 1 showing an enlarged plug at one end of the surgical cable;

FIG. 30 is an elevational view of the bone plate system of FIG. 29 showing the low profile of the bone plate and plugs on opposite sides of the rib;

FIG. 31 is a perspective view of the bone plate system of FIG. 29 showing the plugs secured on the underside of the rib;

FIG. 38 is an exploded schematic view of the tool of FIG. 34;

FIG. 39 is a rear perspective view of the tool of FIG. 34 showing an outlet opening for a cable above the handle of the tool;

FIG. 40 is a cross-sectional view taken across line 40-40 in FIG. 39;

FIG. 41 is a cross-sectional view of the distal end of the locking tool showing pivotal connections between the locking arms and shafts of the tool;

FIG. 42A is a perspective view of a guide tool that may be used to prepare bones for the bone plate of FIG. 27;

FIGS. 43A-43I illustrate a method of securing the bone plate system of FIG. 27 to a rib;

FIG. 45 is a perspective view of the bone plate system of FIG. 44 showing retainer members of the bone plate disposed circumferentially around upper ends of the throughbores of the bone plate for restricting back out of bone screws from the bone plate;

FIG. 46 is a top plan view of the bone plate of FIG. 44 showing spacings between the pairs of bone screws near the ends of the plate that are closer than the spacing between the pairs of bone screws near the middle of the plate;

FIGS. 47 and 48 are elevational views of the bone plate system of FIG. 44 showing a generally convex upper surface of the bone plate;

FIG. 52 is a perspective view of one of the bone screws of the bone plate system of FIG. 44 showing radially extending structures configured to engage the retention members of the bone plate and restrict turning of the bone screw.

FIG. 53 is a plan view of the bone screw of FIG. 52 showing a central recess configured to receive a drive tool;

FIG. 56 is a perspective view of another bone plate system showing a bone plate and screws having retention features which resemble a gear and pawl mechanism;

FIG. 57 is a top plan view of the bone plate system of FIG. 56 showing the retention members of the bone plate oriented in different directions along a longitudinal axis of the bone plate;

FIGS. 58 and 59 are elevational views of the bone plate system of FIG. 56 showing a generally convex outer upper surface of the bone plate member;

FIG. 80 is a perspective view of the plate member of FIG. 78 showing recesses in the upper surface of the plate member adapted to receive locking devices of wires, cables or other connector devices;

FIG. 81 is an end elevational view of the plate member of FIG. 79 showing a ridge extending from a bottom surface of the plate member; and FIG. 82 is a bottom perspective view of the plate member of FIG. 79 showing the teeth extending downwardly from the bottom surface of the plate member.

DETAILED DESCRIPTION OF THE PREFERRED EMBODIMENTS

Figure 1:
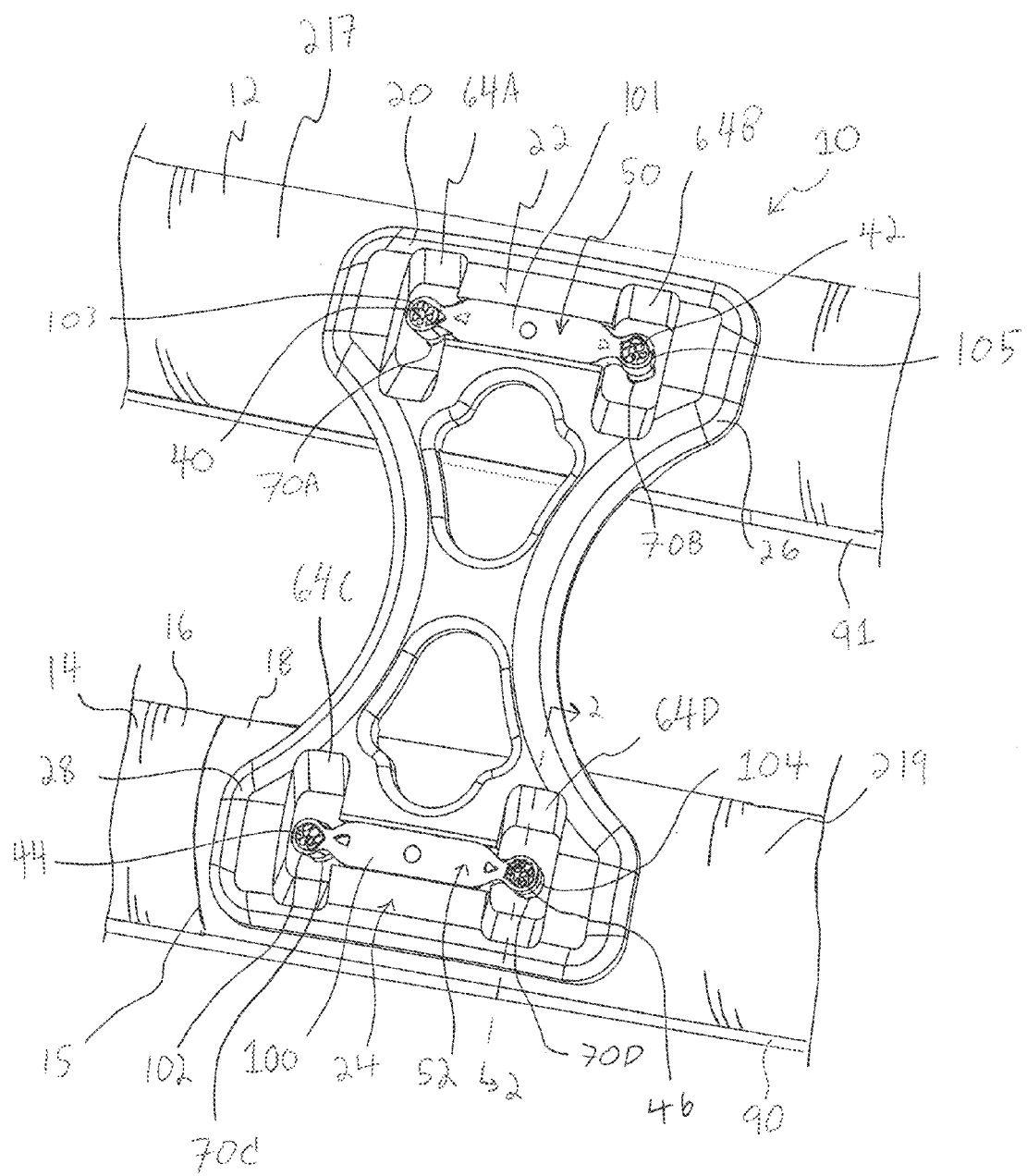
FIG. 1 is a perspective view of a bone plate system in accordance with one aspect of the present invention showing the bone plate system secured to a pair of ribs.

Referring to FIG. 1, a bone plate system 10 is provided for stabilizing one or more bones, such as ribs 12, 14, after the rib 14 has been cut such as along cut line 15 into two portions 16, 18 as part of a thoracotomy procedure. The bone plate system 10 includes a stabilizing member, such as bone plate 20, sized to extend between the ribs 12, 14 and keep the rib portion 18 relatively stable and in proximity to the rib portion 16. This decreases the relative movement between the rib portions 16, 18 due to breathing and movement of the patient and may improve post-operative fusion between the rib portions 16, 18.

The bone plate 20 includes locking devices 22, 24 at opposite ends 26, 28 thereof for fixing the plate 20 at its ends 26, 28 to connector devices that may include cable portions. One example of these connector devices are surgical cables 40, 42, 44 and 46, as shown in FIGS. 1, 2, 2A, and 2B. In one form, the locking devices 22, 24 include crimp assemblies 50, 52 for fixing the bone plate 20 to the surgical cables 40, 42, 44, 46 after leading end portions 72 of the surgical cables 40, 42, 44, 46 have been advanced through holes 70A, 70B, 70C, and 70D formed in the ribs 12, 14 (see FIGS. 18, 19, and 21, 22). Rather than utilizing bone screws to secure the bone plate 20 to the ribs 12, 14, the surgical cables 40, 42, 44, 46 can be advanced through the holes 70A-70D and connected to the ribs 12, 14 without applying radially outward pressure on the ribs 12, 14, such as is caused by driving bone screws into bone. Thus, the likelihood of splintering the ribs 12, 14 while securing the bone plate system 10 to the ribs 12, 14 is minimized.

Figure 17:
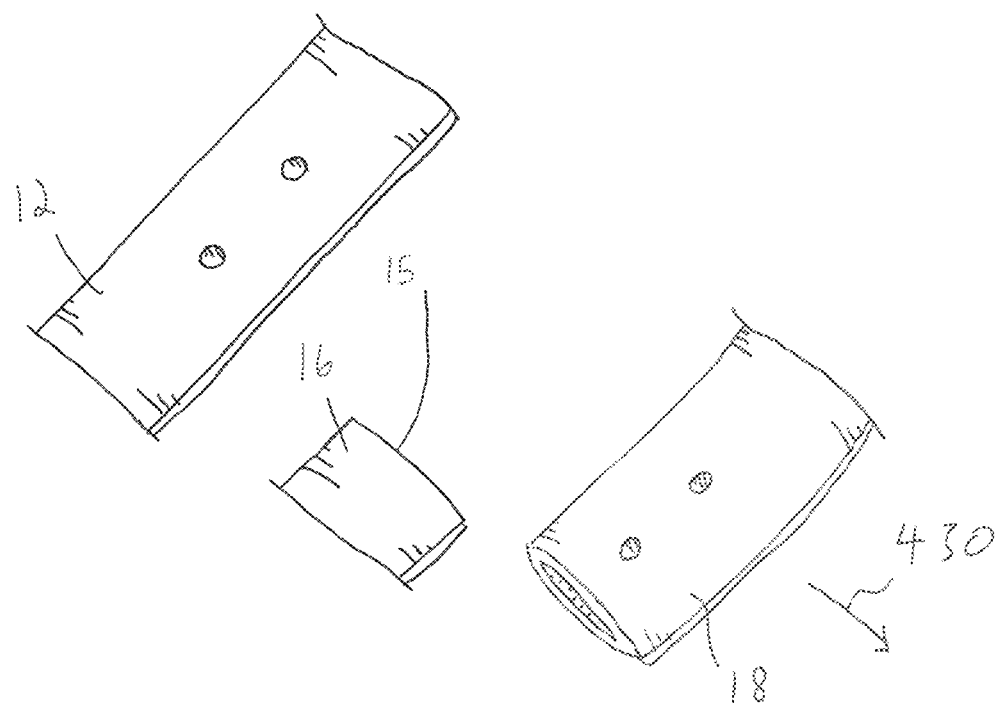

The bone plate system 10 also provides a rapid and easy-to-use approach for approximating the ribs 12, 14 in the event that the ribs 12, 14 have been retracted apart, such as during a thoracotomy procedure. For example, the rib portion 18 may be moved away from the rib 12 due to retraction of the ribs 12, 14, as shown in FIG. 17. However, the rib portion 18 may be brought back into its unretracted position by securing the bone plate 20 at the end 26 thereof to the rib 12 (see FIG. 20), advancing the leading end portions 72 of the surgical cables 44, 46 through the holes 70C, 70D in the rib portion 18 and through the crimp assembly 52 (see FIG. 21), connecting trailing end portions 74 of the surgical cables 44, 46 to the rib portion 18, and pulling one or both of the leading end portions 72 of the surgical cables 44, 46 in direction 470 away from the bone plate 20 (see FIG. 22). The crimp assembly 52 acts as a pulley to redirect the tension forces in the surgical cables 40, 42 and draw the rib portion 18 toward the rib 12. Once the ribs 12, 14 have been sufficiently approximated, as shown in FIG. 22, the crimp assembly 52 is reconfigured to a locked configuration to fix the bone plate 20 at the end 28 thereof to the rib portion 18. The bone plate system 10 thereby provides the ability to quickly and easily approximate ribs 12, 14 without the need for a separate approximation device such as forceps, although such devices may be used to assist with the approximation process described herein. Further, because the holes 70C, 70D may be preformed to be spaced from a neurovascular bundle 90 running along the underside of the rib portion 18, the trailing end portions 74 of the surgical cables 44, 46 can be connected to the rib portion 18 and used to approximate the rib portion 18 without pinching or otherwise damaging the neurovascular bundle 90.

With reference to FIG. 1, the bone plate 20 has through openings 64A-64D extending therethrough and the crimp assemblies 50, 52 include crimp members 100, 101 that extend between pairs of though openings 64A, 64B and 64C, 64D. Each crimp member 100, 101 has a pair of heads 102, 104 and 103, 105 that are each centrally positioned within one of the through openings 64A-64D when the crimp member 100, 101 is mounted to the bone plate 20. The heads 102, 104 and 103, 105 of the crimp assemblies 50, 52 are initially in a slip-fit relation with the surgical cables 40, 42, 44, 46, but the crimp assemblies 50, 52 may be fixed to the surgical cables 40, 42, 44, 46 by crimping the heads 102, 104 and 103, 105 onto the surgical cables 40, 42 and 44, 46. As shown in FIG. 1, the heads 102, 104 and 103, 105 are positioned centrally within the through openings 64A-64D so as to be generally unobstructed by the bone plate 20 to increase the ease with which the leading end portions 72 of the surgical cables 40, 42, 44, 46 may be advanced into and through apertures 152, 186, 243, and 245 of the heads 102, 104 and 103, 105 (see FIG. 6). Further, the heads 102, 104 and 103, 105 are contained substantially entirely within the through openings 64A-64D and provide a compact, secure mechanism for locking the bone plate 20 to the surgical cables 40, 42, 44, 46. Specifically, the heads 102, 104, 103, 105 have outer surfaces disposed radially inward from bone plate surfaces which define the through openings 64A-64D and are disposed at or below an upper surface 73 of a bone plate body 20a (see FIG. 2).

Figure 2:
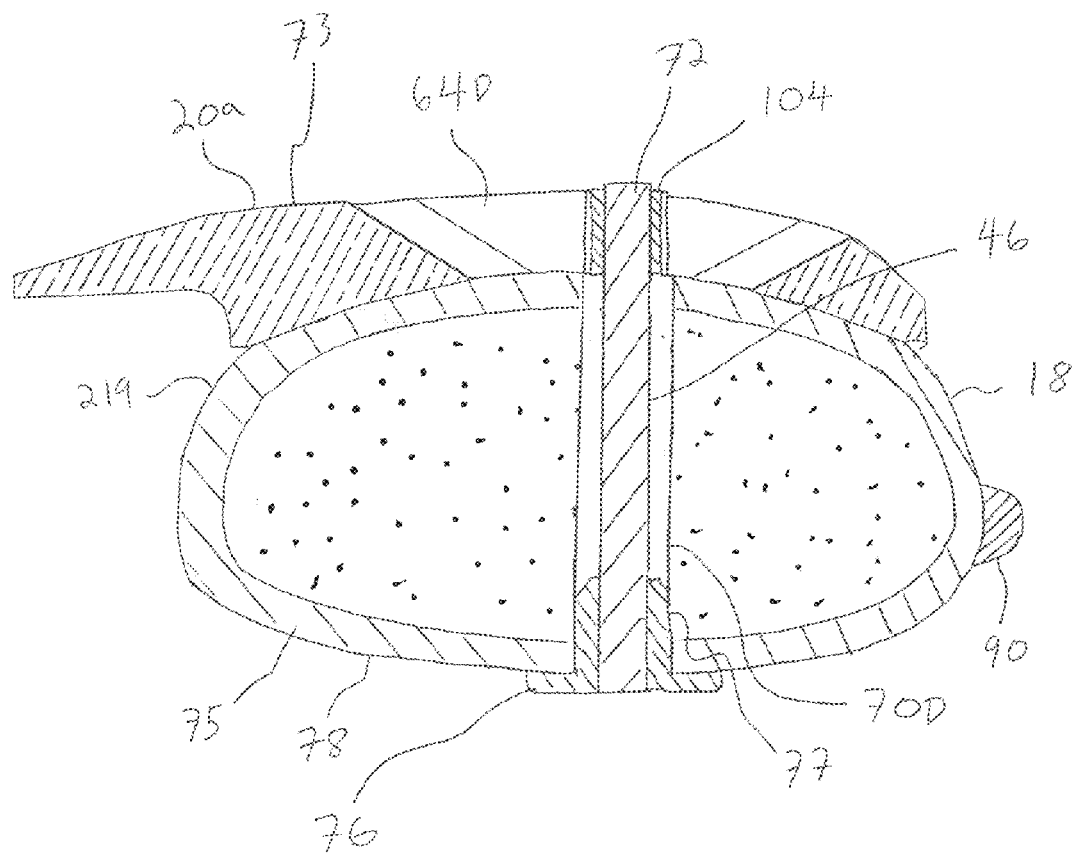
FIG. 2 is a cross-sectional view taken along line 2-2 in FIG. 1 showing a surgical cable connected at one end thereof to a head of a crimp member of the bone plate and at an opposite end thereof to an underside of one of the ribs.
Figure 2B:
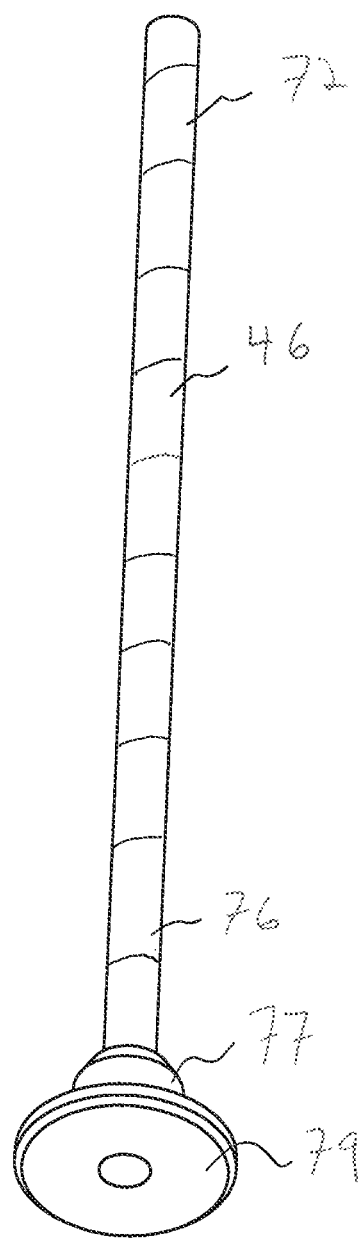

The connection between the head 104 of the crimp member 100 and the surgical cable 46 is shown in greater detail in FIG. 2. More specifically, the head 104 is crimped to the surgical cable 46 after the leading end portion 72 has been advanced from an underside 78 of the rib portion 18, through hole 70D in the rib portion 18, into and through the aperture 152 of the head 104 of crimp member 100, tensioned, and cut to length. The surgical cable leading end portion 72 and the crimp member head 104 are generally flush with or below an upper surface 73 of the plate body 20a of the bone plate 20, which minimizes irritation to surrounding tissues, as shown in FIG. 2. As will be discussed in greater detail below, tensioning the surgical cable 46 pulls a stop member of the surgical cable trailing end portion 76, such as a plug 77, into engagement with cortical bone 75 surrounding the hole 70D. The plug 77 has a flange 79 that abuts against the cortical bone 75 and resists pull-through of the trailing end portion 76, as shown in FIGS. 2A and 2B. As shown in FIG. 2, the flange 77 is relatively flush with the underside 78 of the rib portion 18 to minimize irritation to tissues and organs within the patient's chest cavity. Thus, the connections between the crimp member head 104 and the surgical cable leading end portion 72, and the rib underside 78 and the surgical cable trailing end portion 76, secure the bone plate 20 to the rib portion 18 by capturing the rib portion 18 between the bone plate 20 and the surgical cable trailing end portion 76. Further, the connection between the crimp member head 104 and the surgical cable leading end portion 72 is generally within the profile of the bone plate 12 and the connection between the cortical bone 78 and the surgical cable trailing end portion 76 is generally flush with the rib underside 78 such that the amount the bone plate system 10 extends into tissues on either side of the rib portion 18 is minimized.

Figure 3:
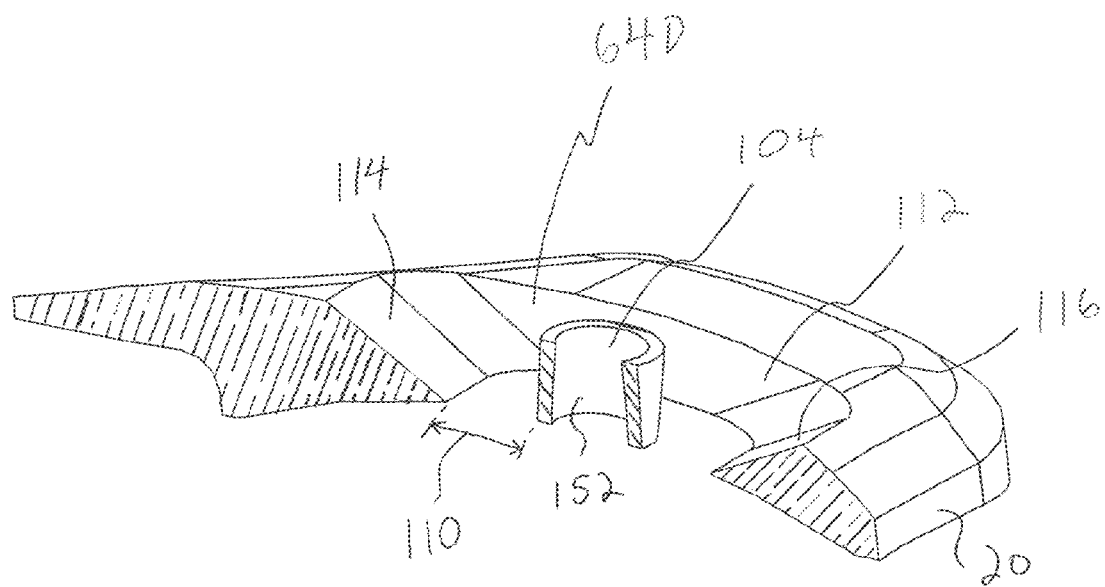
FIG. 3 is a perspective sectional view similar to FIG. 2 except that the rib and surgical cable are removed to illustrate the spacing of the head of the crimp member from the plate surface extending about the through opening.
Figure 23:
Figure 24:
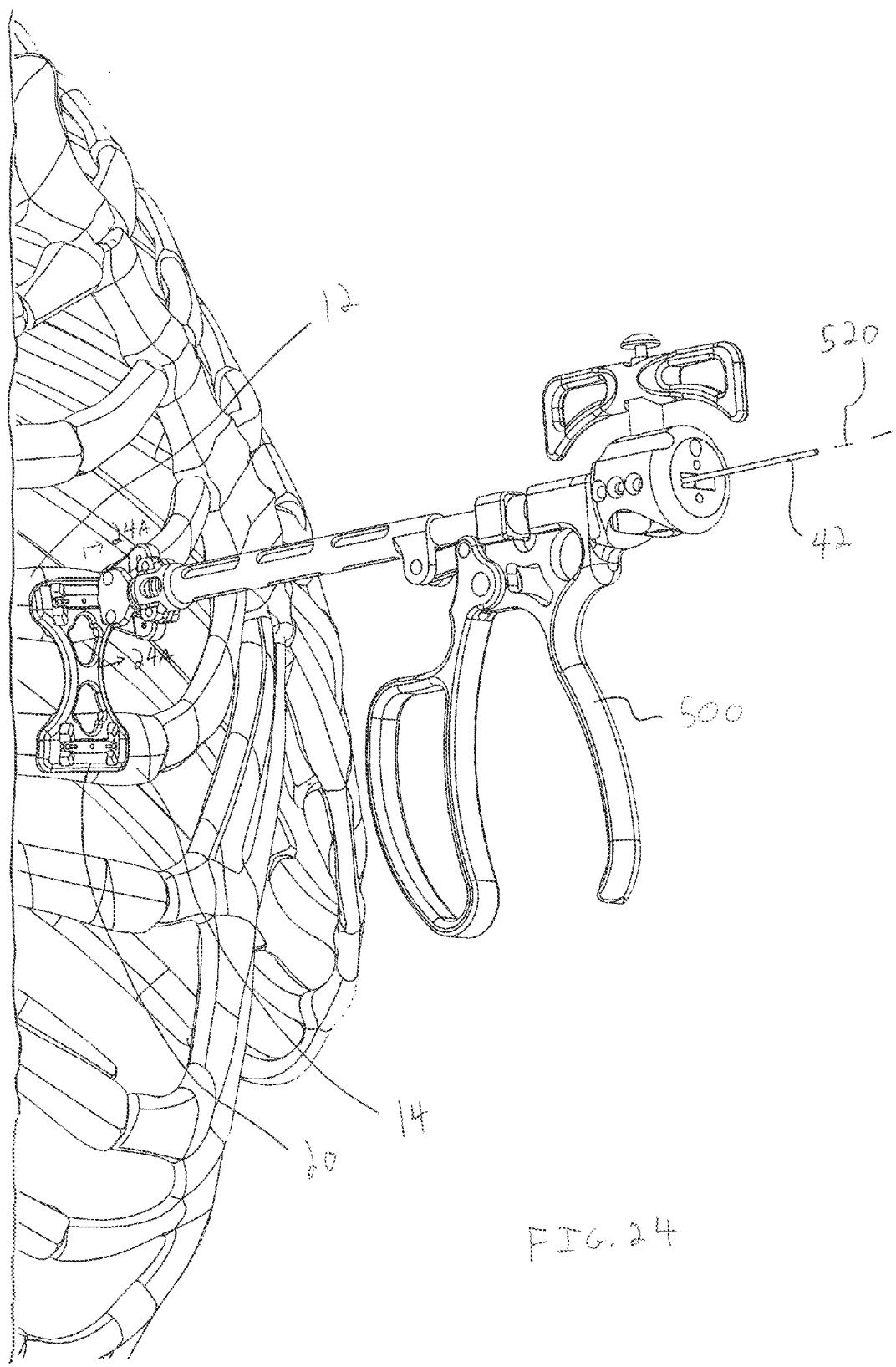
Figure 24A:
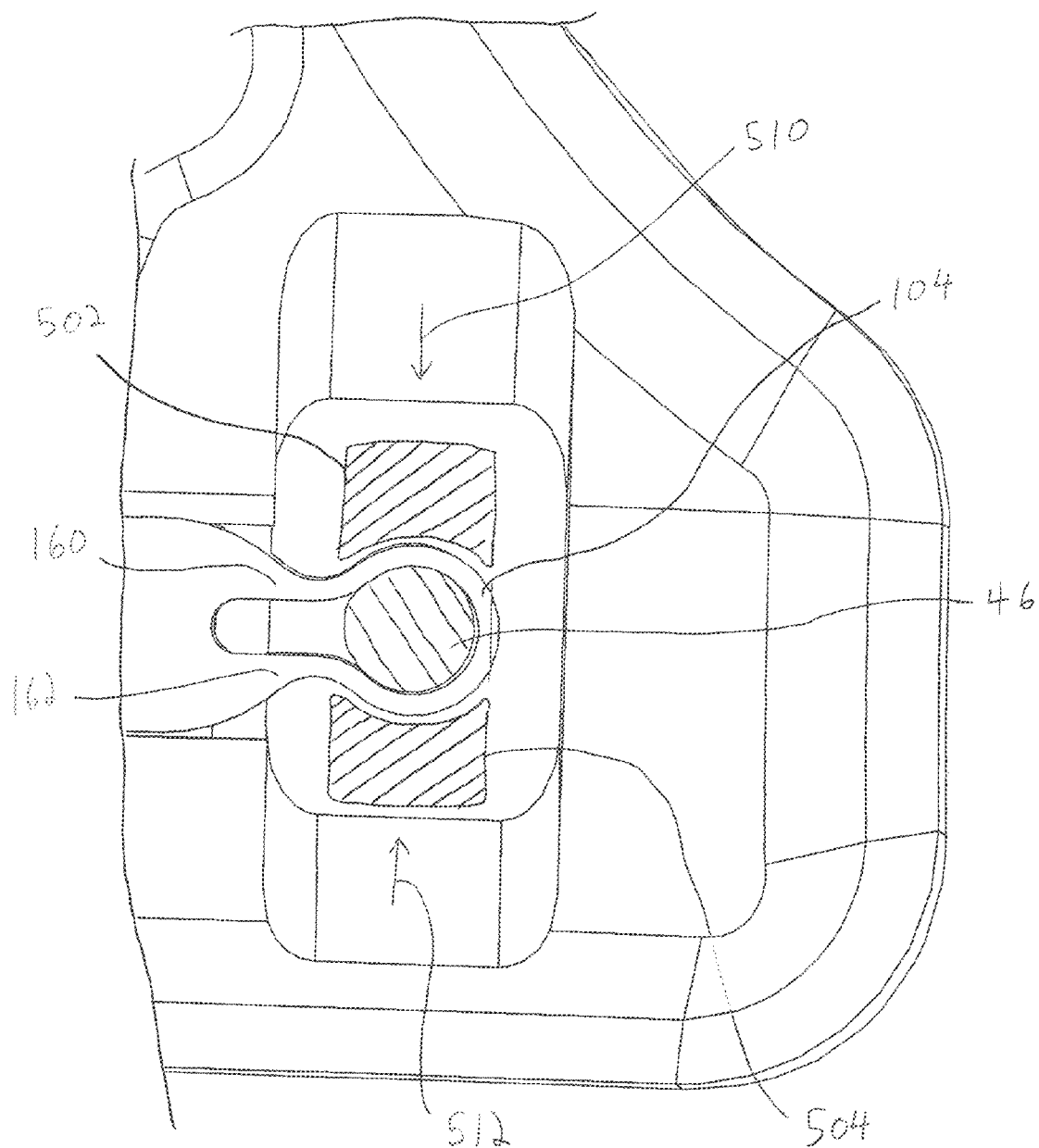
Figure 25:
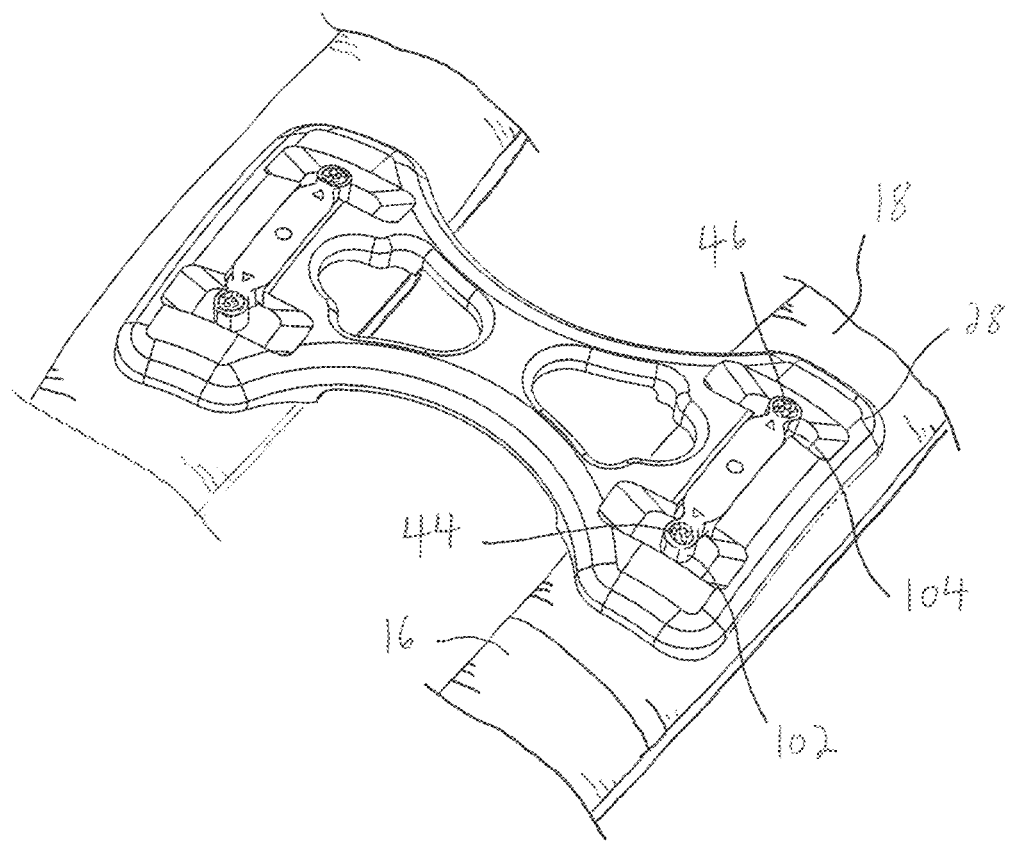

In one approach, a crimp tool 500 is used to crimp the heads 102, 104 and 103, 105 onto the surgical cables 40, 42, 44, 46, as shown in FIGS. 23 and 24. To improve the ease of use of the crimp tool 500, the bone plate 20 has features that provide clearance for positioning jaws 502, 504 of the crimp tool 500 in a crimping position on the heads 102, 104 and 103, 105. With reference to through opening 64D in FIG. 3, the through opening 64D has walls 112 extending thereabout that form a gap spacing 110 from the head 104 to allow jaws 502, 504 of the crimp tool 500 to be advanced along opposite sides of the head 104, as shown in FIG. 24A. Further, the walls 112 include incline walls 114, 116 that guide the jaws 502, 504 into position on opposite sides of the head 104 and restrict the jaws 502, 504 from passing beyond a predetermined vertical position within the through opening 64D. In this manner, the contact between the jaws 502, 504 and the incline walls 114, 116 provides tactile feedback to the surgeon that the jaws 502, 504 are in position relative to the head 104 and may be actuated to crimp the head 504 onto the surgical cable 46.

Figure 4:
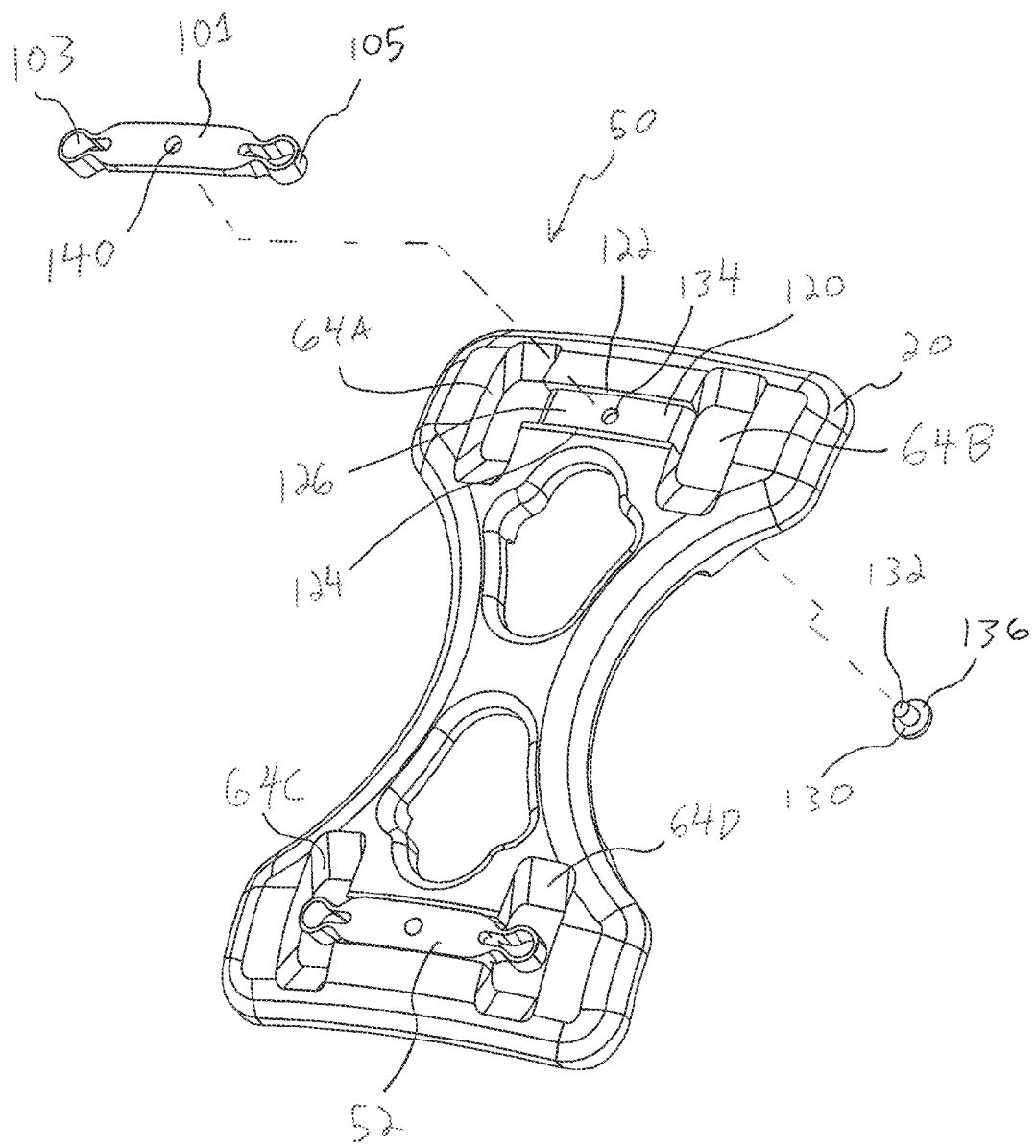
FIG. 4 is a partially exploded view of the bone plate of FIG. 1 with one of the crimp members removed from the bone plate to show a receiving structure of the bone plate which supports the crimp member.

In addition to providing clearance for the jaws 502, 504 of the crimp tool 500, the bone plate 20 has features near the through openings 64A-64D for supporting the crimp assemblies 50, 52. With reference to FIG. 4, the bone plate 20 includes a U-shaped channel 120 sized to snugly engage the crimp member 101 with the crimp member 101 connected to the bone plate 20. The channel 120 has vertical walls 122, 124 that restrict movement of the crimp member 100 and a floor 126 that supports the crimp member 101 presses once the surgical cables 40, 42 have been tensioned and fixed thereto.

To connect the crimp member 101 to the bone plate 20, the crimp assemblies 50, 52 include a set pin 130 having a post 132 sized to fit through an aperture 134 in the floor 126. The set pin 130 has a flange 136 that is sized larger than the aperture 134 to resist pull-through of the set pin 130 and is countersunk within the aperture 134 so that the flange 136 does not extend outward from a lower, seating surface 230 of the bone plate 20 (see FIG. 8). During assembly, the post 132 is advanced into the aperture 134 until the flange 136 seats firmly within the aperture 134 and the crimp member 101 is pressed downward into slot 120 such that an aperture 140 thereof passes downward onto the post 132 of the set pin 130. The crimp member 101 is then welded or otherwise connected to the post 132 to rigidly connect the crimp member 101 to the set pin 130 and capture the bone plate floor 126 between the crimp member 101 and the set pin 130. At this point, the crimp member 101 is fixed to the bone plate 20 and can transfer the loads applied from the surgical cables 40, 42 to the bone plate 20.

Figure 5:
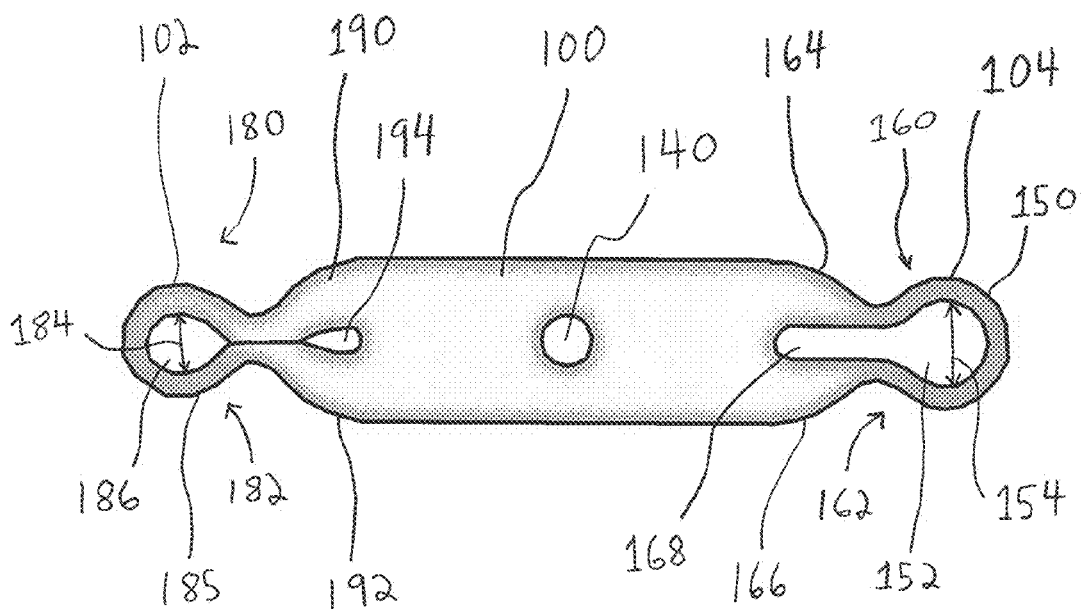
FIG. 5 is a plan view of one of the crimp members of the bone plate system of FIG. 1 showing one head of the crimp member crimped and the other head uncrimped.

With reference to FIG. 5, the heads 102, 104 of the crimp member 100 generally have an uncrimped configuration (see head 104) and a crimped configuration (see head 102). In the uncrimped configuration, the head 104 has a wall 150 that extends about a through aperture 152 with a diameter 154 selected such that the wall 150 is in a slip fit configuration with the surgical cable 46 and the leading end portion 72 of the surgical cable 42 can be advanced through the aperture 152. The head 104 has crimpable portions 160, 162 configured to receive the jaws 502, 504 of the crimping tool 500 (see FIGS. 24 and 24A). The crimpable portions 160, 162 also include arms 164, 166 initially separated by a gap 168, as shown in FIG. 5. With reference to head 102, crimping the crimpable portions 180, 182 thereof together decreases a diameter 184 of an aperture 186 of the head 102. More specifically, crimping the crimpable portions 180, 182 presses a wall 185 of the head 102 against the surgical cable 40 and deforms arms 190, 192 of the crimpable portions 180, 182 toward each other. The deformation of the arms 190, 192 can be seen by the difference in the size of a gap 194 between arms 190, 192 compared with the size of the gap 168 between arms 164, 166. The deformed diameter 184 of the head 102 is selected to provide a compression fit between the wall 185 and the surgical cable 40.

Figure 6:
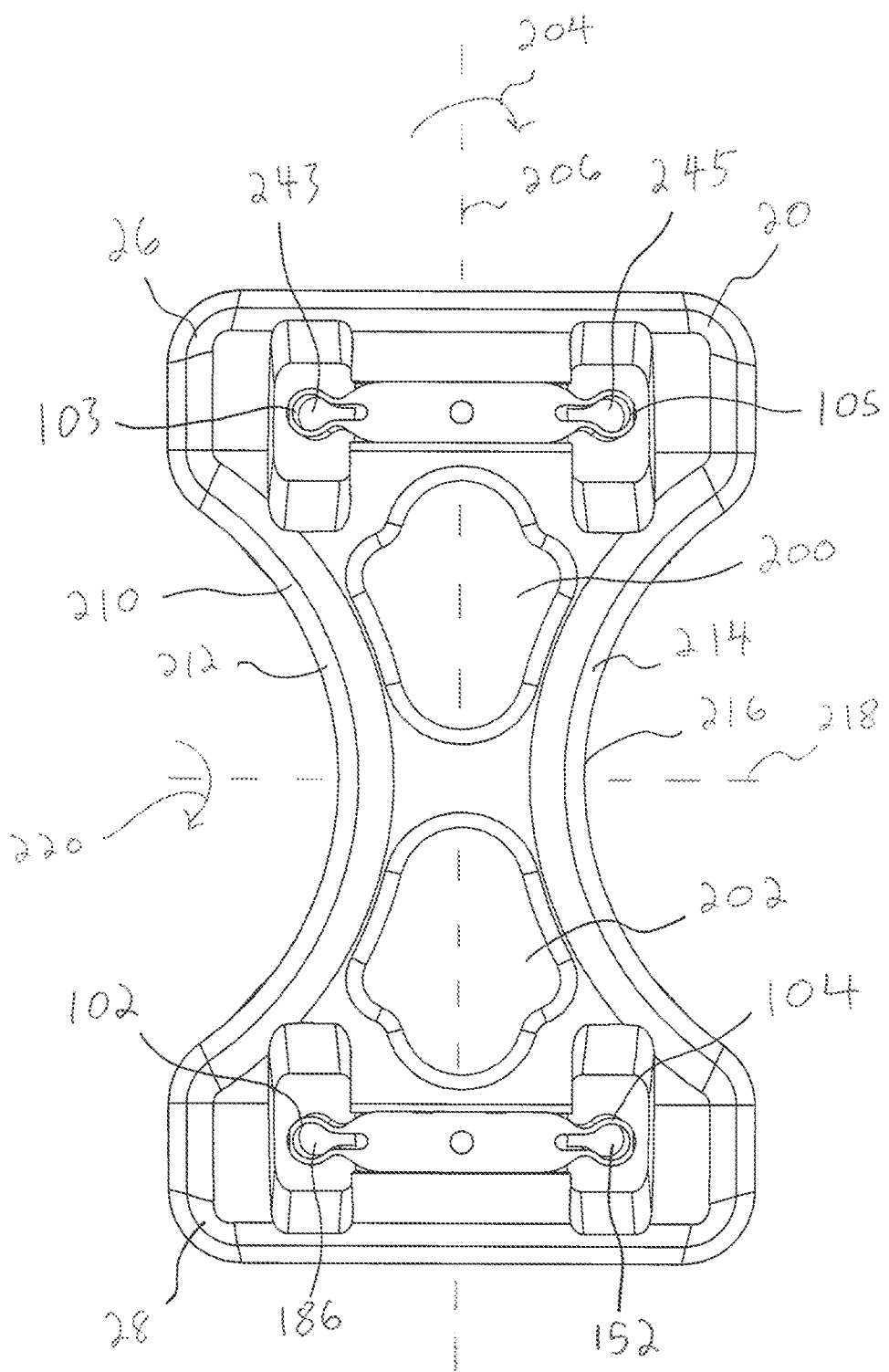
FIG. 6 is a plan view of the bone plate of FIG. 1 showing a tapered midsection of the bone plate.
Figure 7:
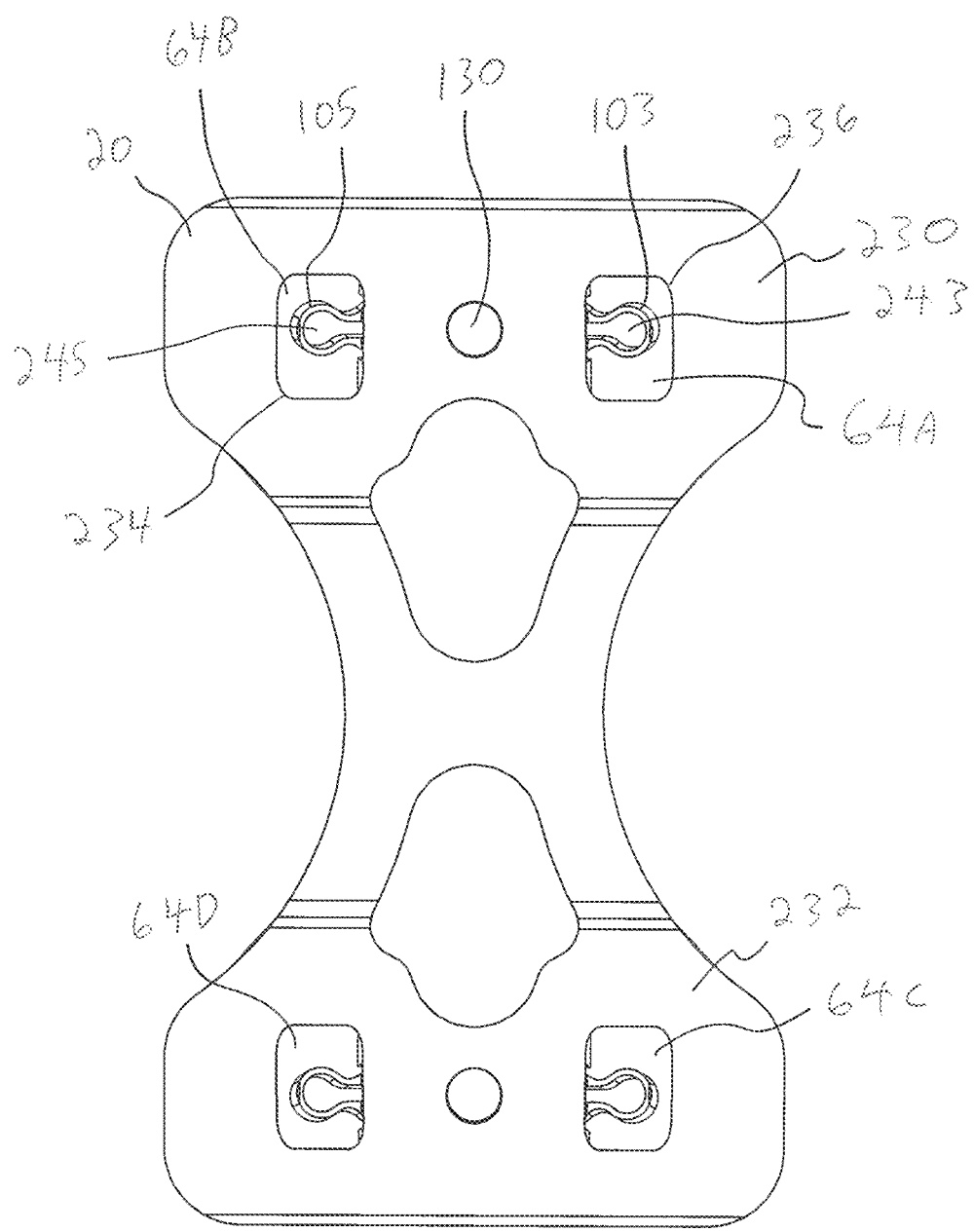
FIG. 7 is a bottom plan view of the bone plate of FIG. 1 showing seating surfaces of the bone plate which engage against the ribs and openings in the seating surfaces that are aligned with the heads of the crimp members.
Figure 8:
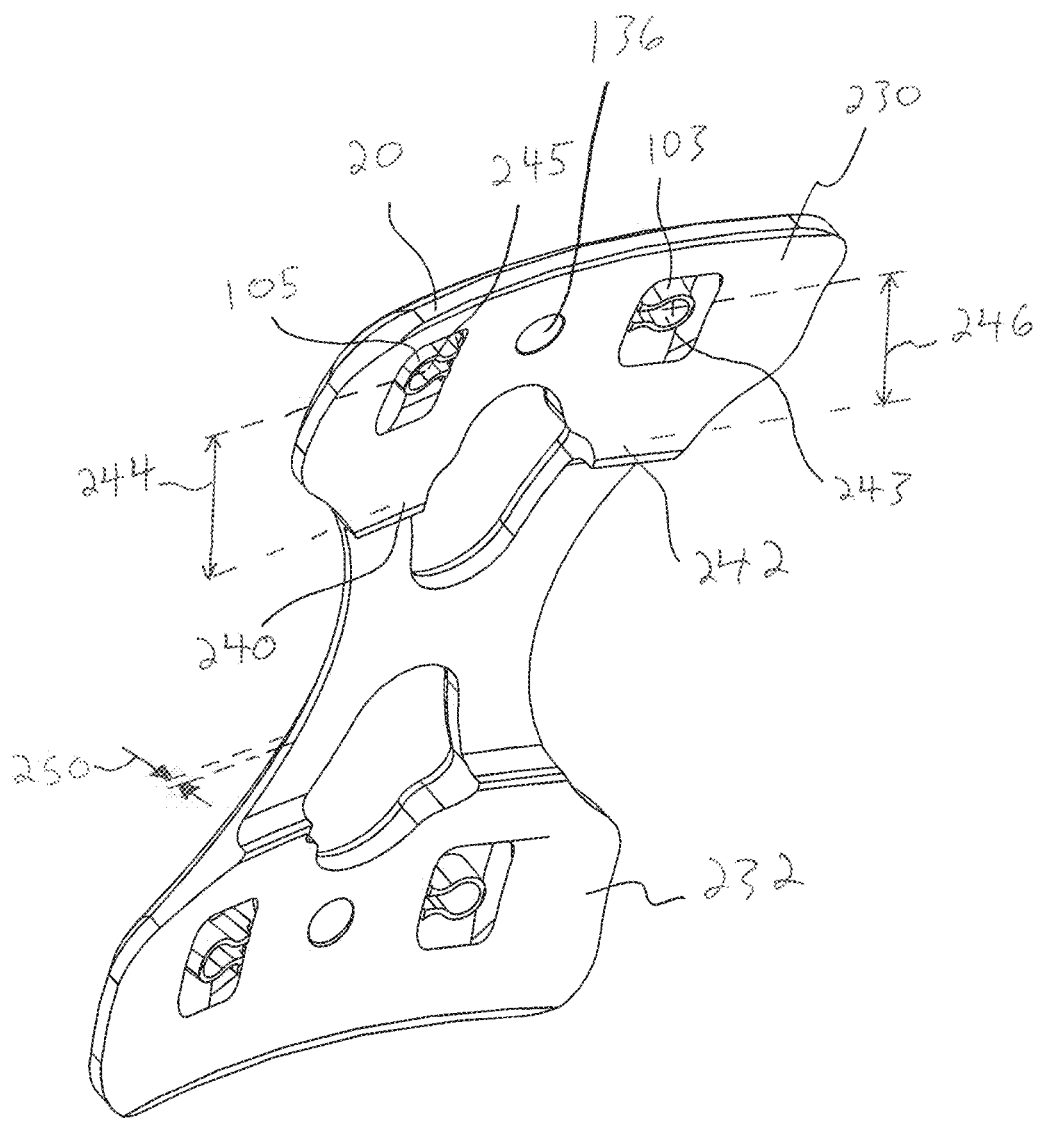
FIG. 8 is a perspective view of the bone plate of FIG. 1 showing raised lips of the seating surfaces that compliment curved outer surfaces of the ribs.

With reference to FIGS. 6-8, the bone plate 20 has a number of features which increase the flexibility of the bone plate to accommodate post-operative shifting of the ribs 12, 14, such as the movement that occurs with breathing or coughing. For example, the bone plate 20 may be made of polyether ether ketone (PEEK) such that the bone plate 20 has sufficient rigidity to stabilize the rib portion 18 while still permitting a predetermined amount movement of the rib portion 18 relative to the rib 12. Further, the bone plate 20 may have windows 200, 202 that reduce the rigidity of the bone plate 20 and serve a secondary function of permitting a surgeon to view the ribs 12, 14 or other anatomy below the bone plate 20. As shown in FIG. 6, the bone plate 20 may also have a dog bone shape with enlarged ends 26, 28 and a tapered midsection 210 with arcuate sidewalls 212, 214 that converge towards one another and form a waist 216 at a center line 218 of the bone plate 20. The windows 200, 202 and the tapered midsection 210 work in combination to increase the flexibility of the bone plate 20 to bending in direction 204 about a longitudinal axis 206 of the bone plate 20 and bending in direction 220 about the center line 218.

With reference to FIGS. 7 and 8, the bone plate 20 has structures that are configured to aid positioning of the bone plate 20 along the ribs 12, 14. For example, the bone plate 20 may have concave seating surfaces 230, 232 that closely conform to curved outer surfaces 217, 219 of the ribs 12, 14 (see FIG. 1). As shown in FIG. 7, the seating surfaces 230, 232 have openings 234, 236 that open into the through openings 64A-64D and permit passage of the leading end portions 72 of the surgical cables 40, 42, 44, 46 from within the holes 70A-70D in the ribs 12, 14 into the heads 102, 104 and 103, 105 of the crimp members 100, 101. With reference to FIG. 8, the bone plate 20 has raised lips 240, 242 that closely conform to the curved outer surfaces 217, 219 of the ribs 12, 14. The bone plate 20 and the crimp member 101 are configured to position apertures 243, 245 of the crimp member 101 predetermined distances 244, 246 away from the lips 240, 242. The distances 244, 246 are selected such that when the lips 240, 242 are seated against the curved outer surfaces 217, 219 of the ribs 12, 14, the apertures 243, 245 of the crimp member 101 are aligned with a midline 410 of the rib 12 and away from a neurovascular bundle 91 of the rib 12 (see FIG. 15).

Figure 9:
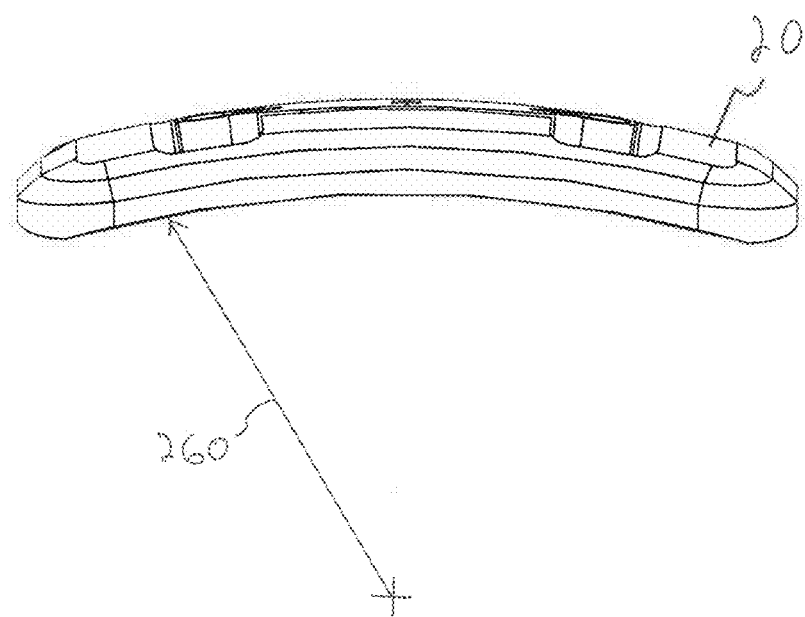
FIG. 9 is an end elevational view of the bone plate of FIG. 1 showing a lateral curvature of the bone plate.
Figure 10:
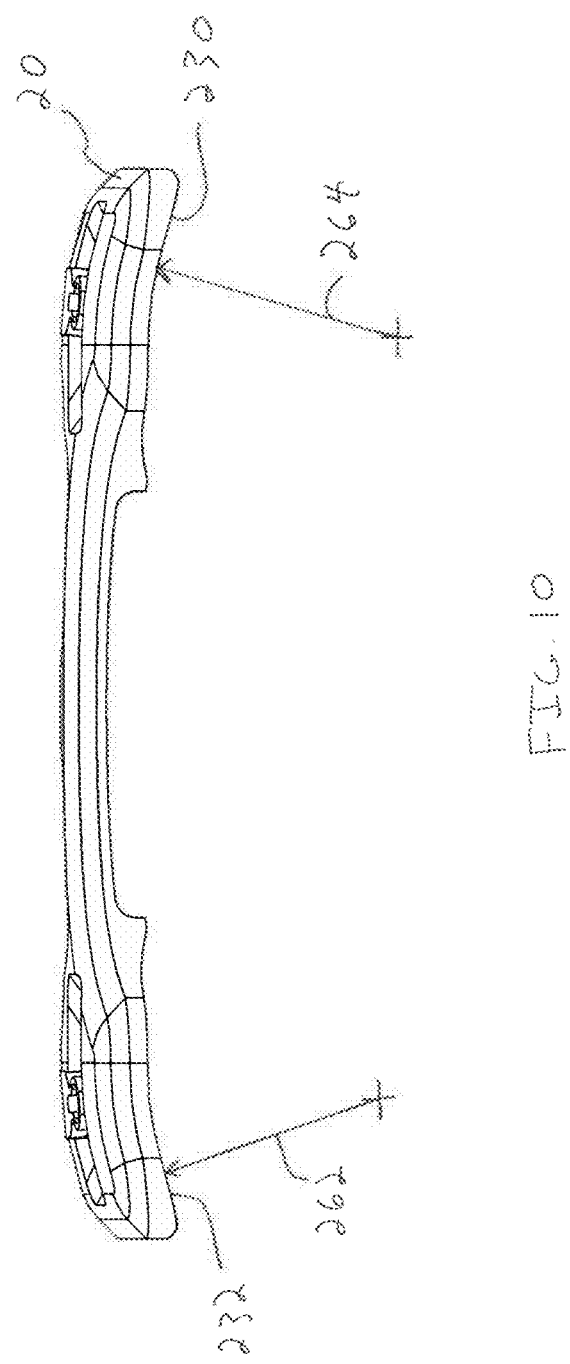
FIG. 10 is a side elevational view of the bone plate of FIG. 1 showing the curvature of the seating surfaces of the bone plate.

The ribs 12, 14 have a curvature along their lengths as well as the curvature of surfaces 217, 219 that are generally transverse to the lengths of the ribs 12, 14. To conform to these curvatures, the bone plate 20 has a curvature with a radius 260 selected to conform to the curvature of the ribs 12, 14 along the length thereof, as shown in FIG. 9. With reference to FIG. 10, the seating surfaces 230, 232 may also have curvatures with radii 262, 264 selected to conform to the curved outer surfaces 217, 219 of the ribs 12, 14.

Figure 11:
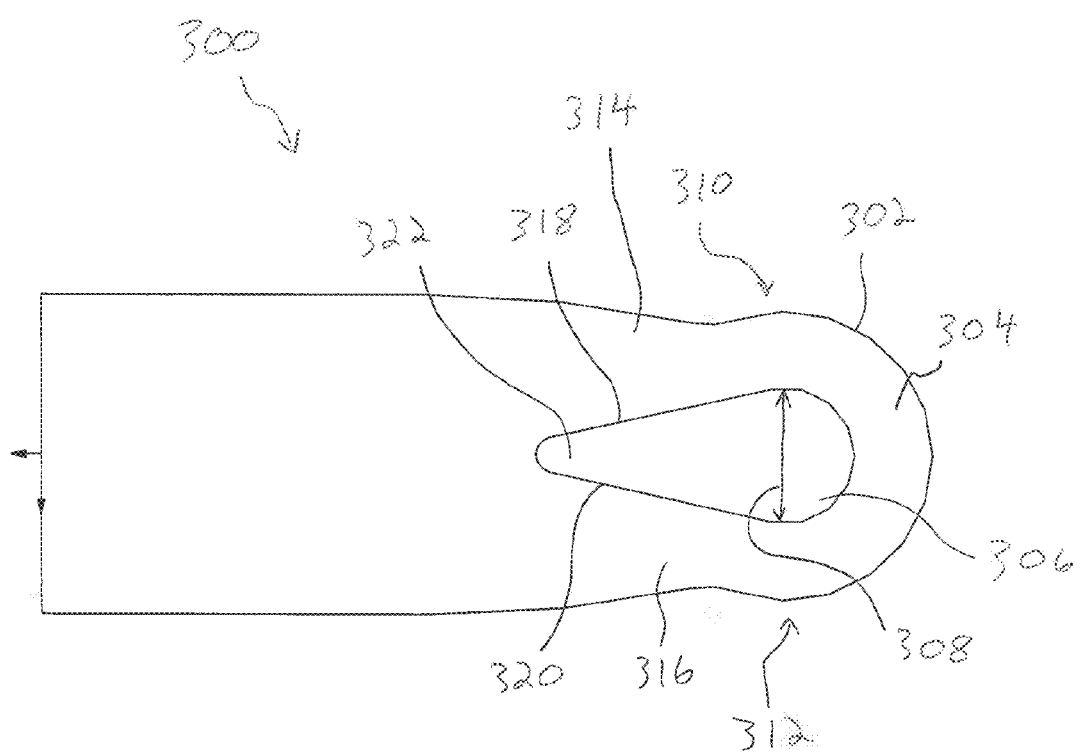
FIG. 11 is a perspective view of another crimp member showing a generally thicker head and a differently shaped aperture of the crimp member.

With reference to FIG. 11, one end of another crimp member 300 is shown. The crimp member 300 is similar to the crimp member 100 such that only the differences from the crimp member 100 will be discussed. The crimp member 300 has a larger head 302 and a thicker wall 304 thereof extending about an aperture 306 with approximately the same un-deformed diameter 308 as diameter 154 of the aperture 152 (see FIG. 5). The head 302 includes crimpable portions 310, 312 that have thicker arms 314, 316 than the arms 164, 166 of the crimpable portions 160, 162. The crimpable portions 310, 312 have walls 318, 320 with an acute angle therebetween which define a generally v-shaped gap 322 rather than the U-shaped gap 168 between the arms 164, 166. By utilizing thicker arms 314, 316 and angled walls 318, 320, crimping the crimpable portions 310, 312 causes substantially all of the arms 314, 316 to deform. Increasing the amount of the arms 314, 316 that deform reduces spring back of the arms 314, 316 after crimping of the crimpable portions 310, 312. Further, the thicker wall 304 of the head 302 undergoes plastic deformation with crimping of the crimpable portions 310, 312 and provides greater resistance to spring back of the arms 314, 316 once the head 302 has been crimped onto a surgical cable.

As noted above, the bone plate 20 may be made of PEEK. The surgical cables 40, 42, 44, 46, plugs 77, crimp members 100, 101, and the set pins 130 may be made of titanium, titanium alloy, series 316 stainless steel, or other suitable materials. The bone plate 20 may also be made of a surgical grade stainless steel, titanium, titanium alloy, cobalt chromium alloy, nitinol, or other biocompatible materials.

Figure 12:
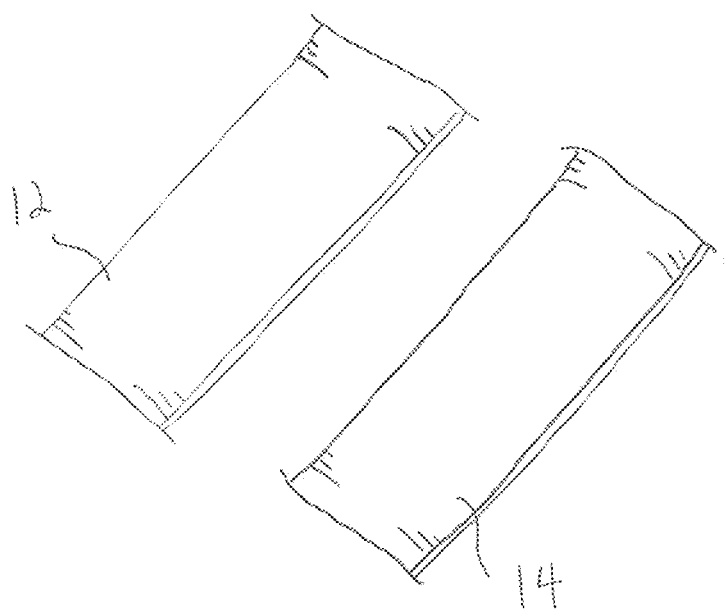
FIGS. 12-25 illustrate a method of approximating a pair of ribs using the bone plate system of FIG. 1 and tools for performing the method.
Figure 13:
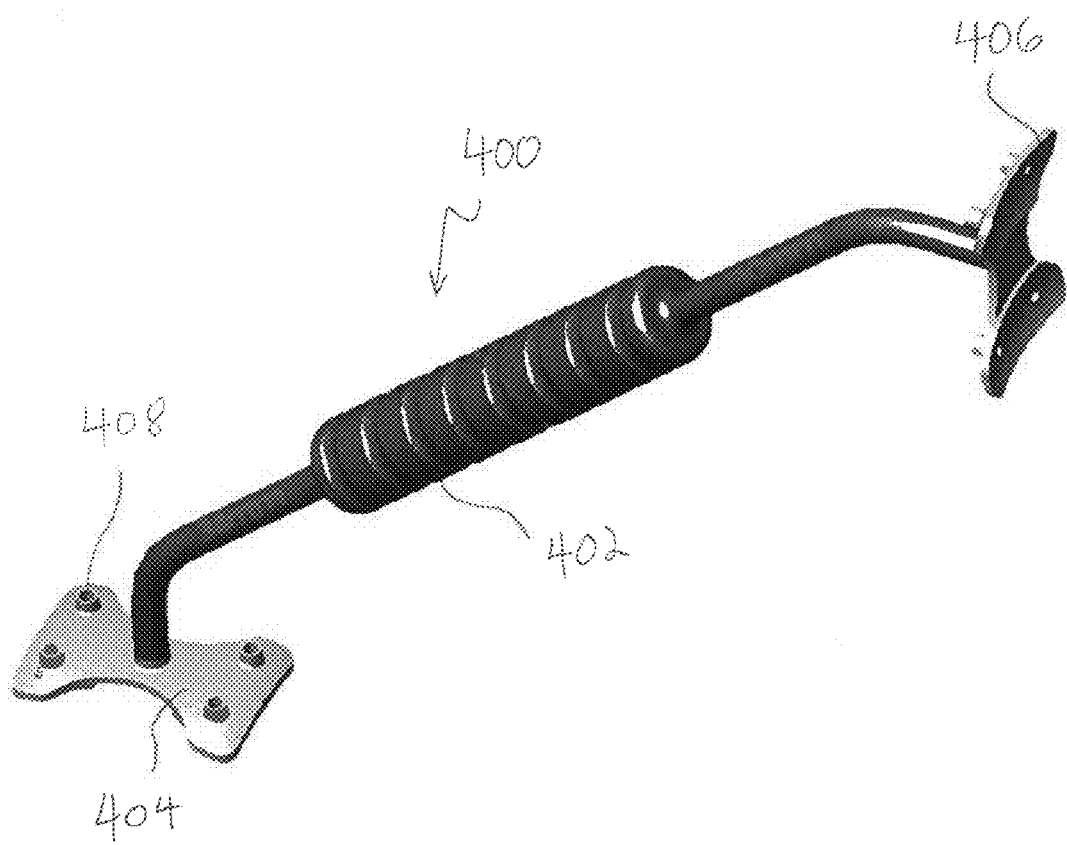

With reference to FIGS. 12-25, a method of approximating the ribs 12, 14 is shown. The ribs 12, 14 may have an original position prior to retraction during a thoracotomy procedure, as shown in FIG. 12. Before retracting the ribs 12, 14, a guide 400 is used to drill holes in the ribs 12, 14. The guide 400 has a handle 402 for manipulating the guide 400 and a plate template 404, 406 at either end of the guide 400. Each plate template 404, 406 has a number of openings 408 that are sized to receive a drill bit. The plate templates 404, 406 have different sizes and/or contours so that a surgeon can select one of the templates 404, 406 that best fits a patient's anatomy.

Figure 14:
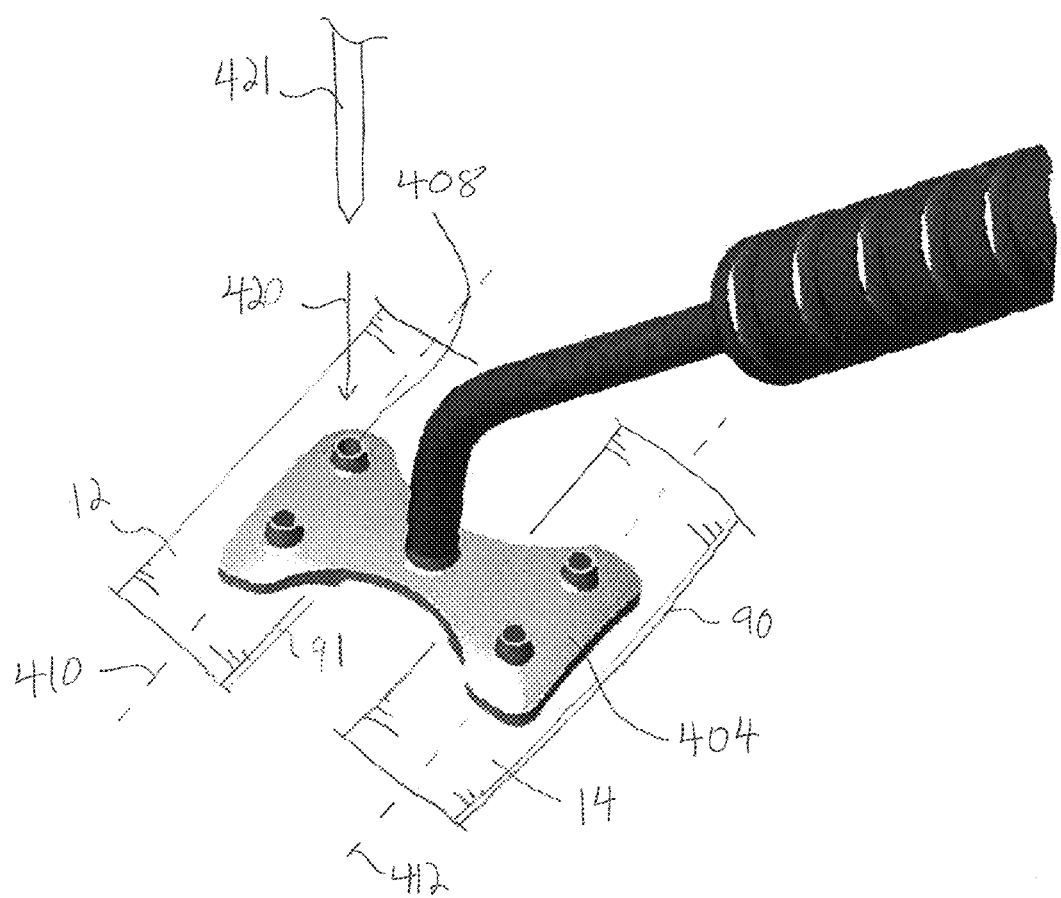
Figure 15:
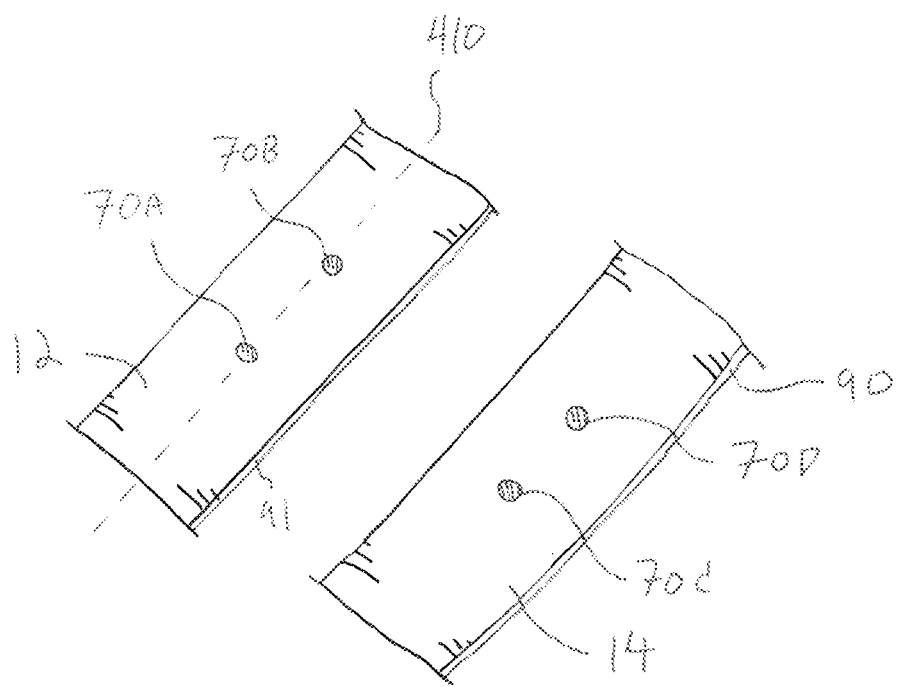

With reference to FIG. 14, the guide 400 is manipulated to position one of the plate templates 404, 406 against the ribs 12, 14. In FIG. 14, the plate template 404 is positioned against the ribs 12, 14 with the openings 408 of the template 404 positioned approximately over midlines 410, 412 of the ribs 12, 14. A drill bit 421 of a manual or electric drill is then advanced in direction 420 into each of the openings 408 to form the holes 70A-70D, as shown in FIG. 15. Positioning the openings 408 over the midlines 410, 412 allows the holes 70A-70D to be drilled in the thickest part of the ribs 12, 14 away from the neurovascular bundles 90, 91 of the ribs 12, 14. The guide 400 may then be removed from the ribs 12, 14.

Figure 16:
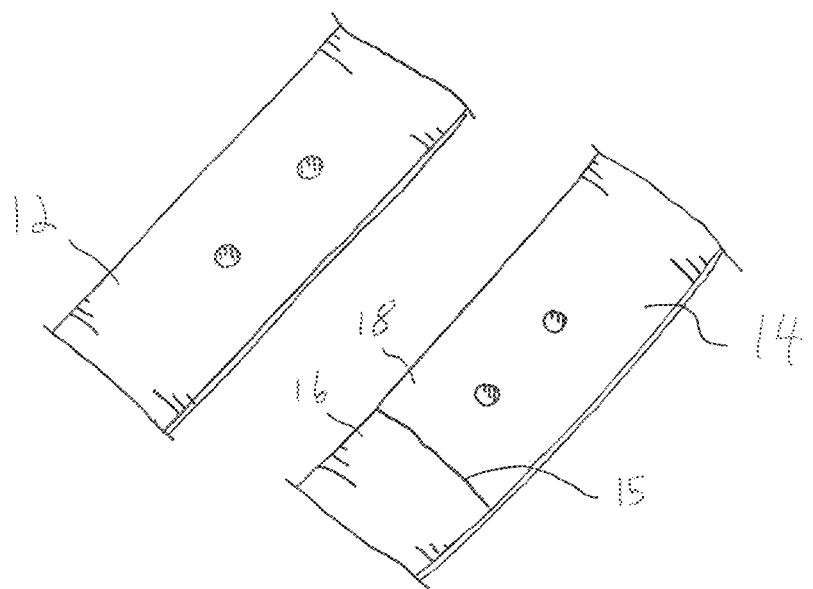

With the holes 70A-70D formed in the ribs 12, 14, the surgeon may cut 15 the rib 14 into the two rib portions 16, 18 as shown in FIG. 16. Drilling the holes 70A-70D prior to cutting 15 of the rib 14 improves the alignment and fusion of the rib portions 16, 18 after cutting 15. Further, drilling the holes 70A-70D prior to cutting 15 improves ease of drilling when compared to manipulating the loose rib portions 16, 18 after the rib 14 has been cut. As will be appreciated, the holes 70A-70D may be formed by a variety of approaches other than utilizing an electric drill.

After cutting 15 the rib 14 into portions 16, 18, the rib portion 18 may be retracted in direction 430 away from rib 12, as shown in FIG. 17. Retracting the rib portion 18 may improve access to the interior of the patient's chest cavity during the thoracotomy procedure. In an alternative approach, the rib 14 is not cut during the throracotomy procedure because retraction of the ribs 12, 14 provides surfficient access to the patient's chest cavity.

Figure 18:
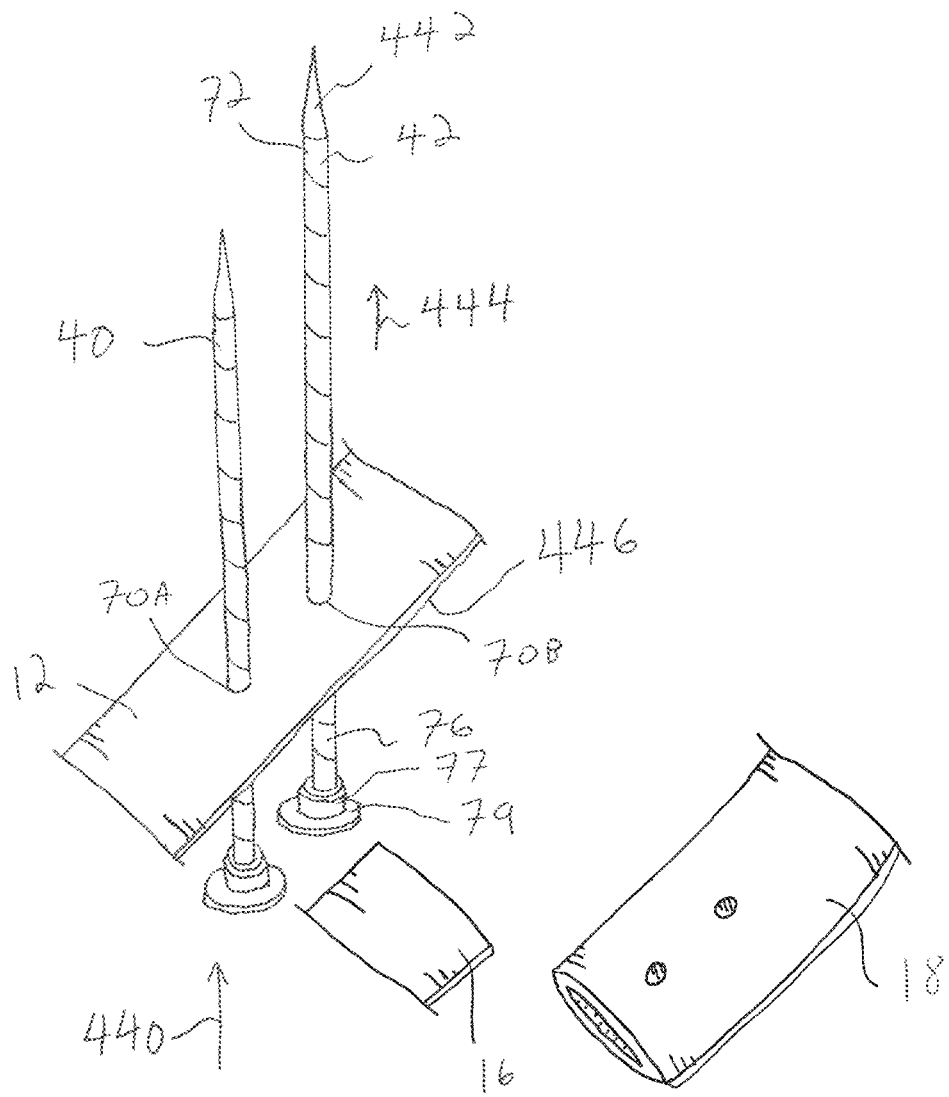
Figure 19:
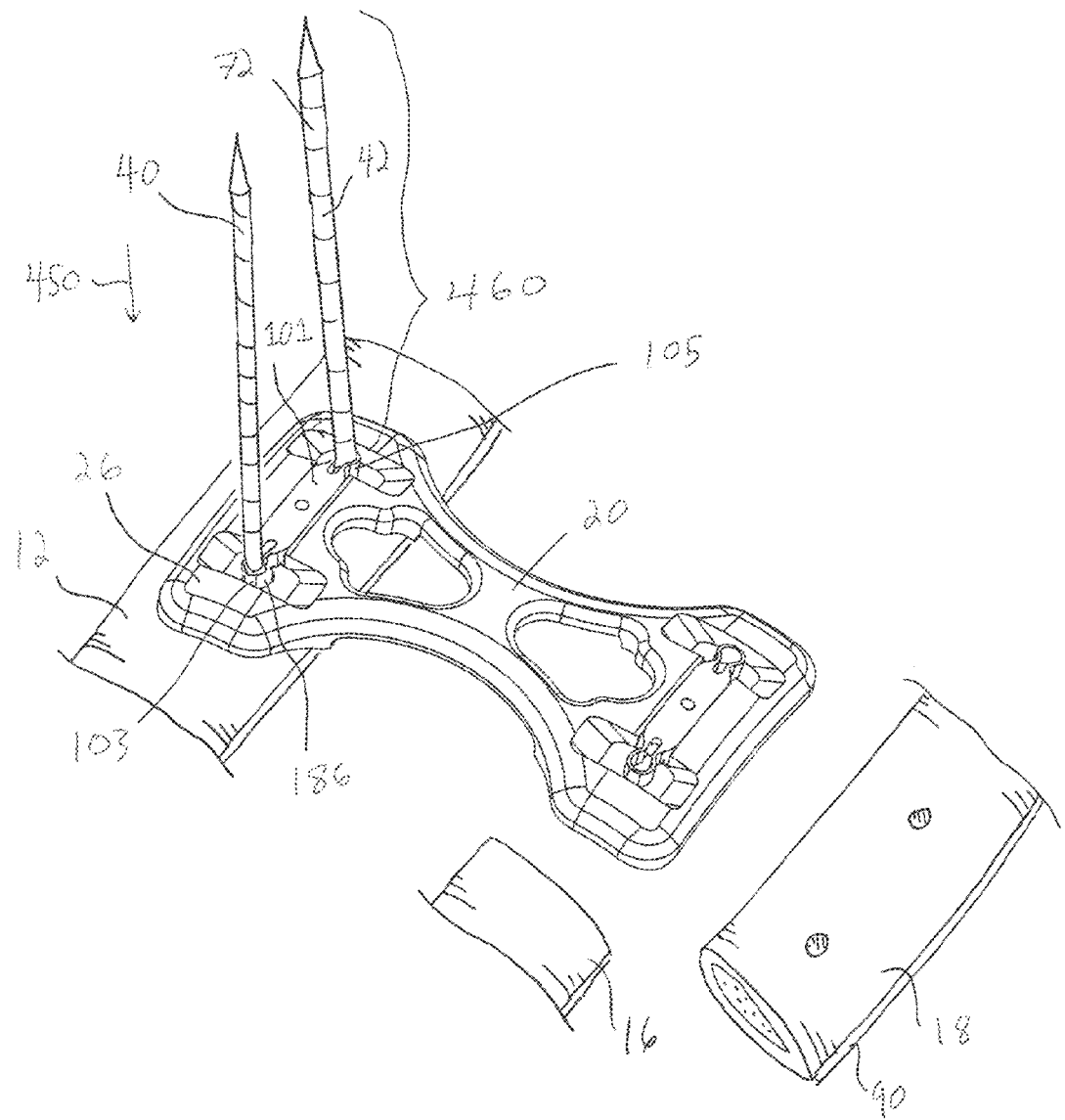
Figure 20:
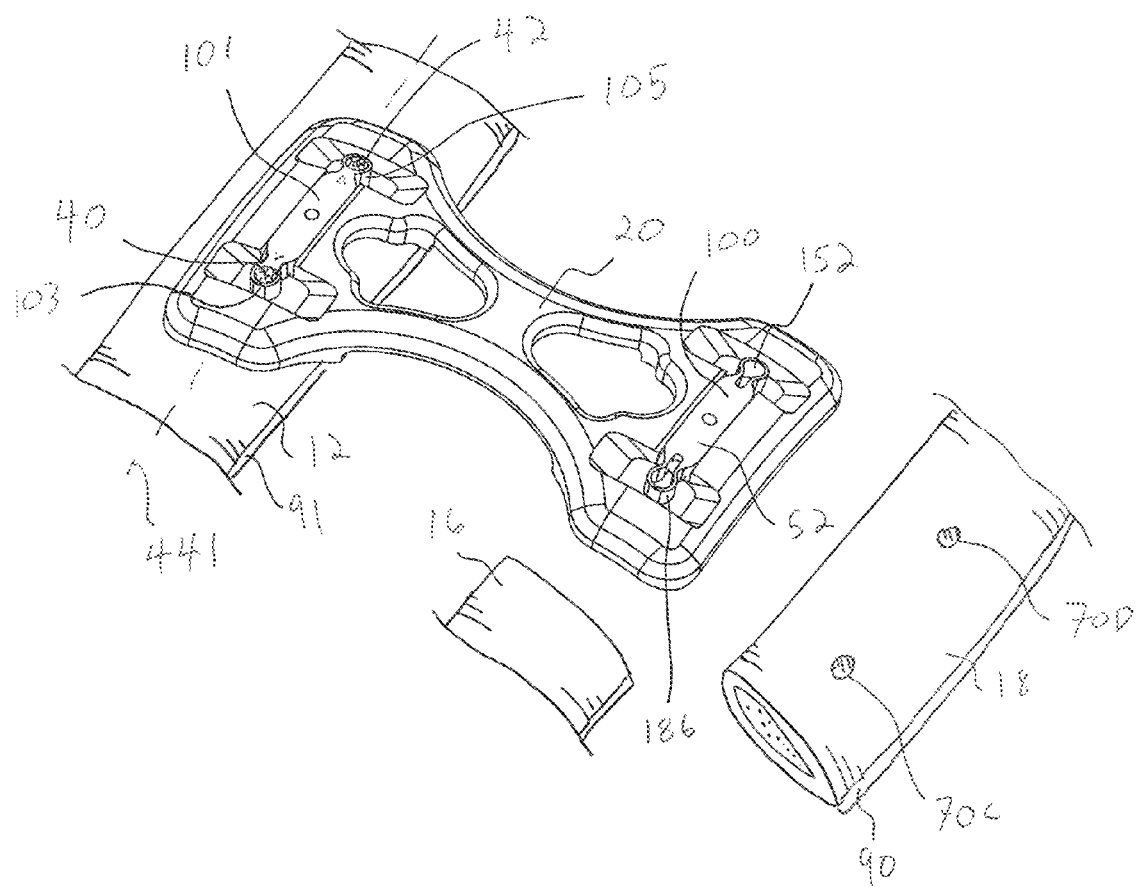

Once the tissues or organs within the chest cavity have been operated upon, the ribs 12, 14 may be approximated back toward the original position. With reference to FIG. 18, the leading end portions 72 of the surgical cables 40, 42 may have needles 442 to improve the ease with which the surgical cables 40, 42 may be maneuvered. Initially, the leading end portions 72 of the surgical cables 40, 42 are advanced from within the patient's chest cavity in direction 444 through holes 70A, 70B in the rib 12. The leading end portions 72 are pulled in direction 444 until the plugs 77 of the trailing end portions 76 engage an underside 446 of the rib 12 surrounding the holes 70A, 70B and the flanges 79 of the plugs 77 seat against the underside 446. The leading end portions 72 of the surgical cables 40, 42 are then advanced through openings 234, 236 of the bone plate seating surface 230 (see FIG. 7) and through the apertures 243, 245 of the heads 103, 105 of the crimp member 101. With the leading end portions 76 of the surgical cables 40, 42 threaded through the apertures 243, 245 of the crimp member 101, the bone plate 20 is moved downward in direction 450 which seats the bone plate end 26 against the rib 12, as shown in FIG. 19. The surgical cables 40, 42 may then be tensioned to draw the slack out of the surgical cables 40, 42 and pull portions 460 of the surgical cables 40, 42 beyond the bone plate 20. The heads 103, 105 of the crimp member 101 may then be crimped to fix the bone plate 20 to the surgical cables 40, 42, as shown in FIG. 19. The portions 460 of the surgical cables 40, 42 extending above the bone plate 20 may be cut and removed from the surgical site. At this point, the bone plate end 26 has been fixed to the rib 12 by crimping the heads 103, 105 of the crimp member 101 to the surgical cables 40, 42 and the excess length portions 460 of the surgical cables 40, 42 have been removed, as shown in FIG. 20.

Next, the leading end portions 72 of the surgical cables 44, 46 are advanced through holes 70C, 70D in the rib portion 18 and through the apertures 152, 186 of the crimp member 100. The leading end portions 72 of the surgical cables 44, 46 are then advanced in direction 470 away from the bone plate 20 to remove slack from the surgical cables 44, 46. To connect the trailing end portions 76 of the surgical cables 44, 46 to the rib portion 18, the leading end portions 72 of the surgical cables 44, 46 are further advanced in direction 470 which engages the plugs 77 thereof with the cortical bone 75 surrounding the holes 70C, 70D and seats the flanges 79 of the plugs 77 against the underside 78 of the rib portion 18 (see FIG. 2). In one approach, the plugs 77 may be manually aligned with the holes 70C, 70D and/or pushed into the holes 70C, 70D in order to facilitate connection of the trailing end portions 74 to the rib portions 18.

Figure 21:
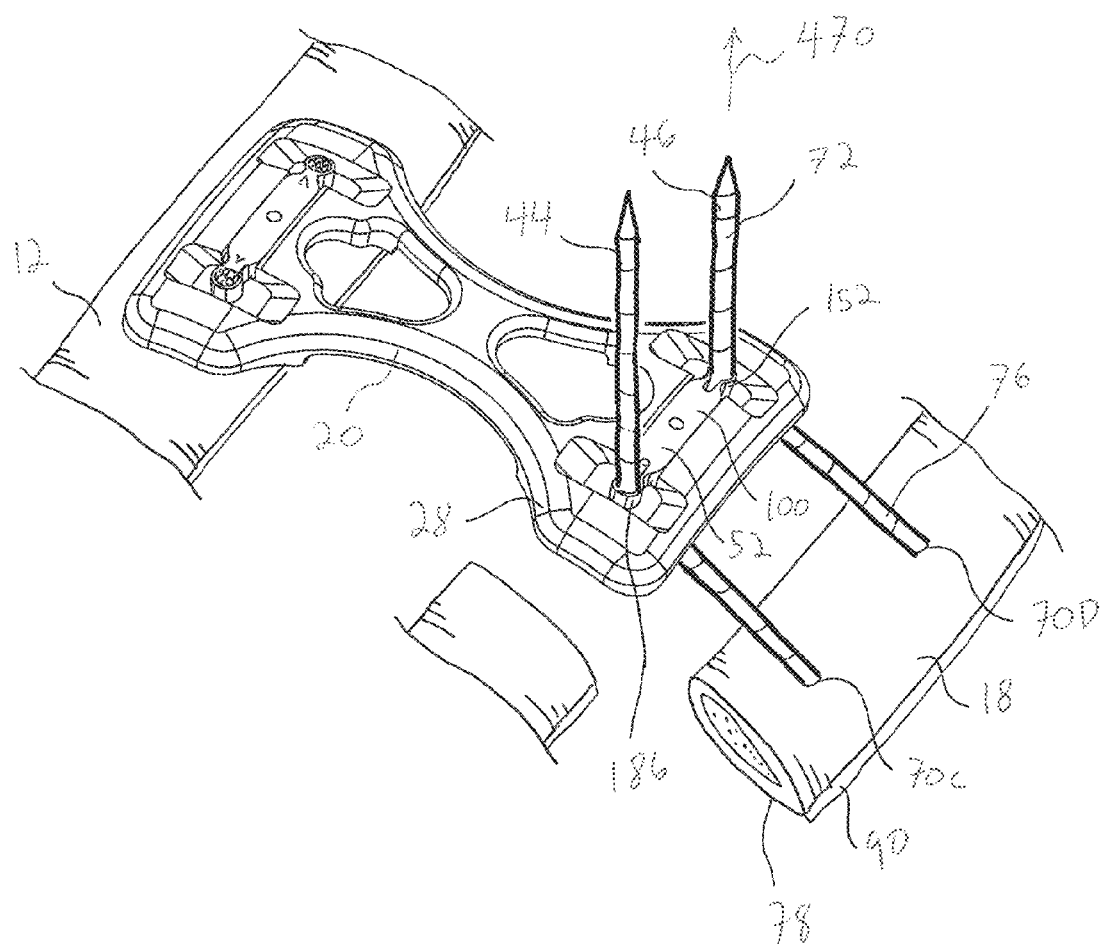
Figure 22:
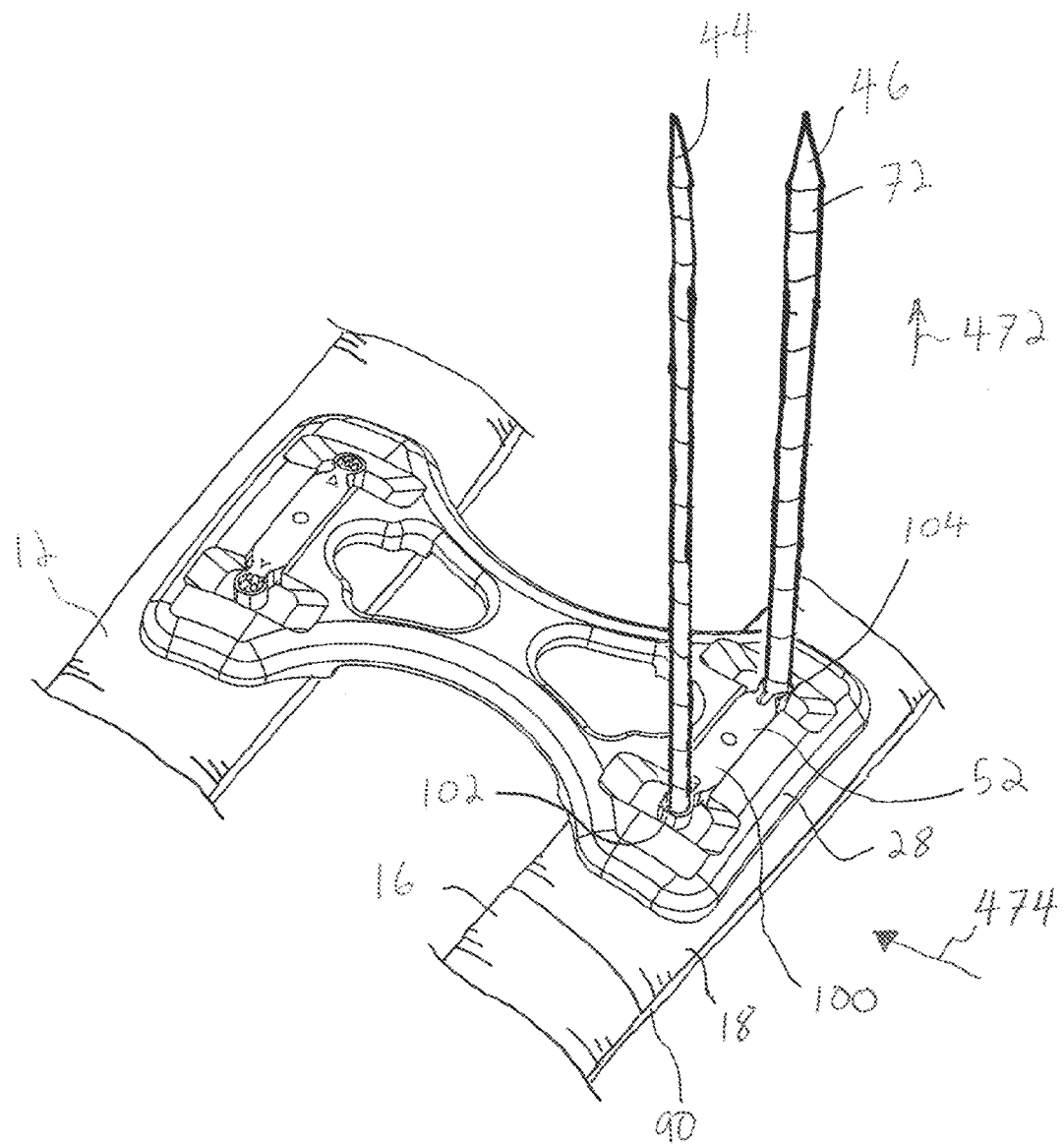

With the trailing end portions 76 of the surgical cables 44, 46 connected to the rib portion 18, as shown in FIG. 21, the leading end portions 72 of the surgical cables 44, 46 are pulled in direction 472 which tensions the surgical cables 44, 46 and pulls the rib portion 18 in direction 474 toward the rib 12. The heads 102, 104 of the crimp member 101 act as pulleys to redirect tension forces applied to the surgical cables in direction 472 into direction 474 to draw the rib portion 18 closer to the rib 12. The leading end portions 72 are pulled upward in direction 472 until the rib portion 18 is positioned and aligned with the bone plate end 28, as shown in FIG. 22. In this manner, the bone plate system 10 may be used to quickly and easily approximate the ribs 12, 14 without the use of forceps or other devices.

With reference to FIGS. 23, 24, and 24A the crimping tool 500 may be used to crimp the heads 102, 104 and 103, 105 of the crimp members 100, 101 and fix the crimp members 100, 101 to the surgical cables 40, 42 and 44, 46. More specifically, the crimping tool 500 has a pair of jaws 502, 504 that may be shifted from an open position to a closed crimped position by bringing a trigger 506 of the crimping tool toward a handle 508 thereof.

FIG. 24A is a cross-sectional view taken across line 25-25 in FIG. 24 to show the position of the jaws 502, 504 when the jaws 502, 504 are aligned with the crimpable portions 160, 162. The head 102 is then crimped onto the surgical cable 46 by shifting the jaws 502, 504 together in directions 510, 512. The crimpable portions 160, 162 have an identical outer taper which matches the outer taper of the crimpable portions 180, 182 of the head 102 (see FIG. 5). In this manner, the crimping tool 500 may be used to crimp the head 104 and then moved laterally to the head 102 and used to crimp the crimpable portions 180, 182 without rotating the tool 500 about a longitudinal axis 520 thereof. This improves the speed and ease of use of the crimping tool and bone plate system 10.

Figure 26:
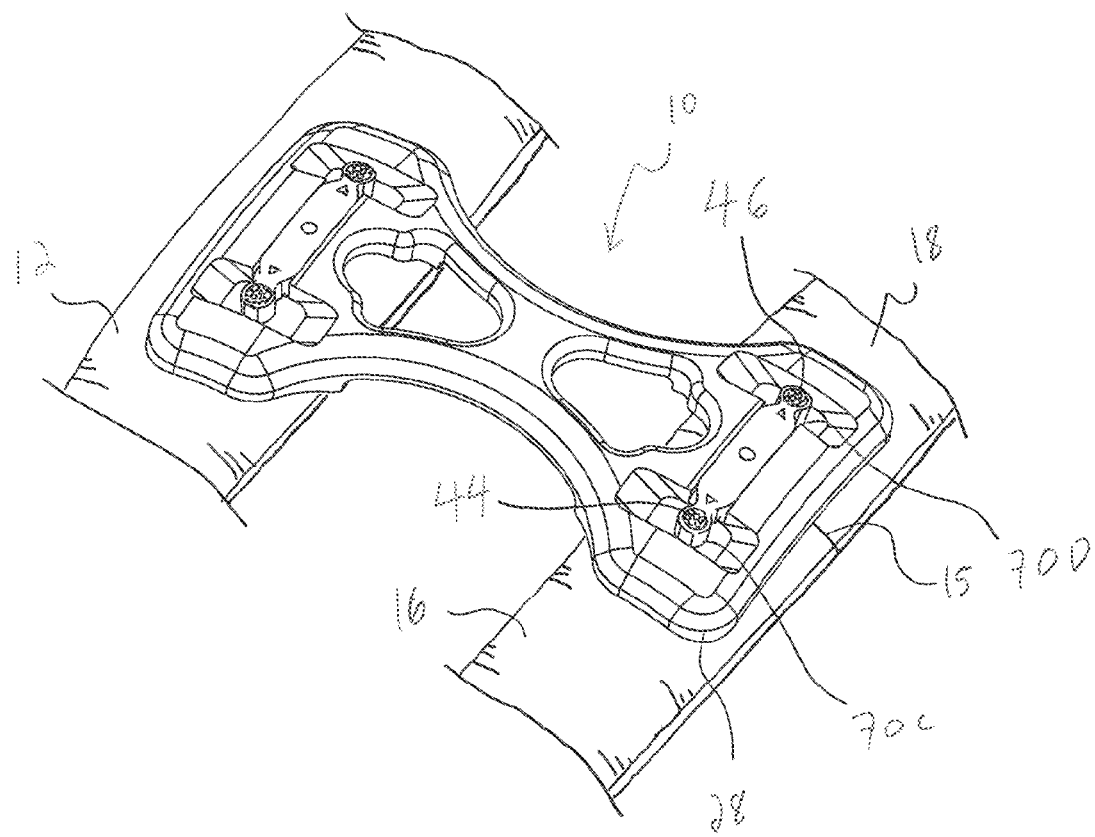
FIG. 26 is a perspective view of the bone plate system of FIG. 1 showing an alternative application of the bone plate system wherein one end of the bone plate extends across a cut in one of the ribs.

An alternative application of the bone plate system 10 is shown in FIG. 26. More specifically, rather than drill both holes 70C, 70D in rib portion 18, the holes 70C, 70D are drilled in the rib portions 16, 18 on opposite sides of the cut 15. When the bone plate end 28 is seated and fixed to the rib portions 16, 18, the bone plate end 28 extends across the cut 15. This approach may be used in the event that a higher level of fixation between the rib portions 16, 18 is desired.

In an alternative approach, more than one bone plate system 10 may be utilized to stabilize ribs 12, 14. The bone plate systems 10 may even be partially stacked on top of one another, e.g., the end 26 of one bone plate 10 could be positioned on a rib and an end 28 of another bone plate 20 could be stacked upon the end 26. In this approach, the through openings of 64C, 64D of the end 28 of the second bone plate 20 would be aligned with the through openings 64A, 64B of the end 26 of the first bone plate 20. Further, the crimp member 100 of the second bone plate 20 and the crimp member 101 of the first bone plate 20 would be fixed to the same surgical cables, e.g., surgical cables 40, 42.

Figure 27:
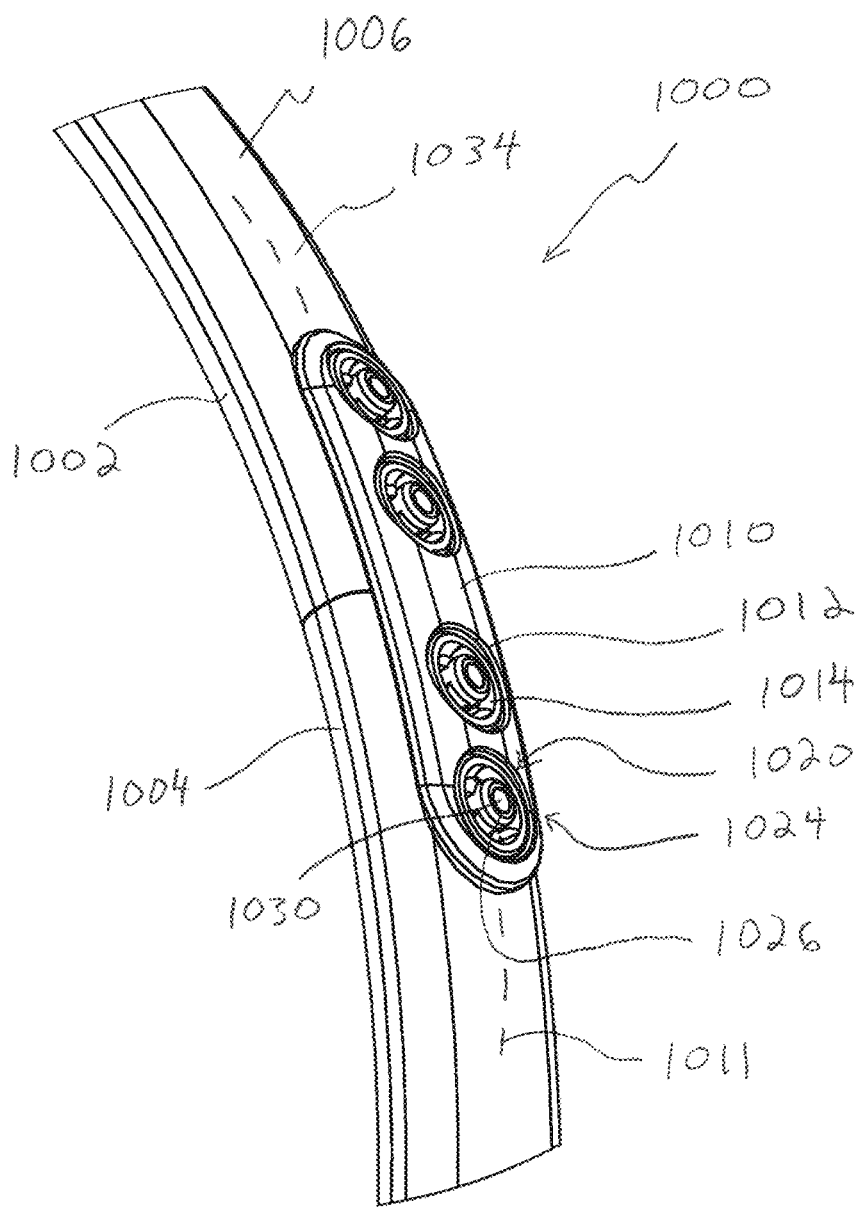
FIG. 27 is a perspective view of a bone plate system secured on a rib that has been cut into two portions.

With reference to FIGS. 27-33, a bone plate system 1000 is shown that may be used to stabilize one or more bones, such as portions 1002, 1004 of a cut rib 1006. The bone plate system 1000 is similar in many respects to the bone plate system 10 discussed above such that differences between the two will be highlighted. The bone plate system 1000 includes a bone plate 1010 that is well-suited for stabilizing a single rib 1006. With reference to FIGS. 1 and 27, the bone plate 1010 has a generally elongated, obround outer profile rather than the generally hourglass shape of the bone plate 20. The elongated, obround outer profile of the bone plate 1010 permits a longitudinal axis 1011 of the bone plate 1010 to be oriented generally parallel to the length of the rib 1006 and provides a relatively small footprint of the bone plate 1010 on the rib 1006 when the bone plate 1010 is secured to the rib 1006.

The bone plate 1010 has throughbores 1012 sized to receive locking devices such as crimps 1014 therein. The bone plate system 1000 has connector devices that may include cable portions, the connector device having opposite end portions of each of the cable connector devices with one end portion configured to abut against the bone adjacent a throughbore in the bone and the other end portion configured to be operatively fixed to the bone plate member with the cable portion extending therebetween. One example these connector devices are cables 1030, as shown in FIGS. 27 and 28.

Figure 28:
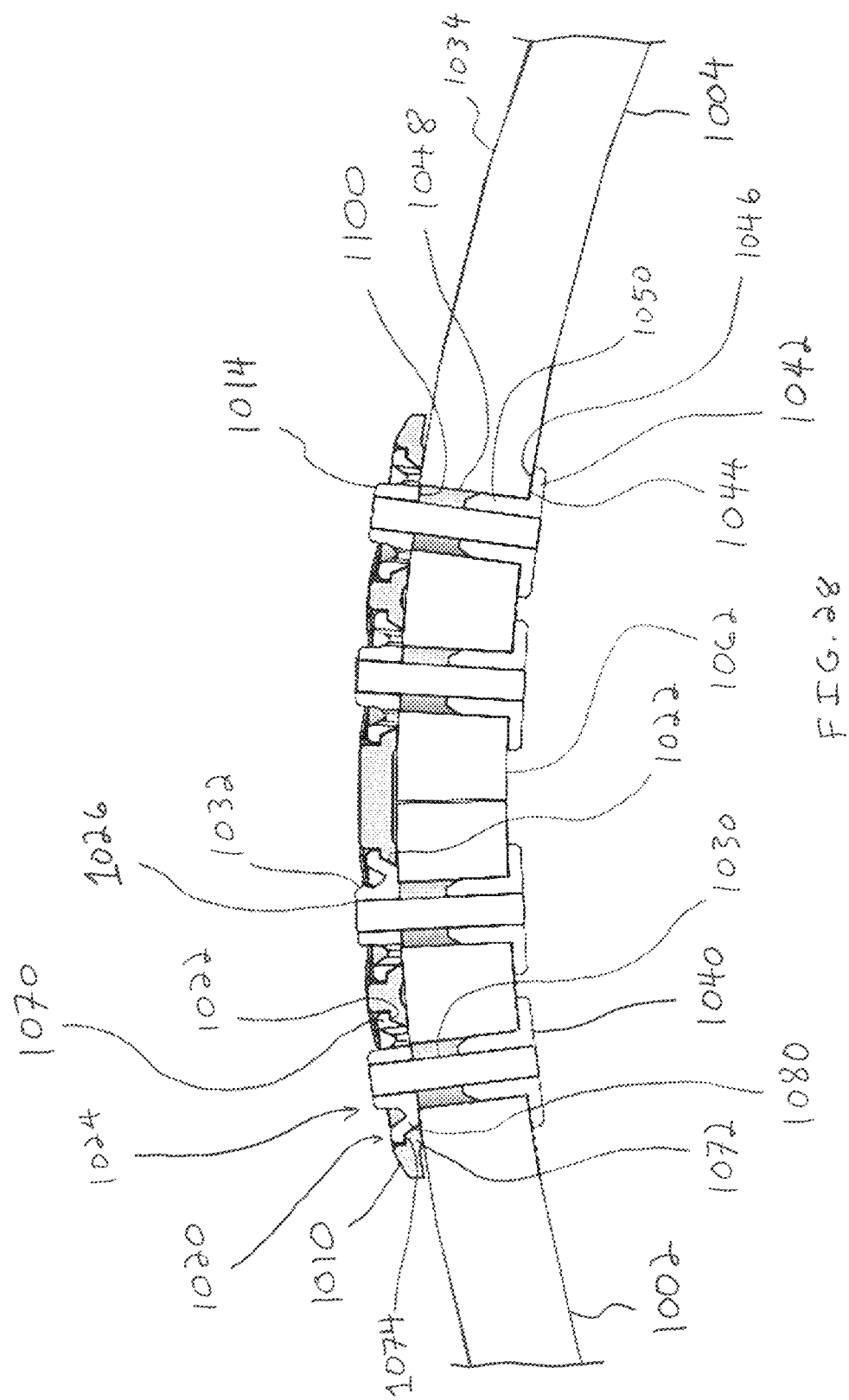
FIG. 28 is a cross-sectional view of the bone plate system of FIG. 27 showing cables of the bone plate system extending through holes in the ribs with one end of the cables secured to a bone plate with crimps and the other end of the cables secured to the rib with plugs.

The crimps 1014 have an outer portion 1020 configured to engage a rim 1022 extending about the throughbore 1012 and an inner portion 1024 having an aperture 1026 sized to receive the cable 1030 therethrough, as shown in FIGS. 27 and 28. The cables 1030 extend along passages, such as pre-drilled holes 1048, of the rib portions 1002, 1004 and are secured at their opposite ends to undersides 1062 of the rib portions 1002, 1004 by a stop member, such as a plug 1040.

Figure 29:
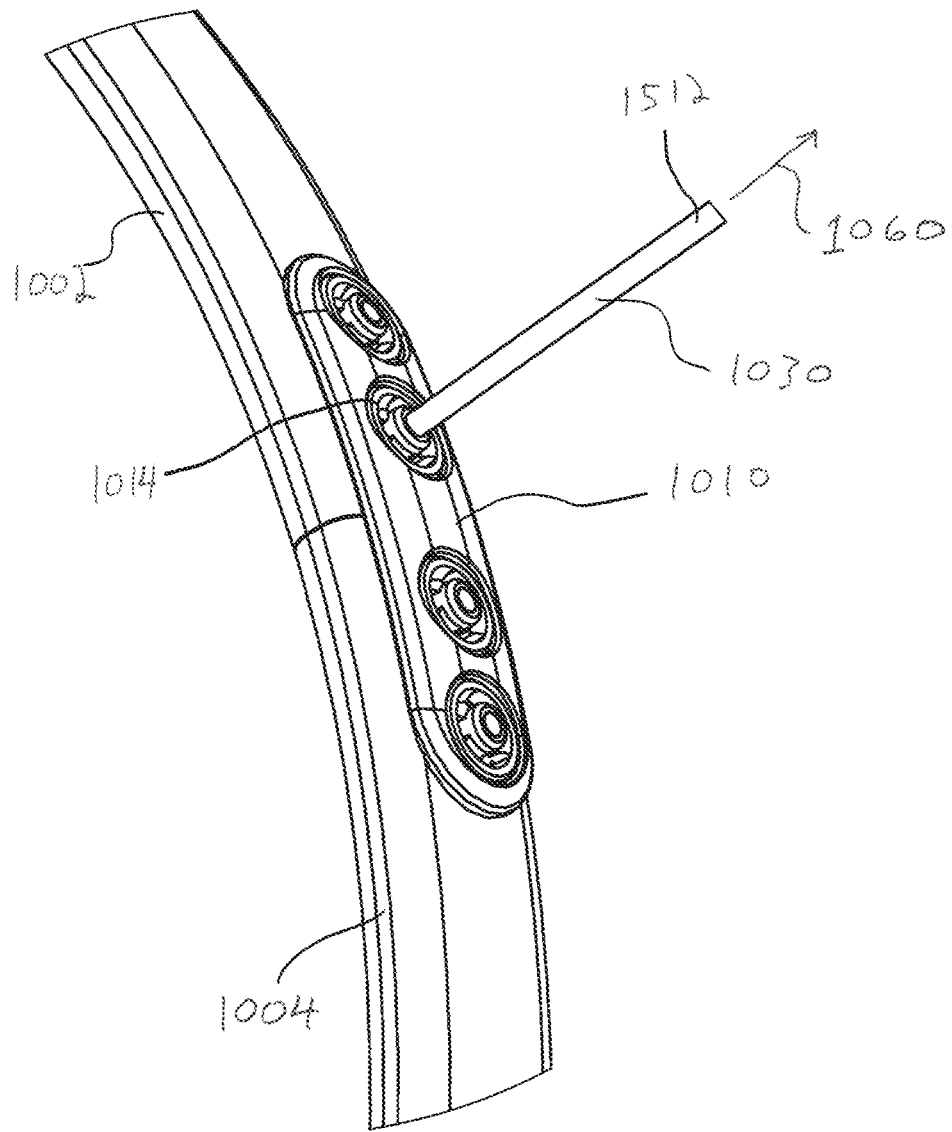
FIG. 29 is a perspective view of the bone plate of FIG. 27 showing a cable extending outward from a crimp before the cable is cut.

The crimp inner portion 1024 has a crimpable collar 1032 disposed about the aperture 1026 which may be crimped by a crimp tool 1500 (see FIG. 34) to fix the crimp 1014 and the bone plate 1010 engaged therewith to an outer surface 1034 of the rib 1006. At an opposite end of the cable 1030, the plug 1040 is connected to the cable 1030 such as by swaging, welding, adhesive, or other approaches. In alternative configurations, the stop member may include a knot tied in the cable 1030, a conical member swaged onto the cable 1030, and a bar member around which the cable 1030 is tied, for example. The plug 1040 has an engagement portion, such as a flange 1042, with an engagement surface 1044 configured to engage bone surfaces 1046 surrounding the respective hole 1048 in the rib 1006. In one form, the plug 1040 has a base 1050 sized to fit into the hole 1048 and secure the plug 1040 and cable 1030 against movement. As shown in FIGS. 28 and 29, the base 1050 may be press-fit into the hole 1048 by pulling a free end 1512 of the cable 1030 in direction 1060 to engage the plug 1040 with the rib 1006 before crimping the collar 1032 to the cable 1030, in a manner similar to the process described above with respect to plug 77.

With respect to FIGS. 30 and 31, the bone plate 1010 extends a short distance above an outer surface 1034 of the rib 1006 to provide a short profile of the bone plate 1010 on the rib outer surface 1034. Similarly, the plug flanges 1040 are generally even with or extend slightly above the underside surface 1062 of the rib 1006. In this manner, bone plate system 1000 has a low profile on both the outer and underside surfaces 1034, 1062 of the rib 1006.

Figure 32:
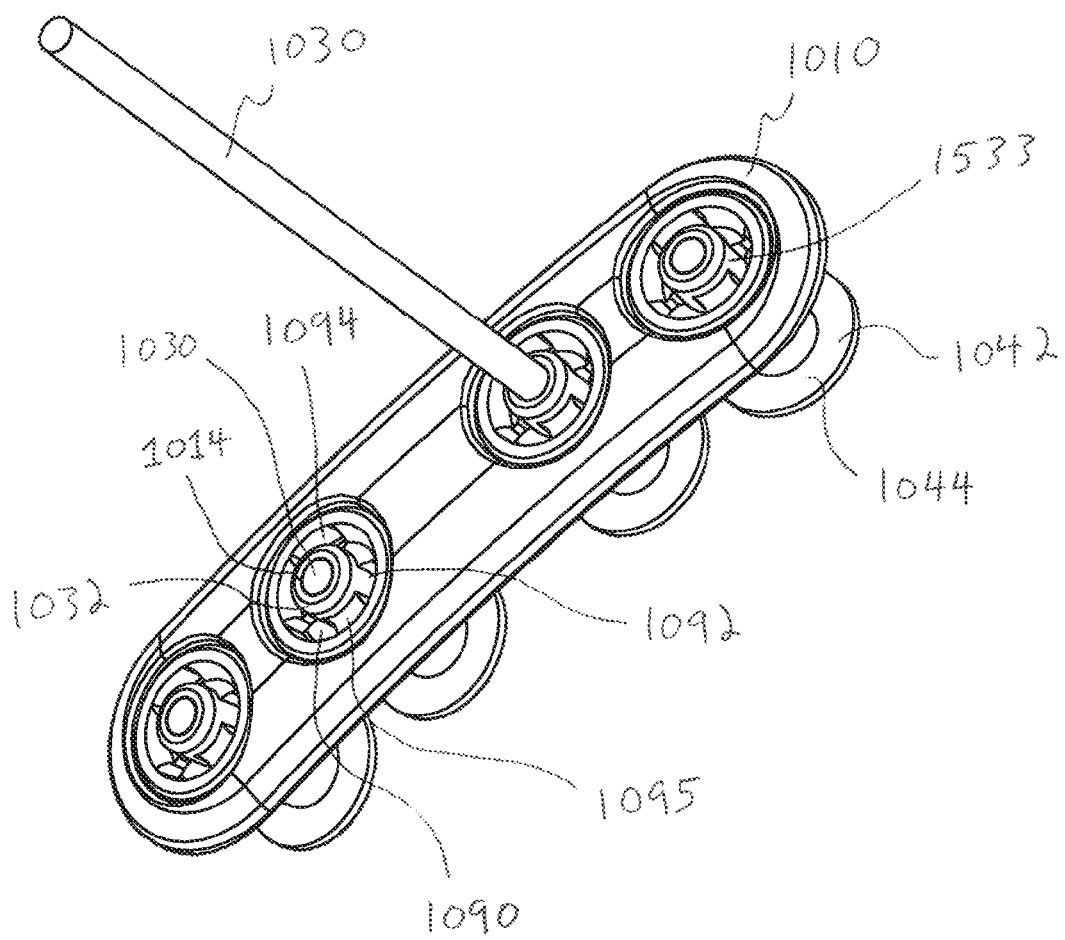
FIG. 32 is a perspective view of the bone plate system of FIG. 29 with the rib portions removed and showing the crimps of the bone plate system received within openings of the bone plate.

With respect to FIGS. 28 and 32, the crimps 1014 will be discussed in greater detail. The throughbore 1012 has a seat 1072 with an annular upper seating surface 1074 and a conical lower seating surface 1082. The crimp outer portion 1020 is configured to engage the seat 1072 and has a lip 1070 which seats against the upper seating surface 1072 to restrict pull-through of the crimp 1014. The crimp outer portion 1020 also has a tapered wall 1080 which engages the lower seating surface 1082 and centers the crimp 1014 within the throughbore 1012 as the crimp 1014 is pressed into the throughbore 1012. The crimp 1014 may have openings 1090, 1092, 1094 disposed circumferentially about the crimpable collar 1032, as shown in FIG. 32. The openings 1090, 1092, 1094 can be sized to receive portions of arms 1502 of the crimp tool 1500 (see FIGS. 35 and 37). The openings 1090, 1092, 1094 may also increase the flexibility of the crimp 1014 and define radially extending members 1095 which connect the tapered wall 1080 to the collar 1032. The radially extending members 1095 may be configured to engage the arms 1502 of the crimp tool 1500 and resist rotary movement of the crimp 1014 relative to the arms 1502.

Figure 33:
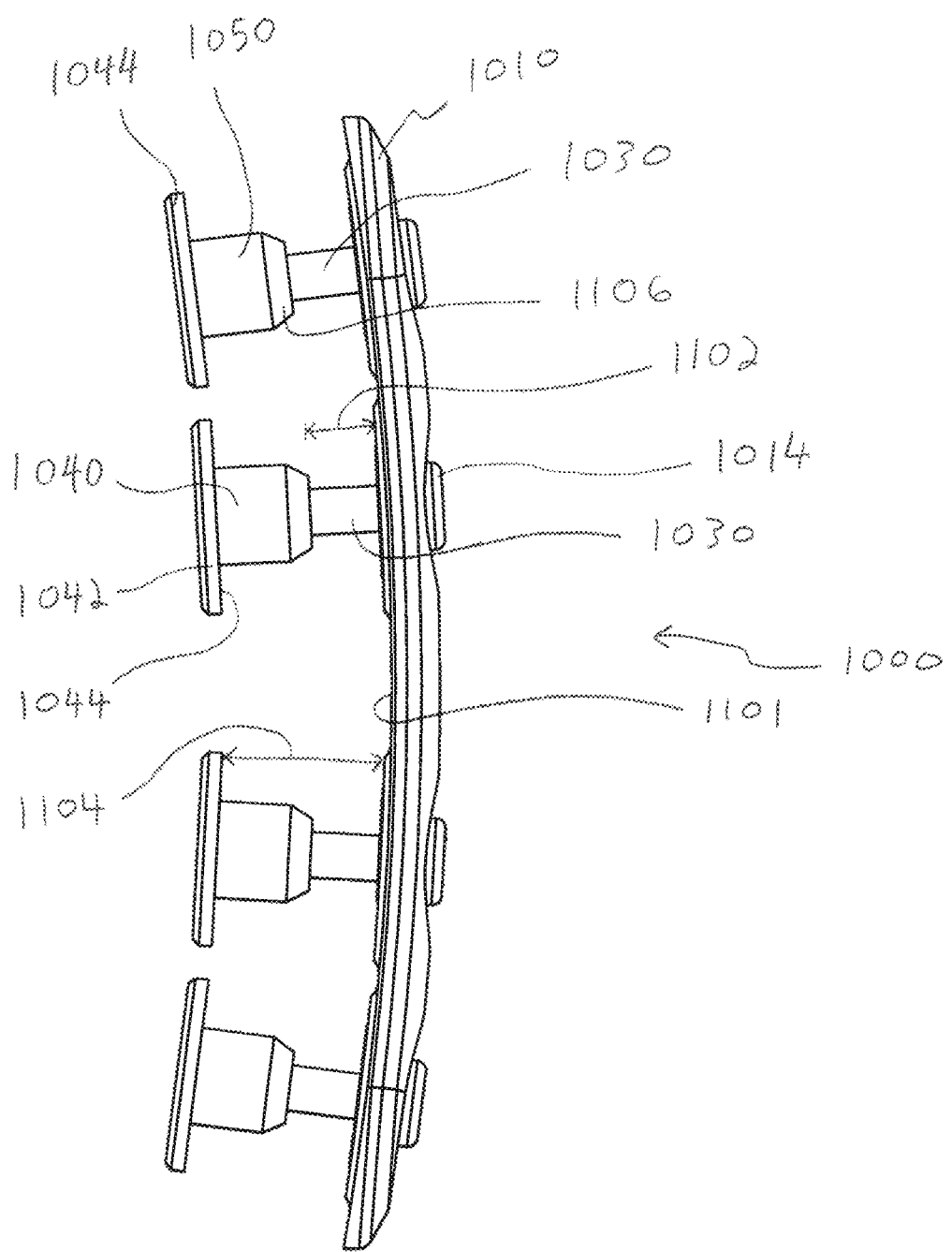
FIG. 33 is an elevational view of the bone plate system of FIG. 29 with the rib portions removed and showing the cables spacing the plugs from the bone plate.

With reference to FIG. 33, the bone plate system 1000 is shown partially installed with the rib 1006 removed for clarity. The cable 1030 of each crimp 1014 extends downward from a lower surface 1100 of the crimp 1014 (see FIG. 28) to separate the plug 1044 from a lower surface 1101 of the plate member 1010 by a distance 1102, as shown in FIG. 33. To facilitate placement of the plug 1040 within the bone hole 1048, the plug base 1050 has a tapered lead surface 1106 which centers the plug 1040 within the hole 1048 as tension is applied to the cable 1030.

Figure 51:
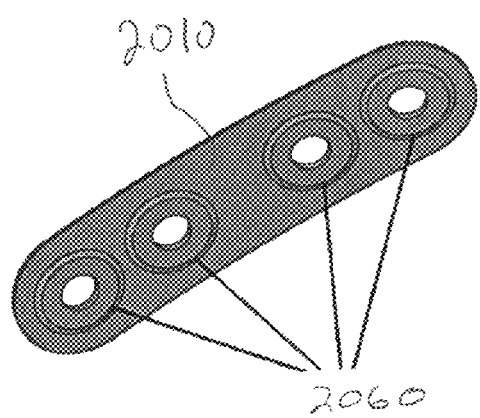
FIG. 51 is a perspective view of the bone plate of FIG. 44 showing raised feet of the lower surface of the bone plate.

The distance 1102 between the plug 1044 and the bone plate lower surface 1101 positions the engagement surface 1044 of the plug flange 1042 a distance 1104 away from the bone plate lower surface 1101. The distance 1104 may be slightly smaller than the thickness of the rib 1006 so that the plug flange 1042 and bone plate lower surface 1101 apply a compressive force against the rib portions 1002, 1004 and secures the plate member 1010 against movement away from the rib portions 1002, 1004. The frictional engagement of the bone plate lower surface 1101 and the rib outer surface 1034 restricts movement of the bone plate 1010 along the rib outer surface 1034. In one embodiment, the bone plate lower surface 1101 has pods 2060 (see FIG. 51) to reduce the contact area between the bone plate lower surface 1101 and rib outer surface 1034. This concentrates the engagement between the bone plate lower surface 1101 to regions of the bone surrounding the holes 1048.

The components of the bone plate system 1000 may be made of implant-grade polymers, metals, and alloys. For example, the bone plate 1010 may be made of PEEK. The crimps 1014, cables 1030, and plugs 1040 may be made of stainless steel.

Figure 35:
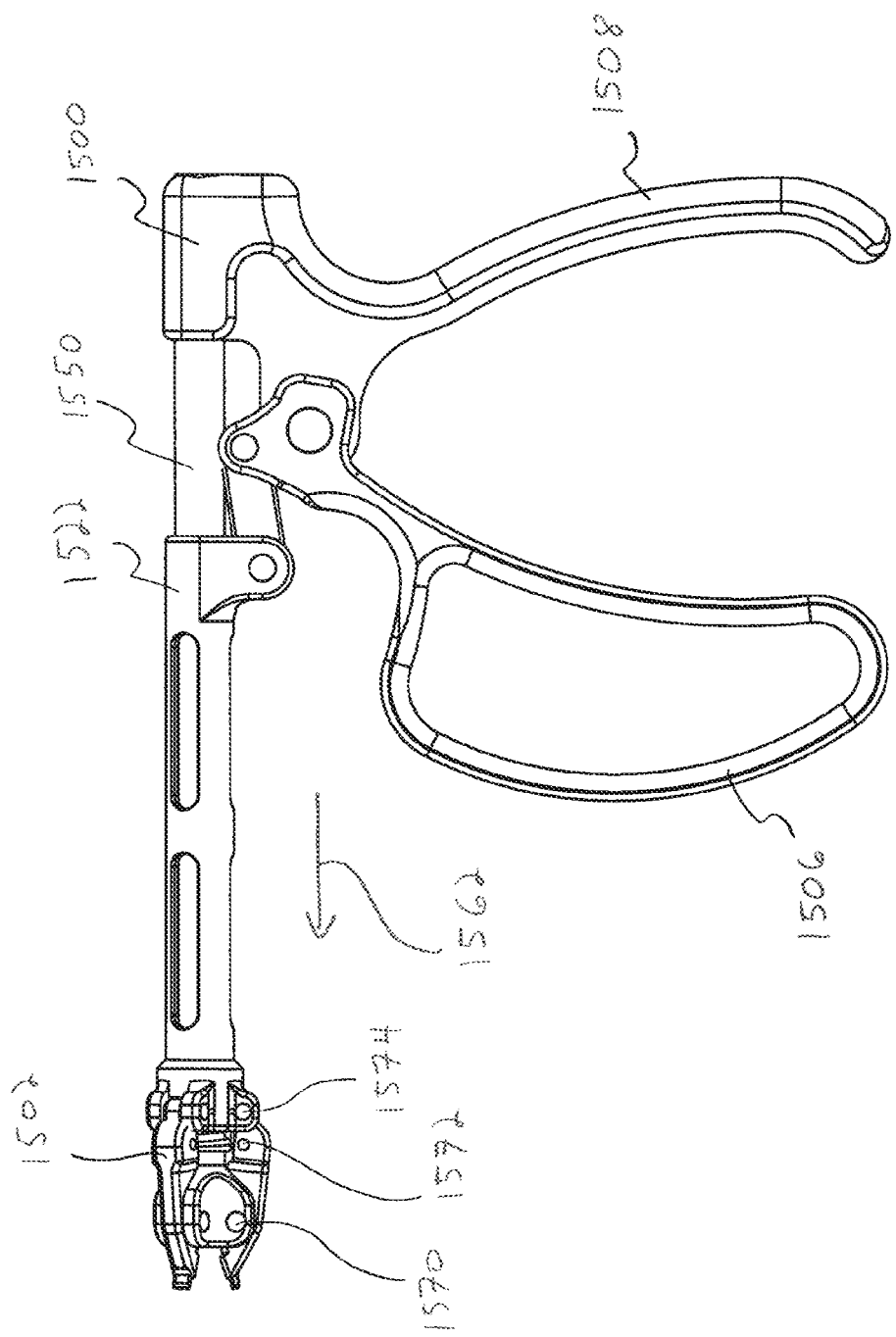
FIG. 35 is a side elevational view of the locking tool of FIG. 34 showing a locking lever of the tool moved away from a handle of the tool and locking arms at a distal end of the tool in an open configuration.
Figure 36:
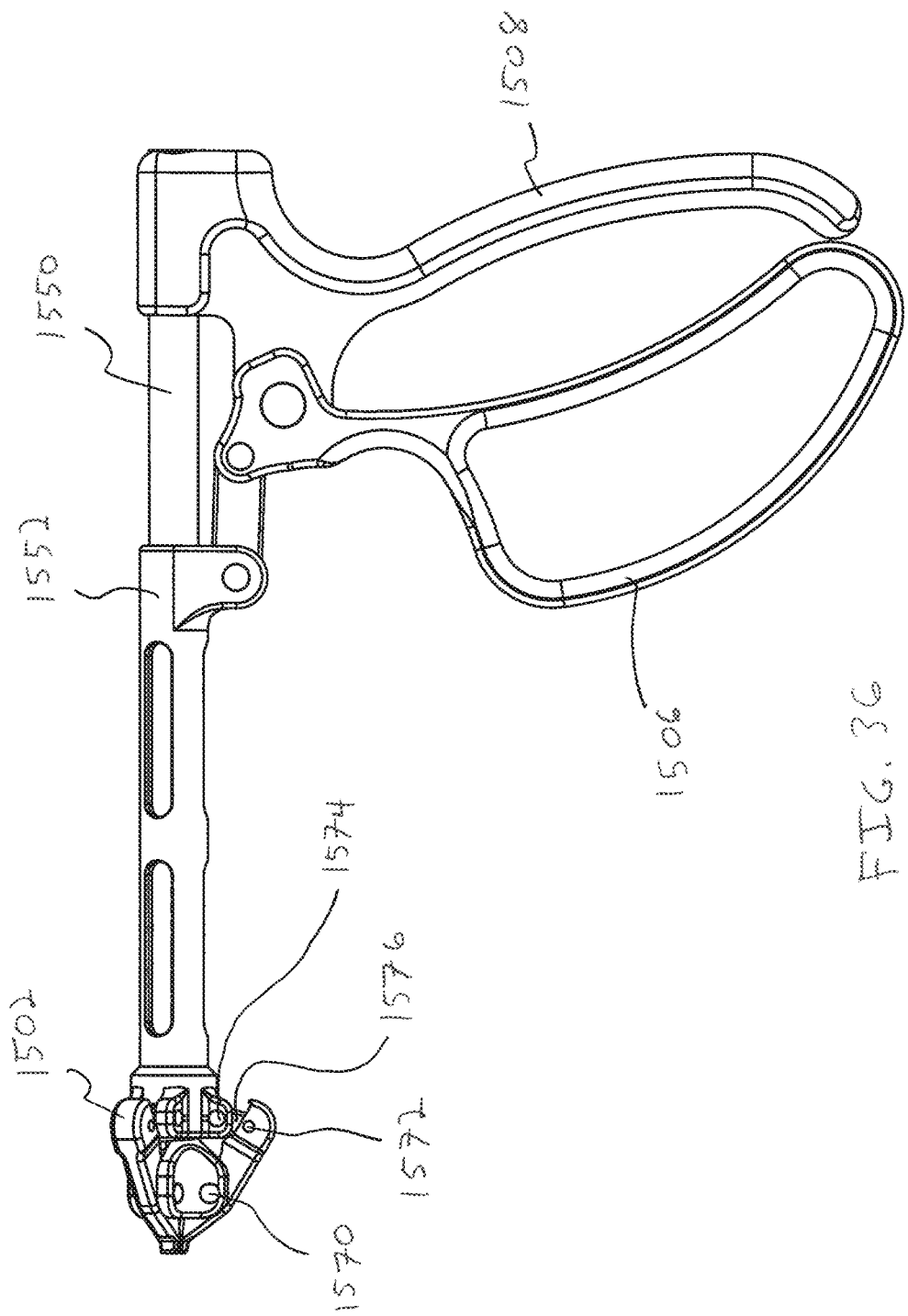
FIG. 36 is a side elevational view similar to FIG. 35 showing the locking lever moved toward the handle and the locking arms shifted to a clamping position.
Figure 37:
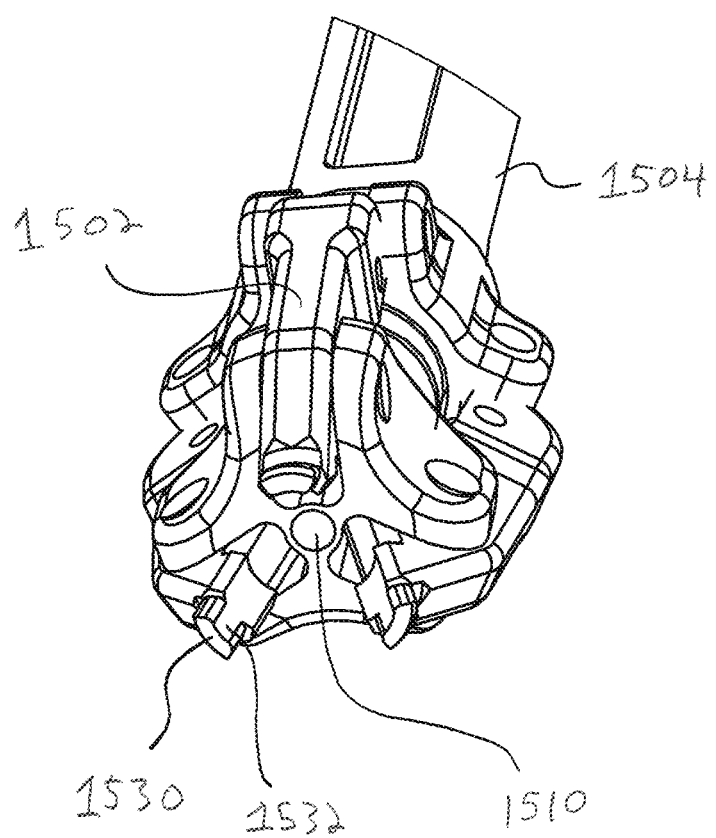
FIG. 37 is an enlarged perspective view of the distal end portion of the tool of FIG. 34 showing the locking arms in the open configuration.

With reference to FIGS. 34-41, the crimp tool 1500 will be discussed in greater detail. The crimp tool 1500 has a distal end portion 1504 including the arms 1502 which are configured to be connected to a crimp 1014, advanced along one of the cables 1030 to position the connected crimp 1014 within the associated throughbore 1012, and used to crimp the crimp 1014 to the cable 1030 by moving a lever 1506 toward a handle 1508 of the tool 1500. With reference to FIG. 37, the distal end portion of 1504 has a through opening 1510 into which a free end 1512 of the cable 1030 (see FIG. 29) is fed until a length 1512 of the cable 1030 exits an outlet opening 1520 of the tool 1005 at a proximal end 1522 (see FIG. 39) of the tool 1300.

With reference to FIG. 37, the arms 1502 have distal crimp members 1530 with crimp surfaces 1532 configured to engage the collar 1032 of the crimp 1014. The collar 1032 has a generally tubular configuration with an outer surface 1533 (see FIG. 32) and the crimp surfaces 1532 have a complimentary curvature for engaging the outer surface 1533. In other forms, the crimp member 1530 may include an inwardly extending pin, a generally flat crimp surface 1532, or a convex surface that mates with complimentary features on the crimp collar 1032.

With reference to FIGS. 35, 36, 38, the crimp tool 1500 has an inner shaft 1550 secured to the handle 1508 and an outer sleeve 1552 slidably mounted on the inner shaft 1553. The lever 1506 is pivotably connected to the handle 1508 by pin 1554 and is connected to the outer sleeve 1552 by a linkage including a link 1556 and pins 1558, 1560. Pivoting the lever 1506 toward the handle 1508 shifts the outer sleeve 1552 in direction 1562, as shown in FIGS. 35 and 36. Movement of the outer sleeve 1552 in direction 1562 pivots the arms 1502 about pins 1570 which connect the arms 1502 to the inner shaft 1550, as shown in FIG. 41. To produce pivoting of the arms 1502, the outer sleeve 1552 is connected to the arms 1502 by a linkage including pins 1572, 1574 and a link 1576, as shown in FIG. 41. Further, a spring 1580 is positioned between the inner shaft 1550 and outer sleeve 1552 and is configured to shift the outer sleeve 1552 toward the proximal portion 1522 of the tool 1500 when the lever 1506 is released thereby opening the arms 1502 and disengaging the distal end portion 1504 of the tool 1500 from the crimp 1014.

Figure 42B:
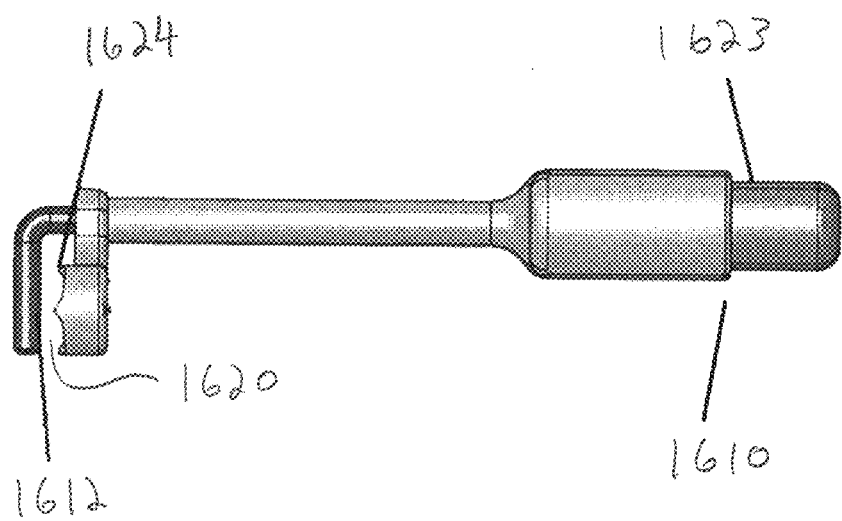
FIG. 42B is a side elevational view of the guide of FIG. 42A showing an L-shaped guide member spaced from teeth of the guide.

With reference to FIGS. 42A and 42B, a guide tool 1600 is shown that may be used to install the bone plate system 1000 on the rib 1006. The guide tool 1600 has a foot 1604 that is positioned against the rib outer surface 1034 and teeth 1624 of the foot 1604 which engage the rib outer surface 1034 and keep the foot 1604 at a desired position along the rib 1006. At an opposite end of the guide 1600, there is a button 1610 biased in direction 1622 by an internal spring 1609 of the guide 1600 and a L-shaped member 1616 connected to the button 1610. Depressing the button 1610 shifts the L-shaped member in direction 1614 away from the foot 1604. This enlarges a spacing 1620 between the member 1612 and the foot 1604 to permit a bone, such as the rib 1006, to be inserted between the L-shaped member 1616 and the foot 1604. The foot 1604 has through openings 1630 for guiding a drill member, such as a drill bit of an electric or manual drill, into the rib 1006. The guide 1600 also has a scale 1623 (see FIG. 42A) that indicates how far the button 1610 has been depressed. The distance the button 1610 has been depressed reflects the spacing between the L-shaped member 1616 and the foot 1604 and the thickness of the bone received therebetween. This permits a surgeon to measure the thickness of the bone and select an appropriate connector device, such as a cable or screw, for the bone.

Figure 43A:
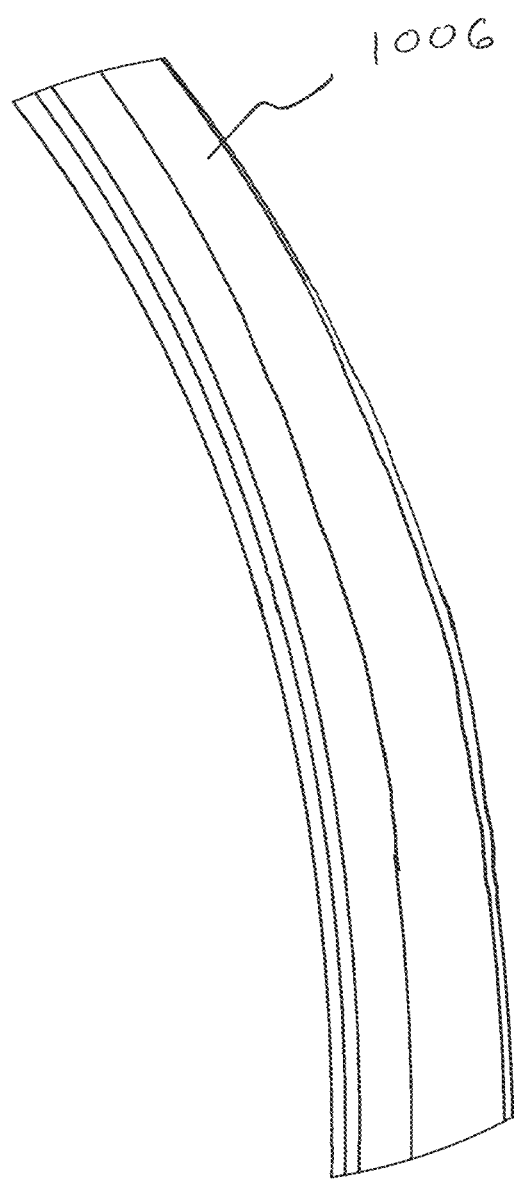
Figure 43B:
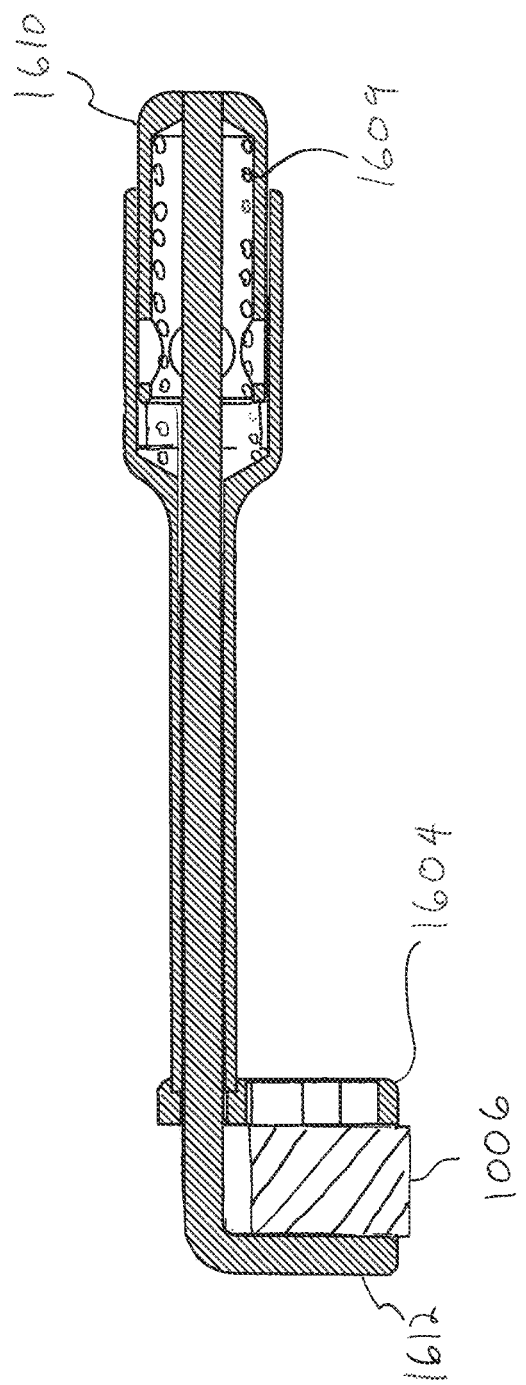

The bone plate system 1000 may be installed on new rib 1006 using a method that is similar in many aspects to the method of installing the bone plate system 10 on the ribs 12, 14 discussed above. With reference to FIGS. 43A-43H, the method of installing the bone plate system 1000 will be discussed in greater detail. Initially, an incision is made near the bone or bones to be stabilized, such as rib 1006 in FIG. 43A, to gain access to the bone or bones. Next, the guide 1600 is advanced into position near the rib 1006, the button 1610 is pressed to separate the L-shaped member 1616 from the foot 1604, and the guide 1600 is manipulated to position the L-shaped member 1616 on one side of the rib 1006 and the foot 1604 on the opposite side of the rib 1006, as shown in FIG. 43B (which is a cross-sectional view taken across line 43B-43B in FIG. 42A). Positioning the guide 1600 on the rib 1006 includes locating a middle region 1602 of the foot 1604 (see FIG. 42A) directly over a desired separation site, such as cut path 1629 (see FIG. 43AD).

As noted above, the guide 1600 has an internal spring 1609 that biases the button 1610 and the L-shaped member 1612 connected thereto in direction 1622 as shown in FIG. 42A. The biasing force applied to the L-shaped member 1612 clamps the rib 1006 between the L-shaped member 1612 and the foot 1604. The frictional engagement of the L-shaped member 1612 and the teeth 1624 with the rib 1006 maintains the guide 1600 in position on the rib 1006 while forming holes 1048 in the rib 1006, as shown in FIG. 43B. More specifically, the openings 1630 of the foot 1604 are sized to receive a tool for forming holes 1048, such as a drill bit of an electric or manual drill. The spacing and location of the openings 1630 on the foot 1604 is substantially identical to the spacing and location of the throughbores 1012 of the bone plate 1010. In this manner, once the holes 1048 have been formed in the rib 1006, the bone plate 1010 may be positioned on the rib 1006 and the throughbores 1012 readily aligned with the holes 1048 formed in the rib 1006.

Figure 43C:
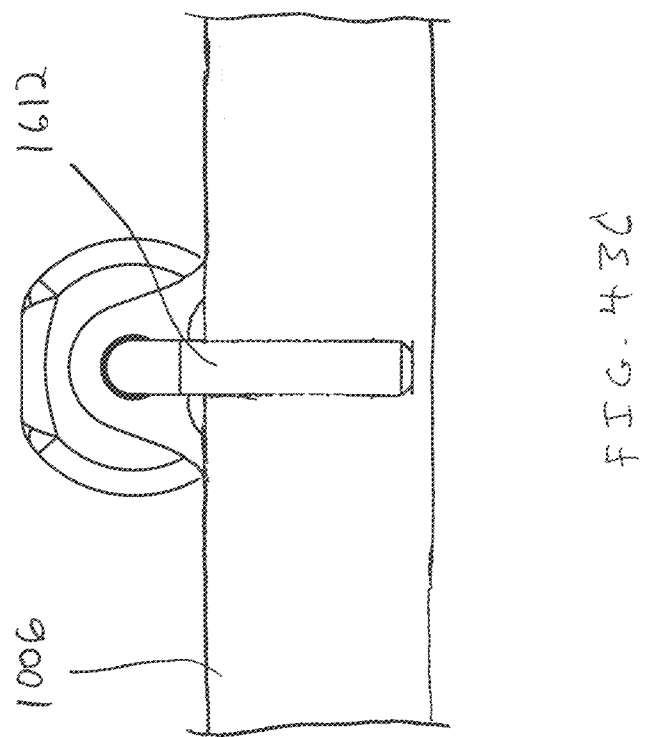
Figure 43D:
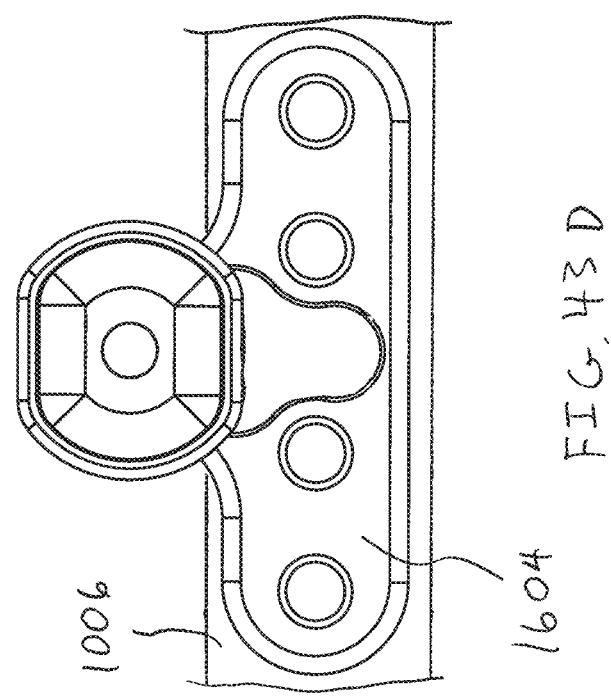

With reference to FIG. 43C, the guide 1600 is shown positioned on the rib 1006 with the openings 1630 of the foot 1604 generally positioned at a center of the rib 1006. The center of the rib may be the thickest part of the rib 1006 to increase the stability of the bone plate system 1000 on the rib 1006 and may allow the holes 1048 to avoid the neurovascular bundle on the bottom of the rib 1006. A rear view of the guide 1600 positioned on the rib 1006 is shown in FIG. 43D. As can be seen from FIGS. 43C and 43D, the L-shaped member 1612 and guide 1604 compress the rib 1006 therebetween.

Figure 43E:
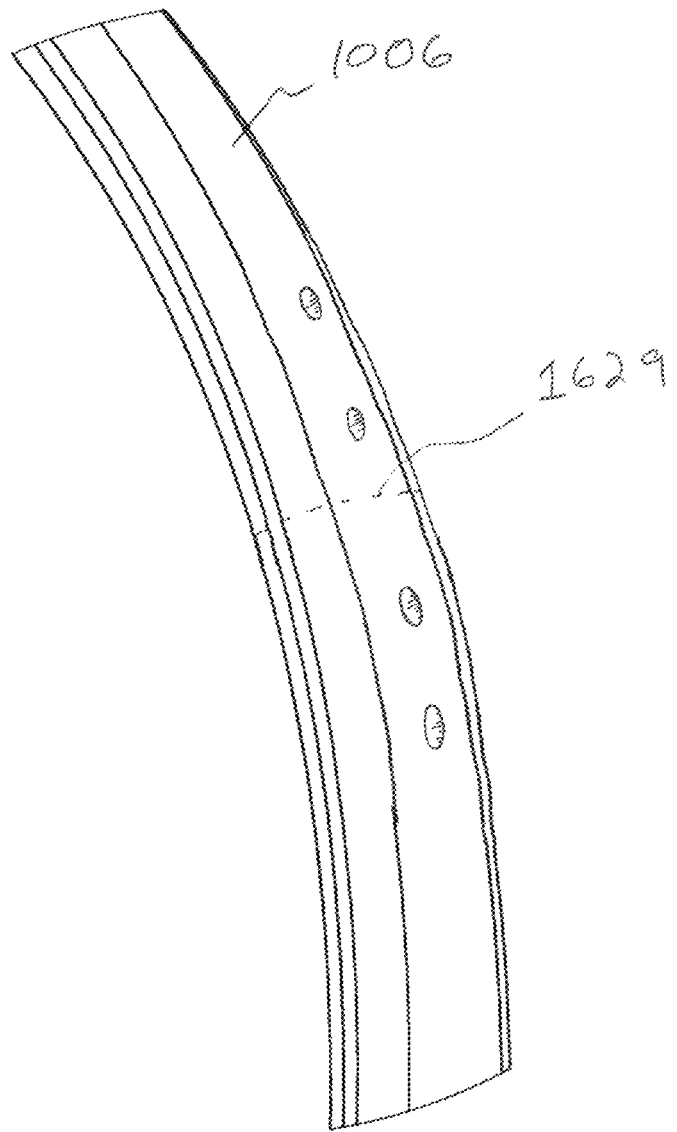
Figure 44:
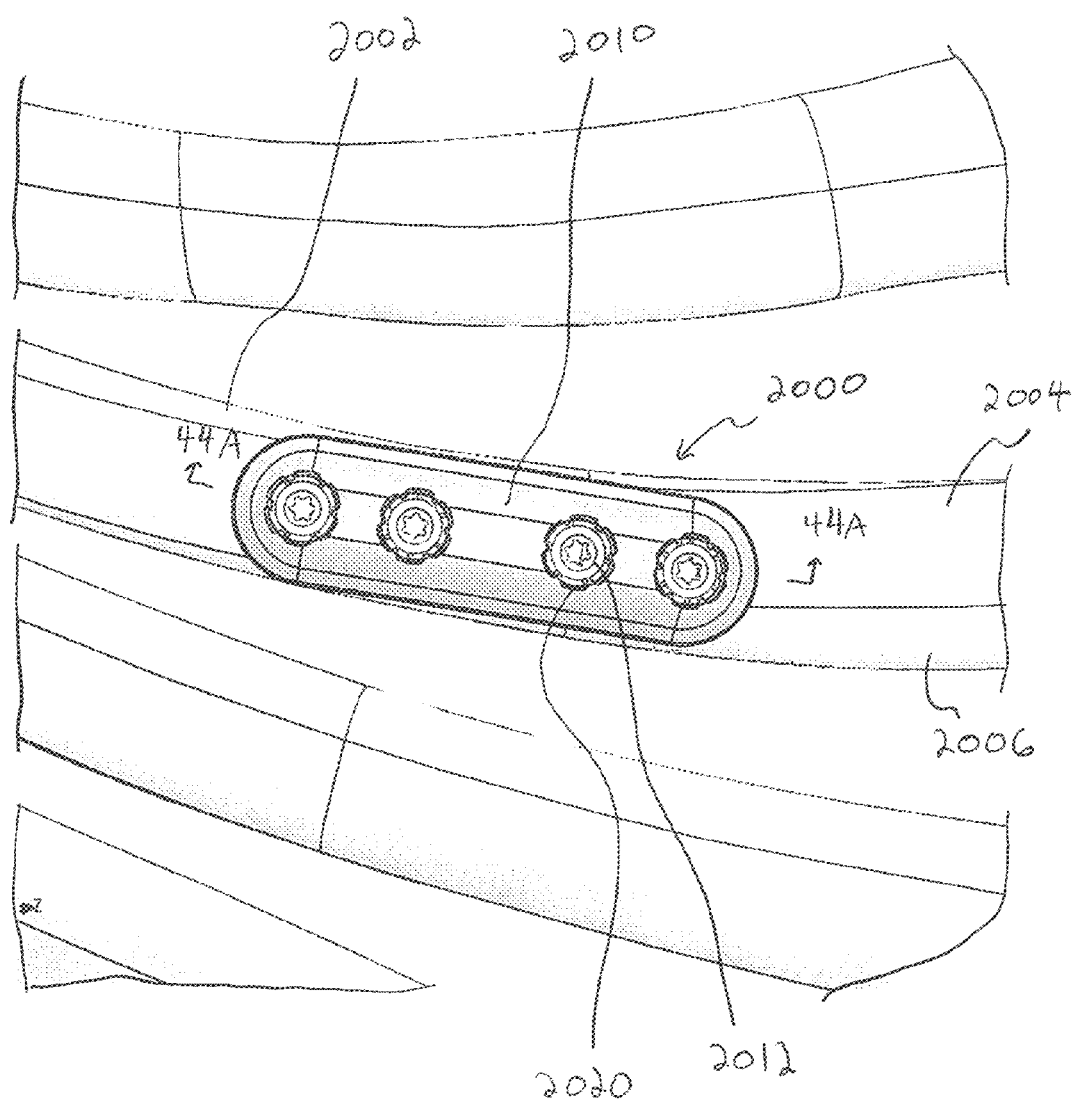
FIG. 44 is a perspective view of another bone plate system secured to a cut rib.
Figure 44A:
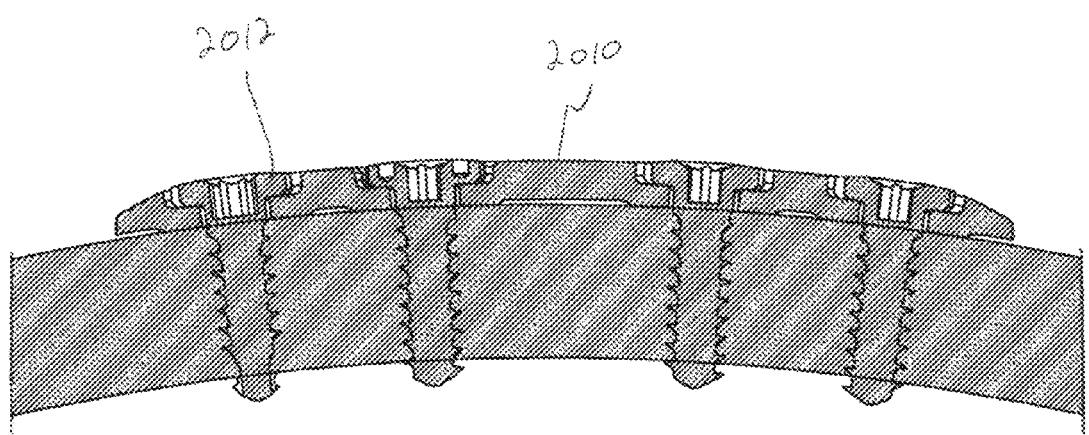
FIG. 44A is a cross-sectional view taken across line 44A-44A in FIG. 44

Once the holes 1048 have been formed in the rib 1006, the guide 1600 may be removed from the rib 1048 as shown in FIG. 43E. The cables 1030 are preferably preassembled with the plugs 1040 swaged thereon. The leading or free ends 1512 of the (see FIG. 29) cables 1030 are then advanced through the holes 1048 from the underside 1062 of the rib 1006, as shown in FIG. 43E. The free ends 1512 of the cables 1030 are pulled outward from the incision and moved to the side of the incision to provide room at the surgical site.

Next, the rib 1006 is separated at a desired separation site, such as cutting the rib 1006 along the cut path 1629 (see FIG. 43D) to form the cut 1008, and separate the rib 1006 into rib portions 1002, 1004, as shown in FIG. 43F. In one approach, a cutting tool such as a bone saw is used to cut the rib 1006 and separate the rib 1006 into the rib portions 1002, 1004. By forming the holes 1048 prior to cutting the rib 1006, an exact alignment of the rib portions 1002, 1004 is ensured when the rib portions 1002, 1004 are subsequently secured together with the bone plate 1012. Further, forming the holes 1048 prior to cutting the rib 1006 increases the stability and ease of forming the holes 1048 when compared to manipulating loose rib portions 1002, 1004 after the rib 1006 has been cut. This approach stands in contrast to some prior approaches where the drilling operations performed after the rib 1006 has been broken.

The rib portions 1002, 1004 may be moved apart after the rib has been cut to provide access to tissue or organs within the rib cage. The cables 1030 may remain positioned in the holes 1048 in the rib portions 1002, 1004 during separation of the rib portions 1002, 1004 and subsequent operation upon the organs or tissues. Because the cables 1030 are relatively flexible, the free ends 1512 of the cables 1030 can be moved to the side of the incision and remain out of the way of the surgeon without disconnecting the cables 1030 from the rib portions 1002, 1004.

Once the tissues or organs within the rib cage have been operated upon, the free ends 1512 of the cables 1030 may be advanced into the throughbores 1012 of the bone plate 1010 from the lower surface 1101 of the plate member 1010. The bone plate 1010 may then be slid along the cables 1030 until the lower surface 1101 seats against the rib outer surface 1034, as shown in FIG. 43H.

If the rib portions 1002, 1004 have been moved apart, they may need to be approximated. The bone plate system 1000 provides a simple and efficient approach for approximating the rib portions 1002, 1004 that includes sliding the bone plate 1010 along the tensioned cables 1030 to draw the rib portions 1002, 1004 together. For example, if the rib portions 1002, 1004 have been moved apart in directions 1514, 1516 cables 1030A, 1030B and 1030C, 1030D may extend obliquely to each other once the free ends 1512 thereof have been advanced through the respective throughbores 1012 of the bone plate 1010 and the bone plate 1012 is spaced from and oriented generally parallel to the rib portions 1002, 1004, as shown in FIG. 43G. The free ends 1512 are pulled away from the rib portions 1002, 1004 in direction 1518, which engages the plugs 1040 with the underside 1046 of the rib portions 1002, 1004 and tensions the cables 1030, and the bone plate 1012 is pressed toward the rib portions 1002, 1004 in direction 1519. This causes the cables 1030 to slide along a lower edge 1524 of the throughbores 1012 as the cable free ends 1512 are pulled in direction 1518 and the bone plate 1012 is moved in direction 1519. The bone plate 1012 thereby acts as a pulley to redirect the tension forces in the cables 1030A-1030D and draw the rib portions 1002, 1004 together.

Next, one of the crimps 1014 is connected to the distal end portion 1504 of the crimp tool 1500. In one approach, the crimp 1014 and the arms 1502 of the distal end portion 1504 are configured so that the crimp members 1530 thereof can snap into the openings 1090, 1092, 1094 of the crimp 1014 and releasably connect the crimp 1014 to the distal end portion 1504.

Figure 34:
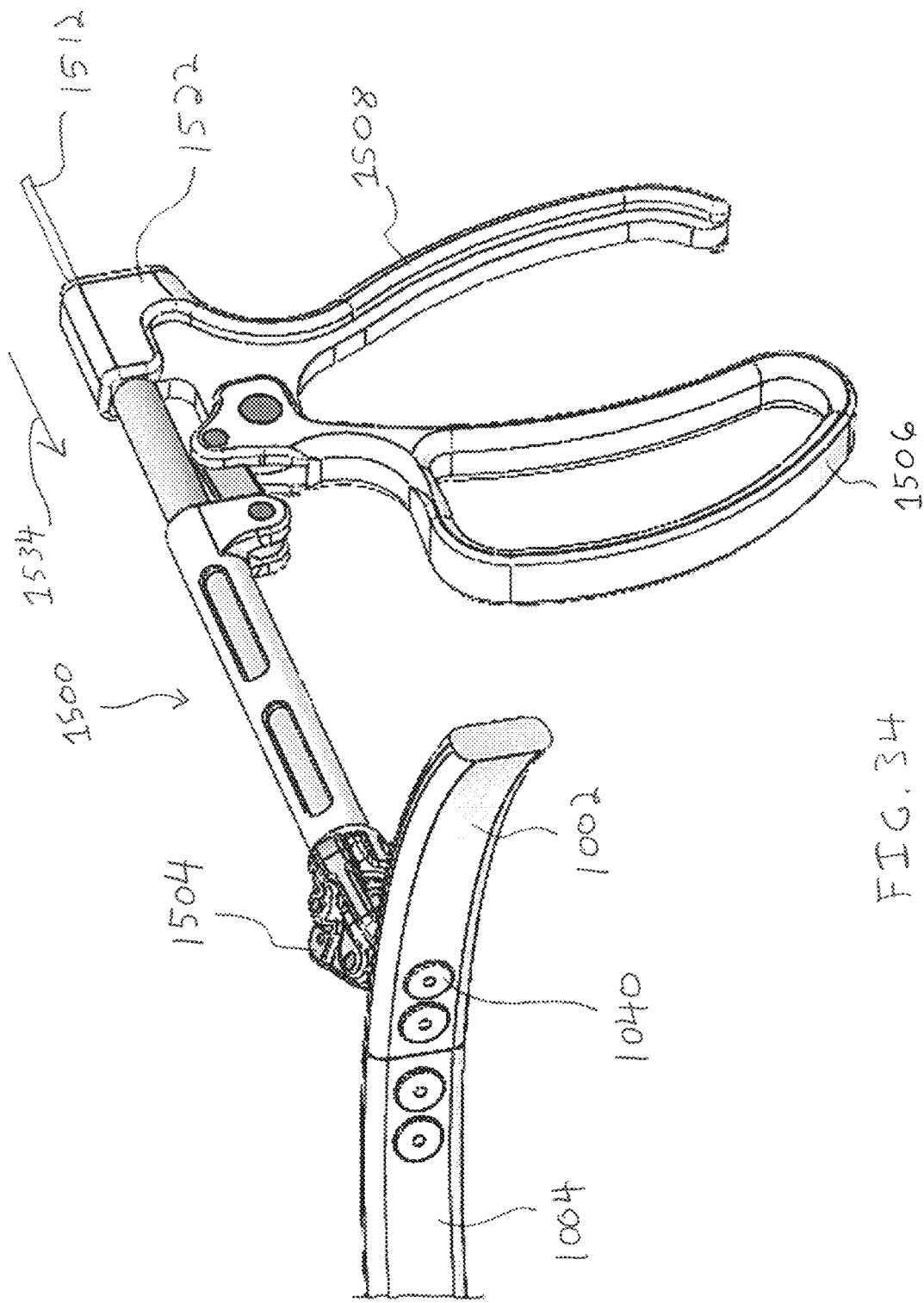
FIG. 34 is a perspective view of a tool locking one of the crimps to one of the cables.

The free end 1512 of one of the cables 1030 is fed into the aperture 1026 of the crimp 1014, into the through opening 1510 (see FIG. 37) of the crimp tool distal end portion 1504, and through a cable passageway 1521 of the tool 1500 (see FIG. 40). The cable free end 1512 is advanced until the free end 1512 exits the outlet opening 1520 of the tool 1500 and a proximal portion 1522 of the cable 1030 extends outward from the outlet opening 1520 (see FIG. 34). The cable proximal portion 1522 may be grasped and the tool 1500 shifted in direction 1534 along the cable 1030 toward the rib portions 1002, 1004. The tool 1500 is shifted along the cable 1030 until the distal end portion 1504 and crimp 1014 connected thereto reach the bone plate 1010, as shown in FIG. 34.

Next, the cable 1030 is tensioned and the crimp 1014 pressed against the bone plate 1010 to compress the rib portion 1002 or 1004 between the plug 1040 of the cable 1030 and the bone plate 1010 before the crimp 1014 is crimped to fix the crimp 1014 to the bone plate 1010, as shown in FIG. 43I. More specifically, while pulling the cable free end 1512 away from the bone plate 1010, the tool distal end portion 1504 (and crimp 1014 connected thereto) is pushed toward the bone plate 1010 to squeeze the rib portion 1002 or 1004 between the plug 1040, the bone plate 1010, and the crimp 1014. The lever 1506 is then moved toward the handle 1508 to shift the arms 1502 to the locking configuration (see FIG. 36) and crimp the crimpable collar 1032 of the crimp 1014 onto the cable 1030. The cable 1030 may then be cut flush with the collar 1032 of the crimp 1014 (see FIG. 30). This process is repeated for the remaining cables 1030 until the bone plate 1012 has been secured to the rib portions 1002, 1004, as shown in FIG. 28. Although the foregoing method has been described as a series of steps, it will be appreciated that the order of the steps may be varied to compliment a particular procedure. Further, it will be appreciated that aspects of the steps may be modified, combined, or removed as appropriate.

With reference to FIGS. 44A-55, a bone plate system 2000 is shown that may be used to stabilize one or more bones, such as portions 2002, 2004 of a cut rib 2006. The bone plate system 2000 is similar in many respects to the bone plate system 1000 discussed above. The following discussion will describe differences between the bone plate system 2000 and the bone plate system 1000. One difference is that the bone plate system 2000 has a bone plate 2010 and screws 2012 which secure the bone plate 2010 to the rib 2006 rather than the cables 1030 of the bone plate system 1000.

Figure 49:
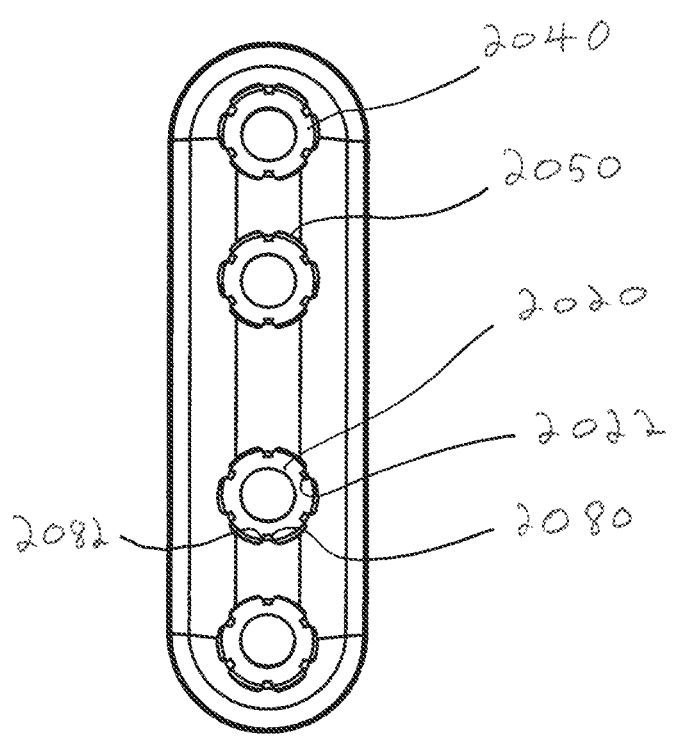
FIG. 49 is a top plan view similar to FIG. 46 showing the bone screws removed from the bone plate throughbores and seating surfaces of the throughbores which engage the heads of the bone screws.
Figure 50:
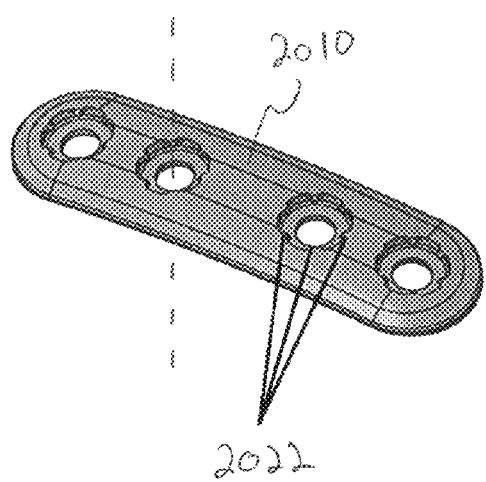
FIG. 50 is a perspective view of the bone plate of FIG. 44 showing the retention members of each throughbore disposed above the seating surface of the throughbore.

The bone plate 2010 has throughbores 2020 for receiving the screws 2012 and screw retention structures, such as retention members 2022, which are configured to resist back out of the bone screws 2012. More specifically, the bone screws 2012 each have a head portion 2030 and a shank portion 2032 depending therefrom, as shown in FIGS. 45 and 47. The bone screws 2012 are driven into the throughbores 2020 to seat the head portions 2030 against seating surfaces 2040 of the throughbores 2020 (see FIG. 49). With reference to FIGS. 49 and 50, the retention members 2022 are disposed circumferentially about a throughbore wall 2050 and extend radially inward therefrom. The retention members 2022 are disposed above the seating surface 2040 along an axis 2052 of the throughbore 2020 and within the path of the screw head portion 2030. The retention members 2022 are configured to deflect as the screw head portion 2030 travels into the throughbore 2020 and snap back over the head portion 2030 once the head portion 2030 has been seated within the throughbore 2020.

The bone plate 2010 has raised pods 2060 on a lower surface 2062 of the bone plate 2010. The pods 2060 extend about the throughbores 2020 and reduce the amount of surface contact between the bone plate lower surface 2062 and the rib 2006. This may reduce irritation caused by the bone plate 2010 on the rib 2006.

With reference to FIGS. 52 and 53, the screw head portions 2030 include a radially enlarged head 2070 with radially extending catches 2072 having engagement surfaces 2074, 2076 configured to contact and engage outer side surfaces 2080, 2082 of the retention members 2022 (see FIG. 49). Engagement between the surfaces of the catches 2072 and the retention members 2022 restricts rotary movement of the bone screw 2012 in a back-out direction from within the respective throughbore 2020. Further, the screw head 2070 has circumferentially extending axial stop surfaces 2084 which are disposed axially below the retention members 2022 with the screw 2012 seated in the throughbore 2020. Axial back out movement of the bone screw 2012 brings the bone screw stop surfaces 2084 into engagement with the retention members 2022 and further restricts back out of the bone screws from the throughbores 2020 of the bone plate 2010. Thus, the bone plate retention members 2022 and bone screw head portions 2030 have cooperating features which limit axial and rotary backout movement of the bone screws 2012 once the bone screws 2012 have been driven into the throughbores 2020.

Figure 55:
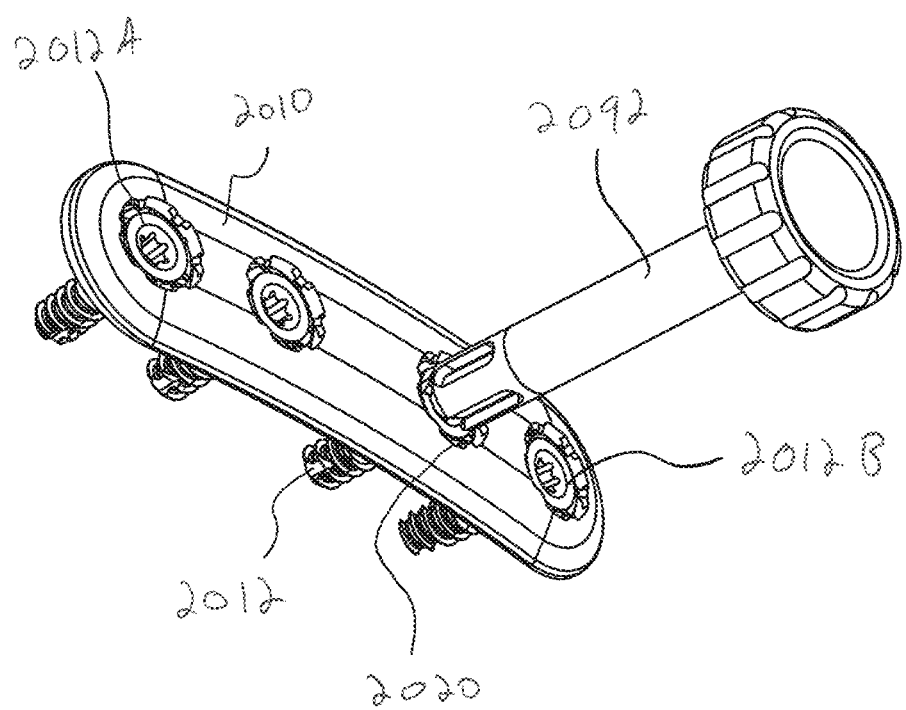
FIG. 55 is a perspective view of the bone plate system of FIG. 44 showing a driving tool driving one of the bone screws into the bone plate.

The bone screw 2012 may also have a drive recess 2090 for receiving a driver tool 2092, as shown in FIGS. 53 and 55. The drive recess 2090 may be, for example, a Torx, hex, or Phillips configuration, for engaging a corresponding shaft of the driver tool 2092.

Figure 54A:
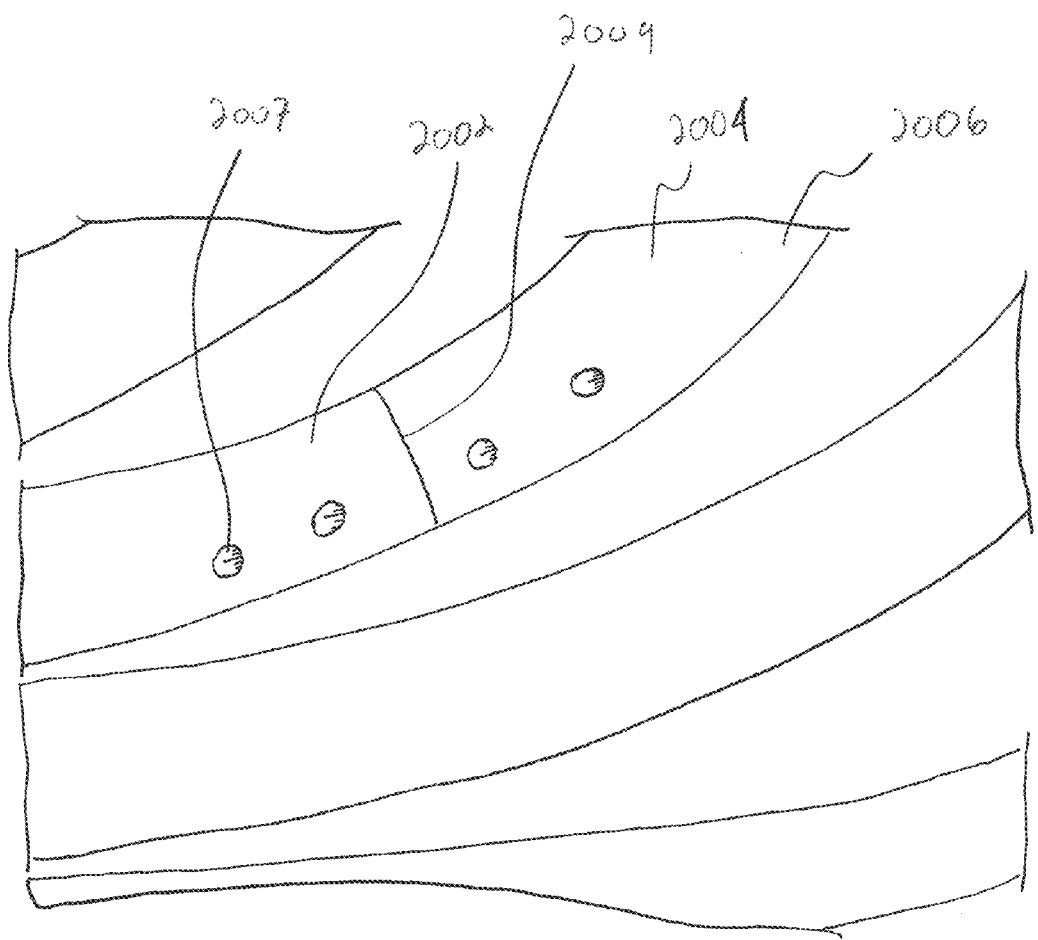
FIGS. 54A-54D illustrate a method of securing the bone plate system of FIG. 44 to a rib.

With reference to FIGS. 54A-D, the bone plate system 2010 may be installed in a substantially similar manner as the bone plate system 1000 with the exception that the bone screws 2012 are used to secure the bone plate 2010 to the rib 2006. The method of installing the bone plate system 2000 includes using the guide 1600 to drill holes 2007 in the rib 2006 before the rib is cut, in a manner similar to the method of installation of the bone plate system 1000. The rib 2006 may then be cut 2009 into the portions 2002, 2004, as shown in FIG. 54A.

Figure 54B:
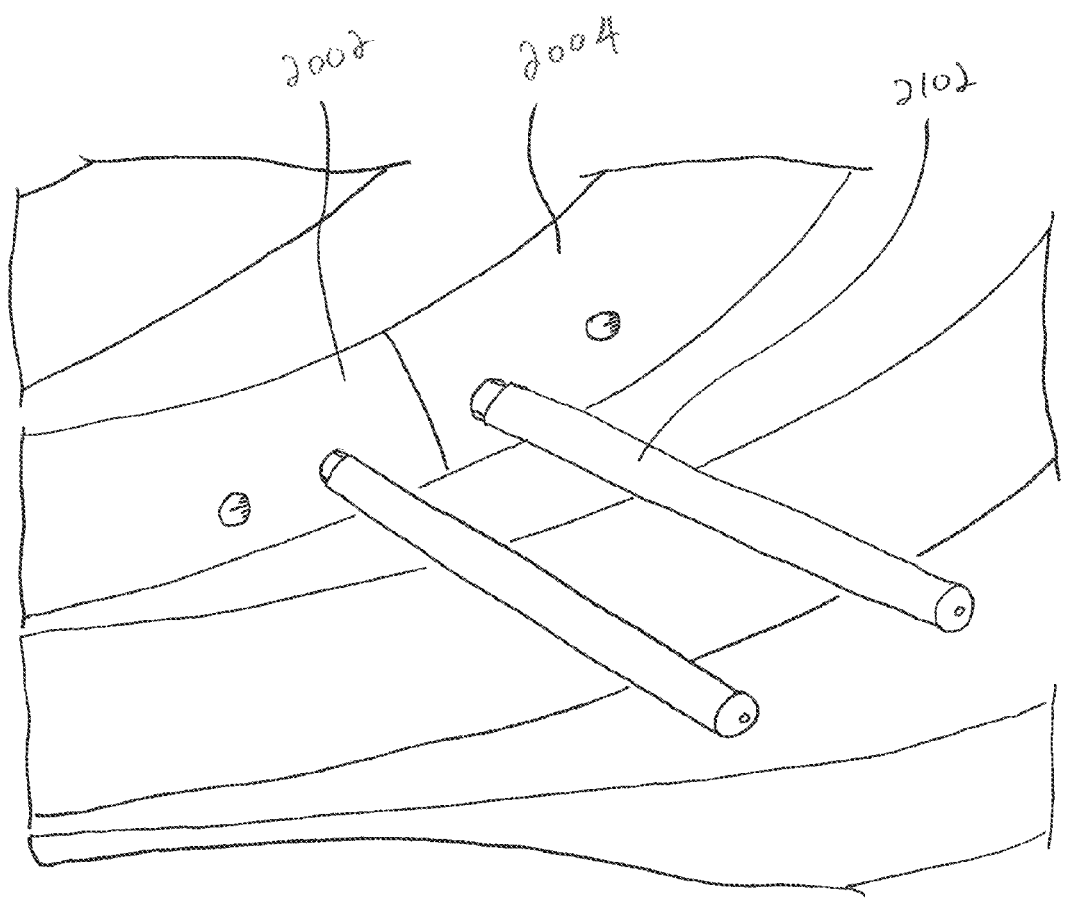
Figure 54C:
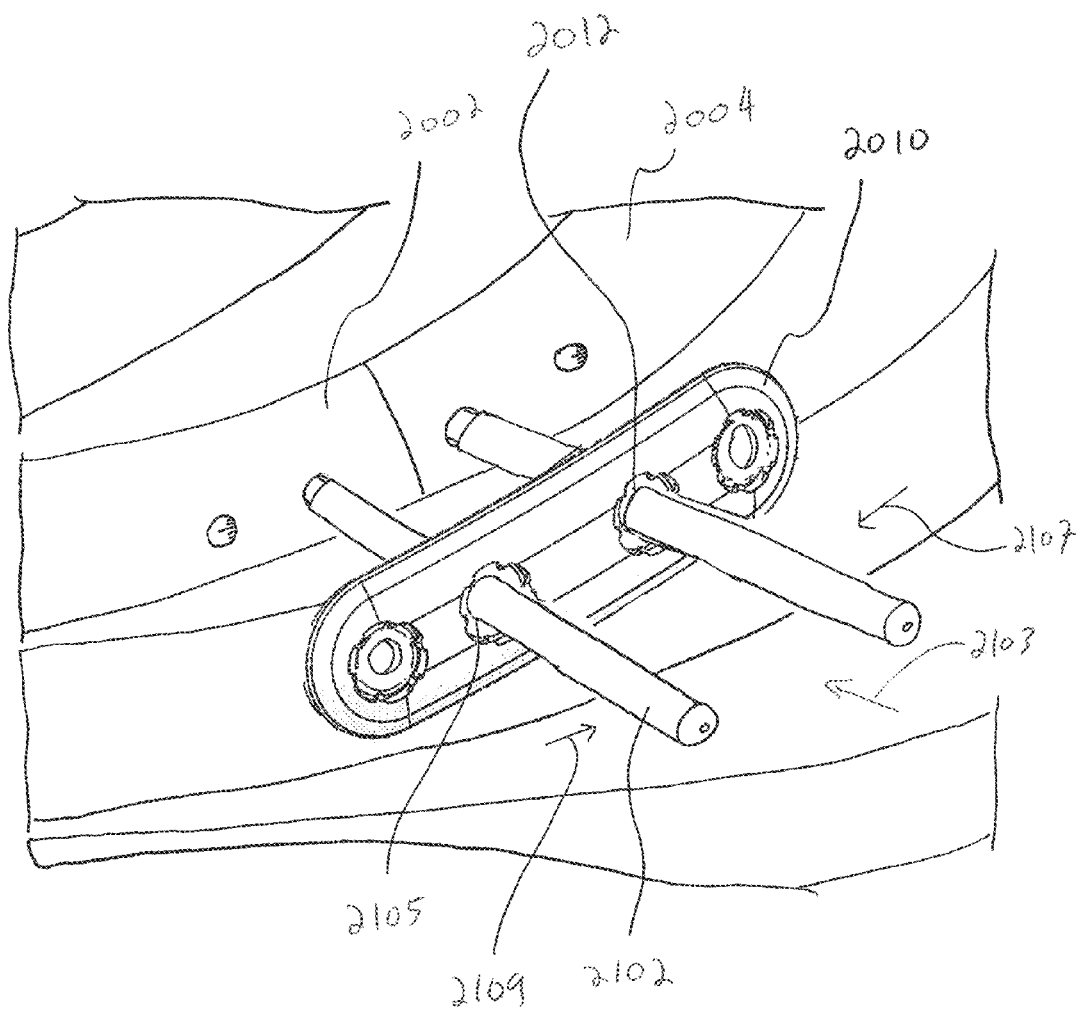

Next, alignment pins 2100, 2102 may be driven into the holes 2009 formed in the rib portions 2002, 2004 after using the guide 1600, as shown in FIG. 54B. The bone plate 2010 is positioned so that the through openings 2012 thereof are aligned with the alignment pins 2100, 2102. The bone plate 2010 is then slid along the alignment pins 2100, 2102 in direction 2103 toward the rib portions 2002, 2004, as shown in FIG. 54C. The bone plate 2010 is advanced along the alignment pins 2100 until the bone plate 2010 seats against the rib portions 2002, 2004.

If the rib portions 2002, 2004 have been separated to provide access to tissues and organs within the chest cavity, sliding the bone plate 2010 along the alignment pins 2102 may approximate the rib portions 2002, 2004. More specifically, edges 2105 of the through openings 2012 of the bone plate 2010 engage the outer surfaces of the alignment pins 2102 and transfer the force applied to the bone plate 2010 to move the bone plate 2010 in direction 2103 into the alignment pins 2102 which draws the pins together in directions 2107, 2109, as shown in FIG. 54C.

Figure 54D:
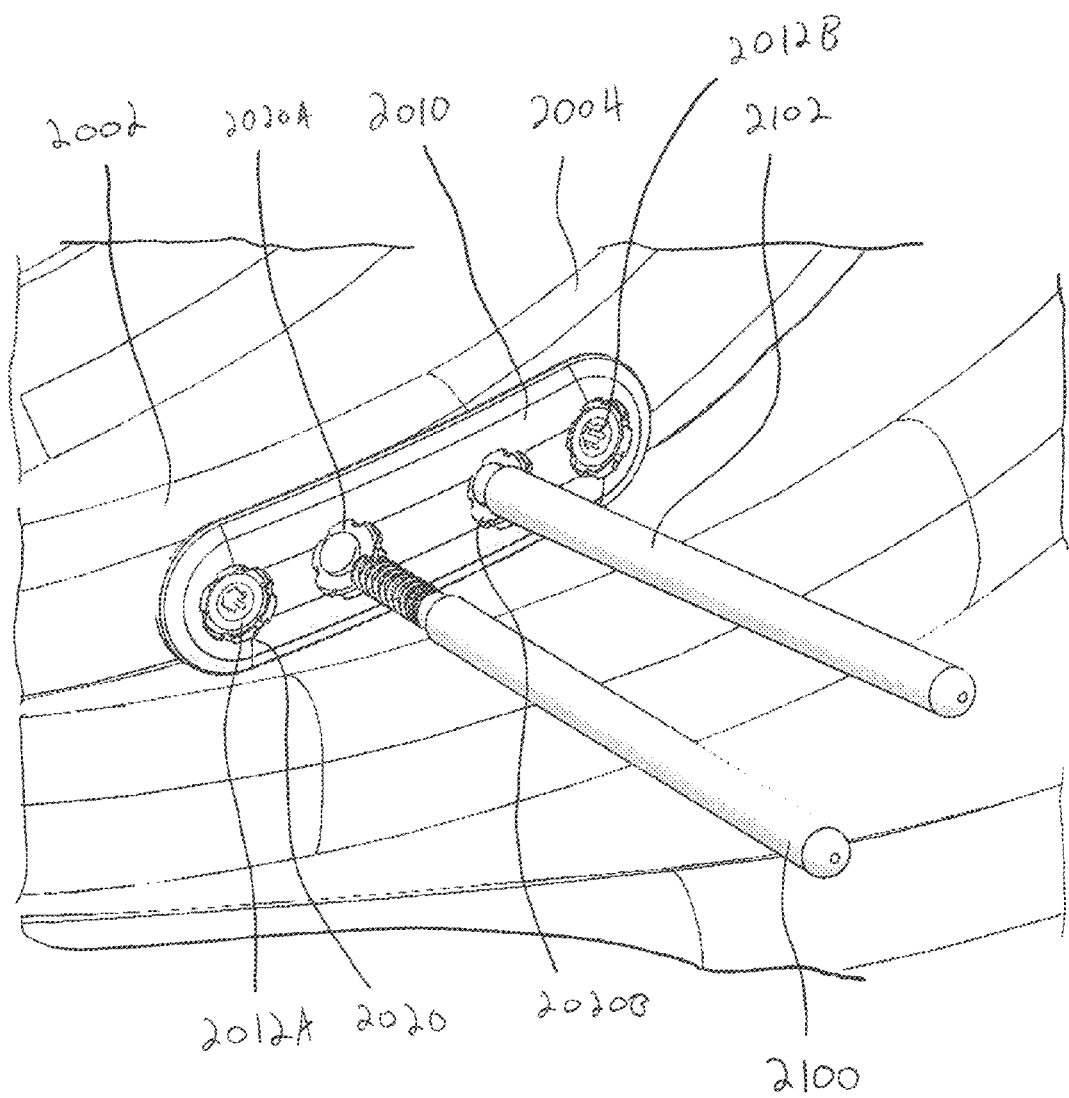

The driver tool 2092 may then be used to drive screws 2012A, 2102B into the throughbores 2020 not occupied by the alignment pins 2100, 2102 (see FIG. 55). Once the screws 2012A, 2012B have been driven into the throughbores 2020, the alignment pins 2102 may be removed from the remaining throughbores 2020A, 2020B as shown in FIG. 54D. Screws 2012 may then be driven into the throughbores 2020A, 2020B to secure the bone plate 2010 to the rib portions 2002, 2004.

With reference to FIGS. 56-64, a bone plate system is shown for stabilizing one or more bones, such as portions of a cut rib. The bone plate system 2500 is substantially similar to the bone plate system 2000 such that differences between the two systems will be highlighted. Further, the bone plate system 2500 may be installed using a method that is substantially similar to the method described above with respect to bone plate system 2000.

The bone plate system 2500 has a bone plate 2502 with throughbores 2504 configured to receive head portions 2506 of bone screws 2508. The bone plate 2502 has retention structures, such as pawl members 2520 configured to engage teeth 2522 of the screw head portion 2506. With reference to FIG. 57, the pawl members 2520 extend parallel to a longitudinal axis 2530 of the bone plate 2502.

The bone plate 2502 has elongated cutouts 2540, 2542 on opposite sides of the pawl member 2520 that increase the flexibility of the pawl member 2520. The pawl member 2520 is resilient and can deflect outward in direction 2550 as the screw 2508 is driven into the throughbore 2504 with rotation in direction 2552. However, turning of the bone screw 2508 in reverse back out direction 2554 engages the teeth 2522 with the pawl member 2520. This restricts the back out of the bone screw 2508 by limiting the ability of the bone screw 2508 to turn in the back out direction 2552.

Figure 60:
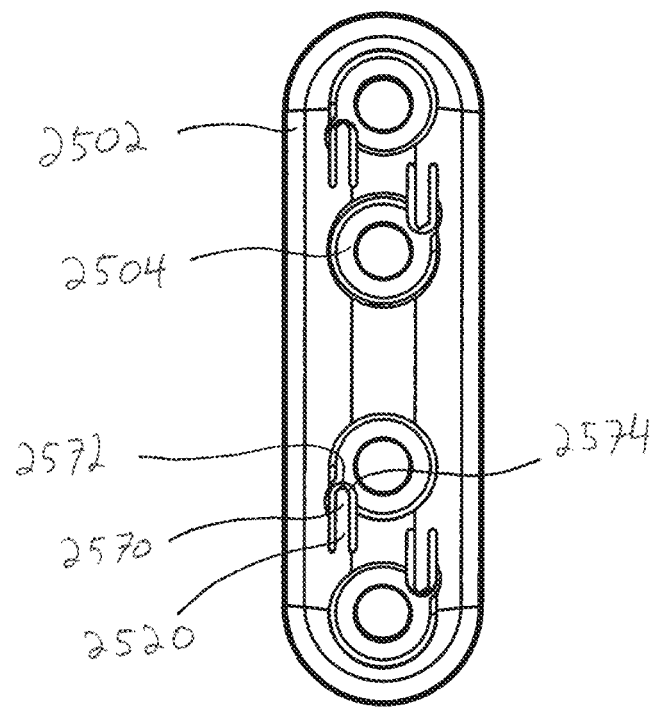
FIG. 60 is a plan view of the bone plate system of FIG. 56 with the bone screws removed to show the retention members of the bone plate extending into throughbores of the bone plate.
Figure 61:
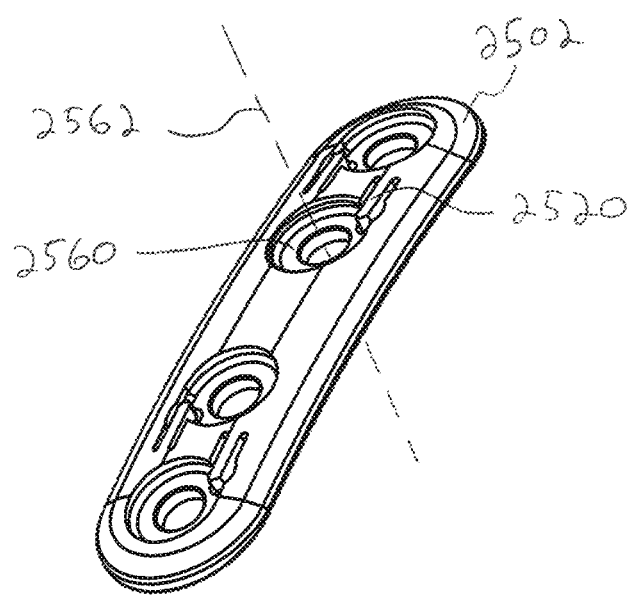
FIG. 61 is a perspective view of the bone plate of FIG. 56 showing the retention members of the bone plate extending above bone screw seating surfaces of the throughbores.
Figures 62, 63:
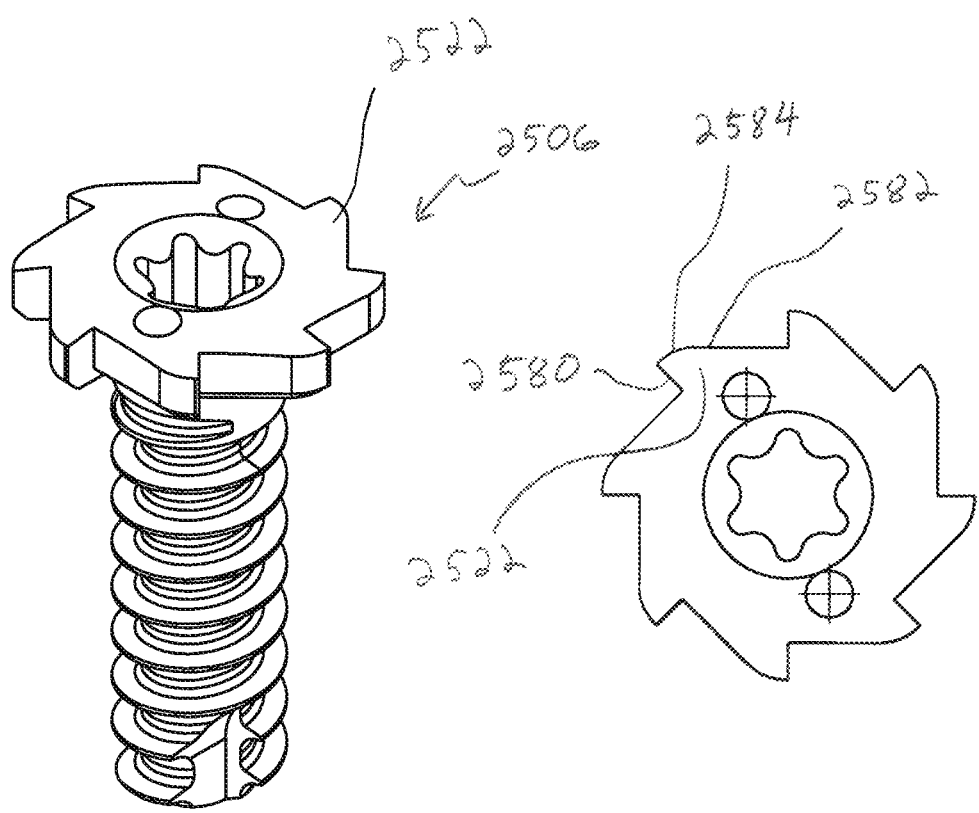
FIG. 62 is a perspective view of one of the bone screws of the bone plate system of FIG. 56 showing radially extending teeth of a head portion of the bone screw.
FIG. 63 is a top plan view of the bone screw of FIG. 62 showing ramp surfaces and stop surfaces of the head portion teeth.
Figure 64:
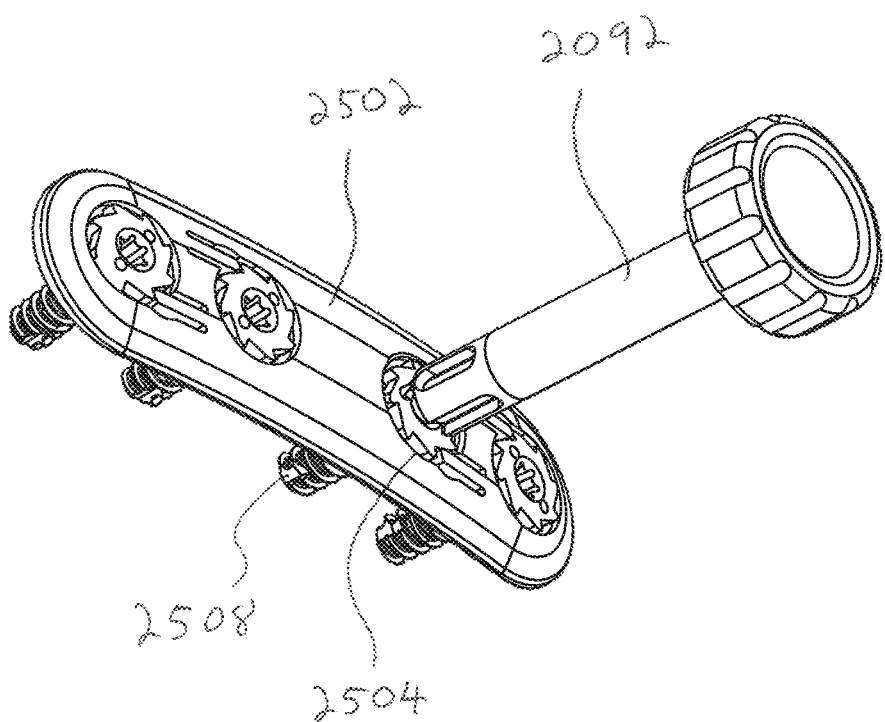
FIG. 64 is a perspective view of the bone plate system of FIG. 56 showing a tool driving a bone screw into the bone plate.

With reference to FIG. 61, the pawl member 2520 extends above a seating surface 2560 axially along a bore axis 2562 to engage the screw head portion teeth 2522. The pawl members 2520 have distal ends 2570 with a stop surface 2572 and a cam surface 2574 extending transverse to the length of the pawl member 2520. The stop surface 2572 of the pawl 2520 contacts radially extending stop surfaces 2580 of the teeth 2522 with rotation of the bone screw 2508 in back out direction 2552 as shown in FIGS. 57, 60, and 63. The bone screw teeth 2522 also have a ramp 2582 that extends from one stop surface 2580 to another and includes a cam surface 2584. As the screw 2508 is driven into the throughbore 2504 in direction 2552 (see FIG. 57) the bone screw teeth cam surfaces 2584 cam against the cam surface 2574 of the respective pawl 2520 to shift the pawl member 2520 outward in direction 2550, as shown in FIGS. 57 and 63. Further, the screws 2508 may be driven into the throughbores 2504 using the driver tool 2092, as shown in FIG. 64.

Figure 65:
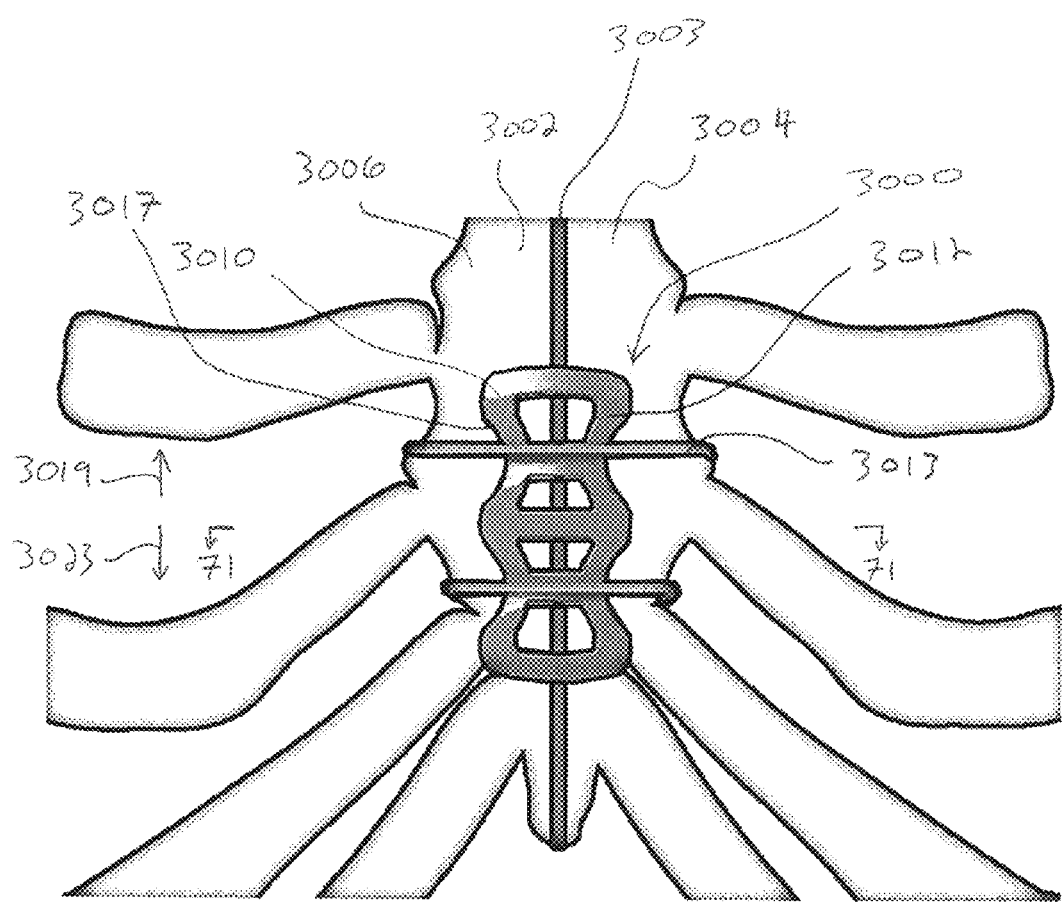
FIG. 65 is a schematic view of a plate member secured to a cut sternum.
Figure 66:
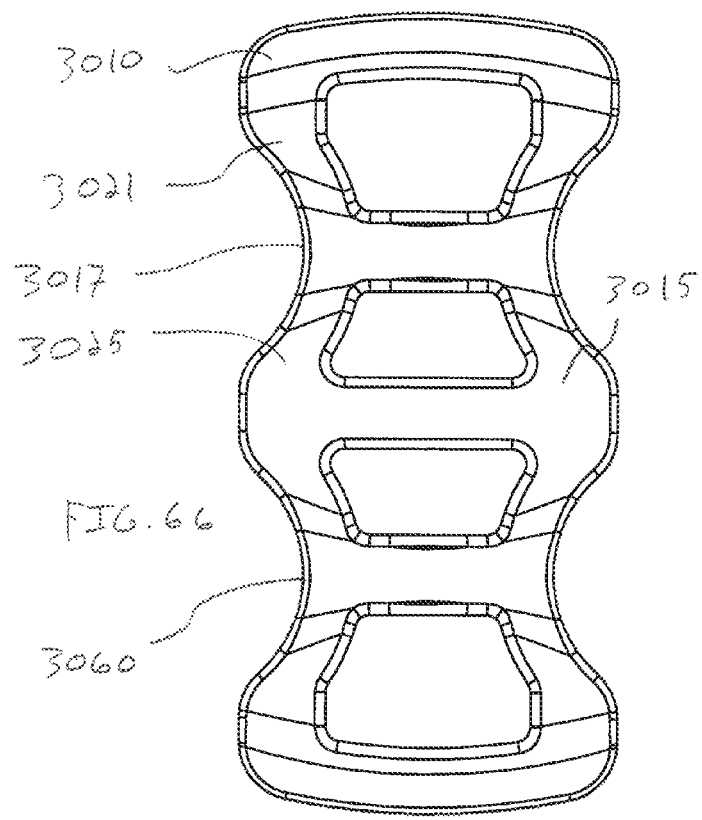
FIG. 66 is a top plan view of the plate member of FIG. 65 showing an outer scalloped profile of the plate member.

With reference to FIGS. 65-73, a bone plate system 3000 is provided for securing one or more bones, such as two halves 3002, 3004 of a sternum 3006 after the sternum 3006 has been cut or fractured. In one approach, the bone plate system includes a sternal plate 3010 having a low profile, substantially flat configuration with unidirectional teeth 3012 on the underside thereof. The sternal plate 3010 may have a unitary, one-piece construction, and may have a one-size-fits-all configuration to accommodate a range of different patient anatomies. The sternal plate 3010 may be used to provide additional stability and reinforcement in the sternum 3006 during implantation of a surgical construct, such as one or more wires or cables 3013, for sternal fusion and can be made of biocompatible materials including implant grade metal or polymer. A schematic view of the bone plate 3010 in situ is shown in FIG. 65.

Figure 67:
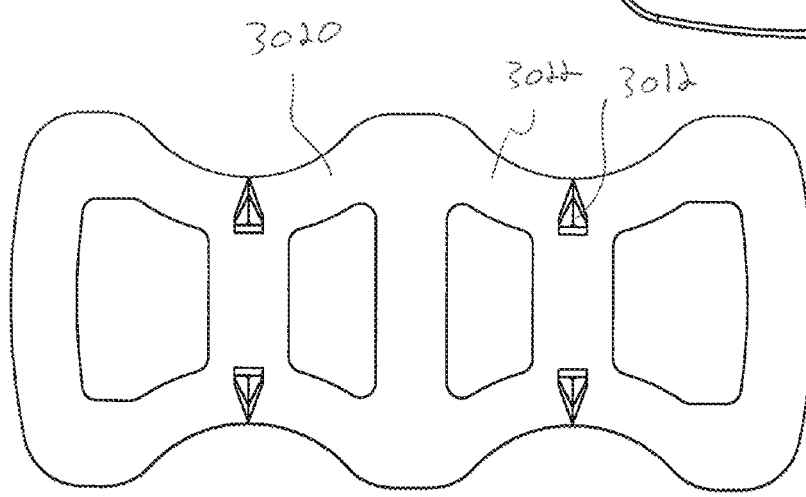
FIG. 67 is a bottom plan view of the plate member of FIG. 65 showing four teeth of the plate member positioned along a lower surface thereof.
Figure 71:
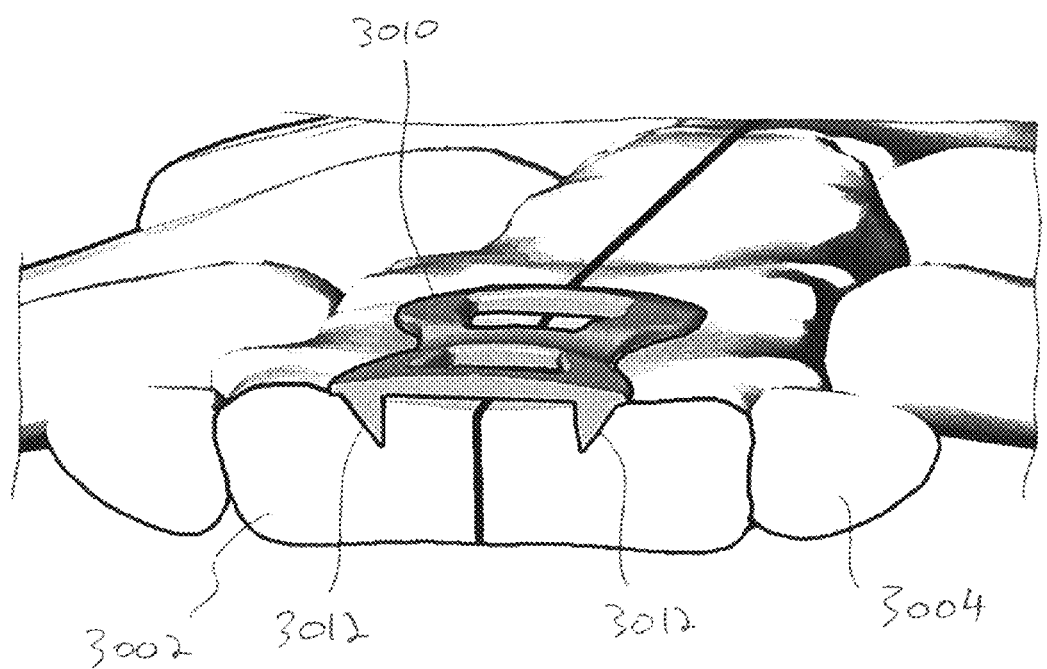
FIG. 71 is a cross-sectional view taken across line 71-71 in FIG. 65 showing the cables removed and the teeth of the plate member engaging the halves of the cut sternum.

The plate 3010 may be positioned adjacent a cut sternum 3006 under surgical sternal cerclage wire or cable 3013. The plate 3010 is sized to fit underneath the wire or cable 3013 and bridge the two halves 3002, 3004 of the cut sternum. The plate is held in position against the cut sternum 3006 by the tensioned wire or cable 3013. In one embodiment, the plate 3010 has a flat portion 3020 and a toothed portion having unidirectional teeth 3012. The unidirectional teeth imbed into a superior or outer surface of the sternum to reinforce the wire or cable 3013 which resists separation of the sternum, as shown in FIGS. 67 and 71.

Figure 68:
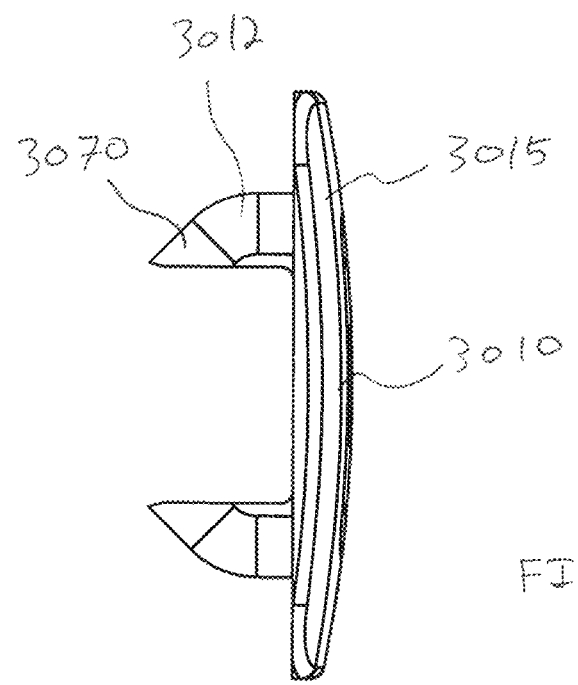
FIG. 68 is an end elevational view of the plate member of FIG. 65 showing the generally flat lower surface and the convex upper surface of the plate member.
Figure 69:
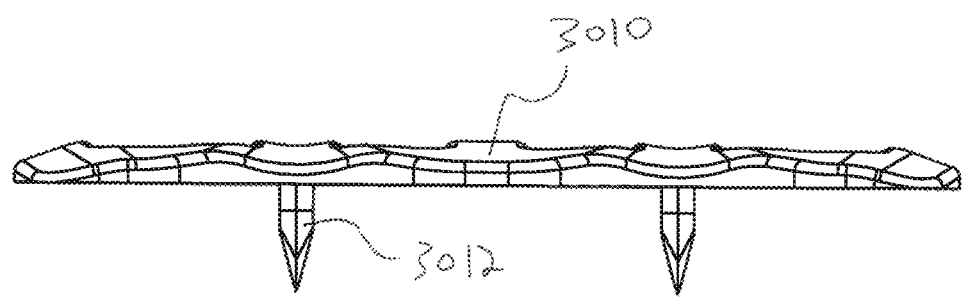
FIG. 69 is a side elevational view of the plate member of FIG. 65 showing teeth extending downward from the lower surface of the plate member.

As shown in FIGS. 68 and 69, the plate 3010 has numerous unidirectional teeth 3012 which allow the sternum halves 3002, 3004 to compress during tensioning of the wires or cables 3013, but resist separation of the sternal halves 3002, 3004 once the wires or cables are fully tensioned. The teeth 3012 are forced into the cortical bone of the superior sternum surface by the force generated by the wires or cables 3013 during tensioning, as shown in FIG. 71.

Figure 70:
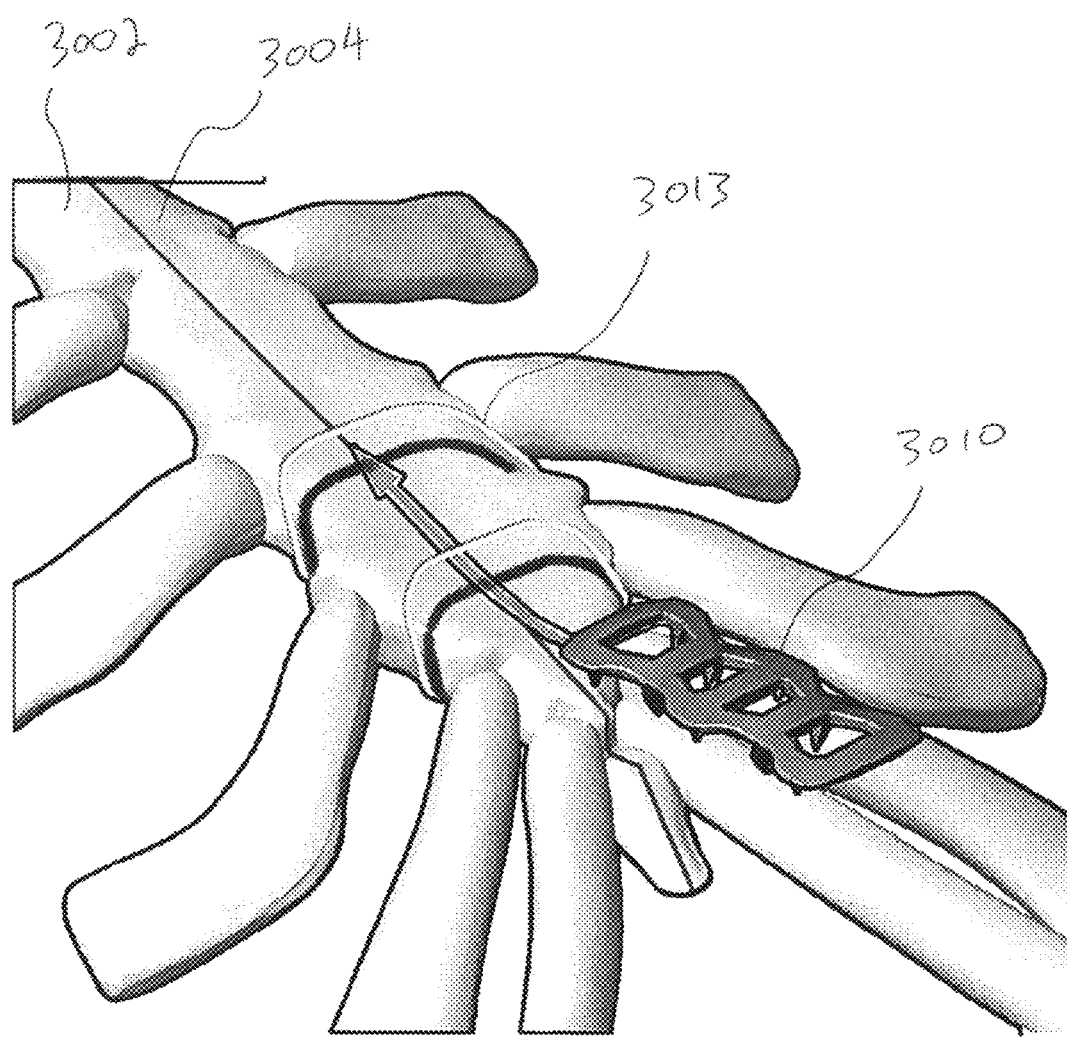
FIG. 70 is a perspective view of the plate member of FIG. 65 being inserted below cables looped around the cut sternum.

The plate 3010 may be inserted manually underneath partially tensioned wire or a figure-eight cable 3013, as shown in FIG. 70. Once the plate 3010 is positioned as desired, the wires or cables 3013 are fully tensioned to lock the entire construct.

Figures 72, 73:
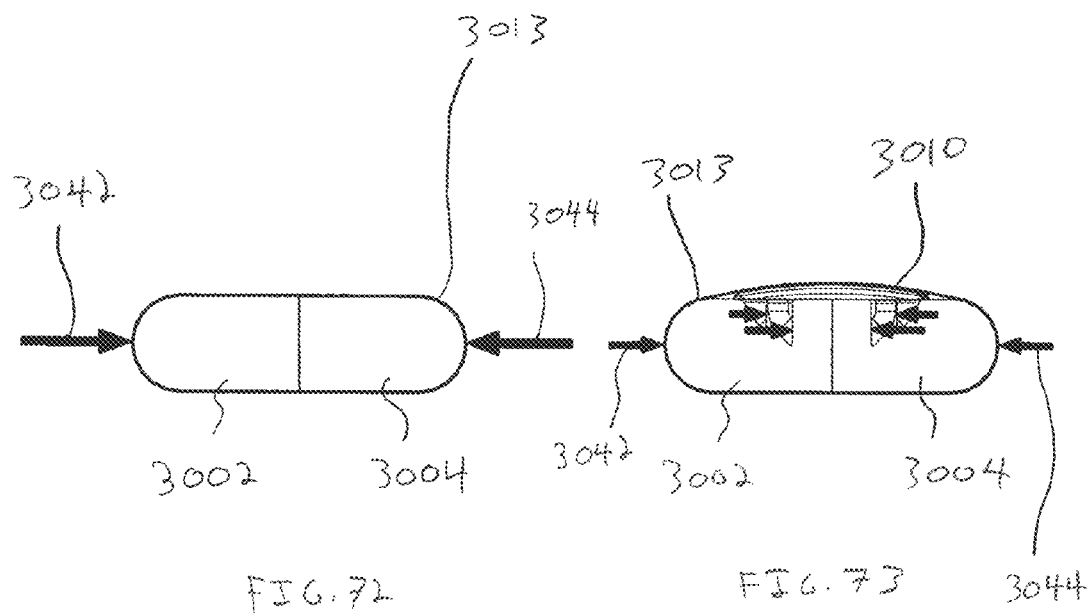
FIG. 72 is a schematic view of the cut sternum showing a force distribution on the halves of the sternum with only the cables present.
FIG. 73 is a schematic view similar to FIG. 72 showing a force distribution on the halves of the sternum with both the plate member and cables present.
Figures 74, 75:
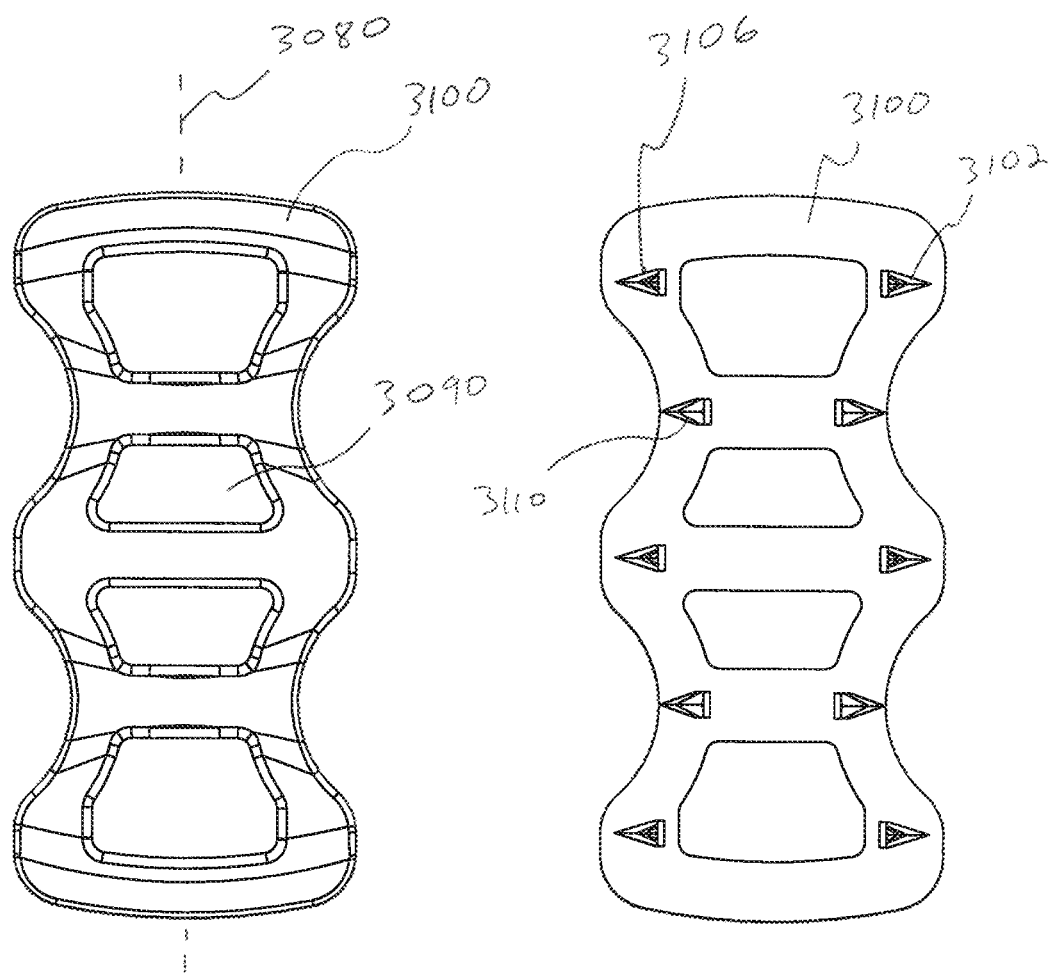
FIG. 74 is a top plan view of another plate member showing a scalloped outer profile of the plate member.
FIG. 75 is a bottom plan view of the plate member of FIG. 74 showing ten teeth disposed along the bottom surface of the plate member.
Figure 76:
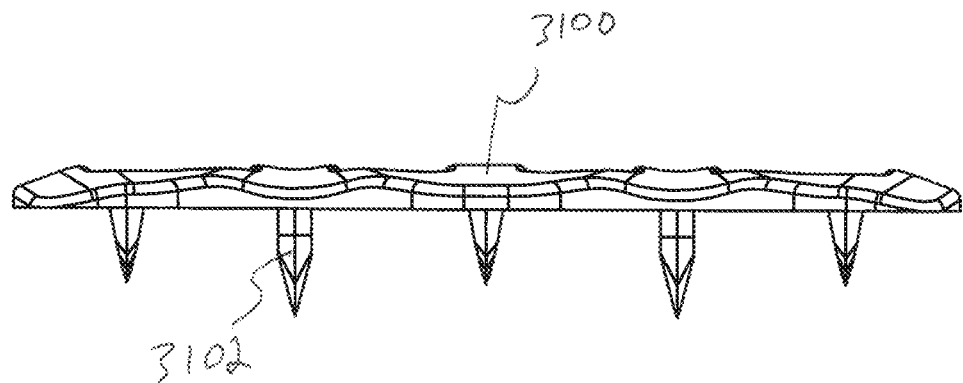
FIG. 76 is a side elevational view of the plate member of FIG. 74 showing the teeth extending downward from the bottom surface of the plate member.
Figure 77:
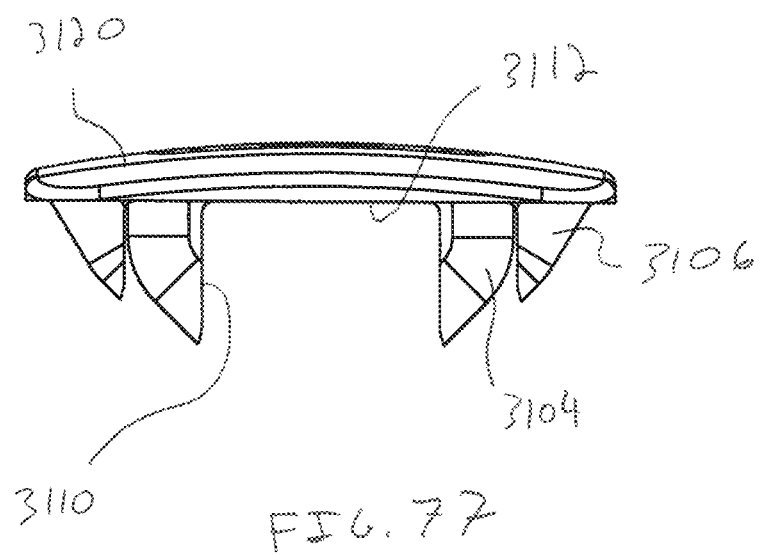
FIG. 77 is an end elevational view of the plate member of FIG. 74 showing the generally flat bottom surface and the convex upper surface of the plate member.
Figure 79:
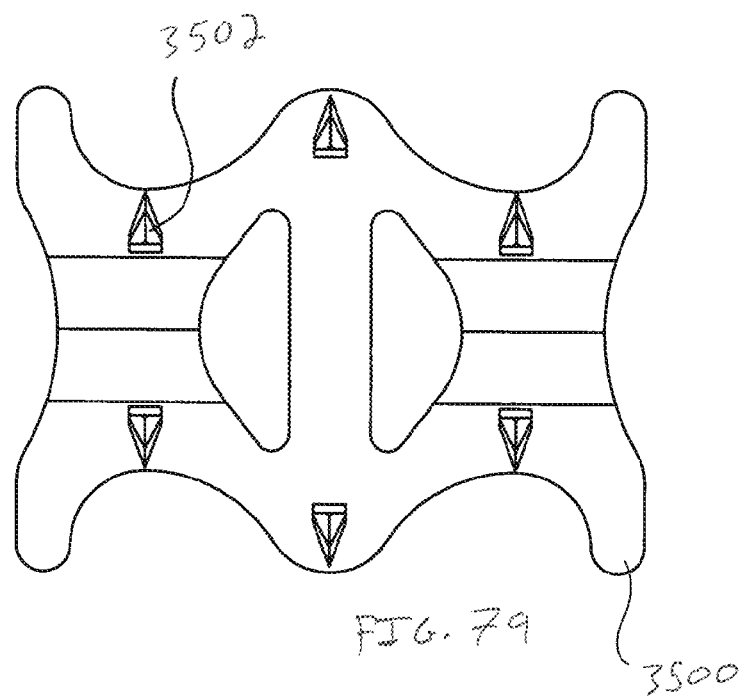
FIG. 79 is a bottom plan view of the plate member of FIG. 79 showing six teeth positioned along a bottom surface of the plate member.
Figure 78:
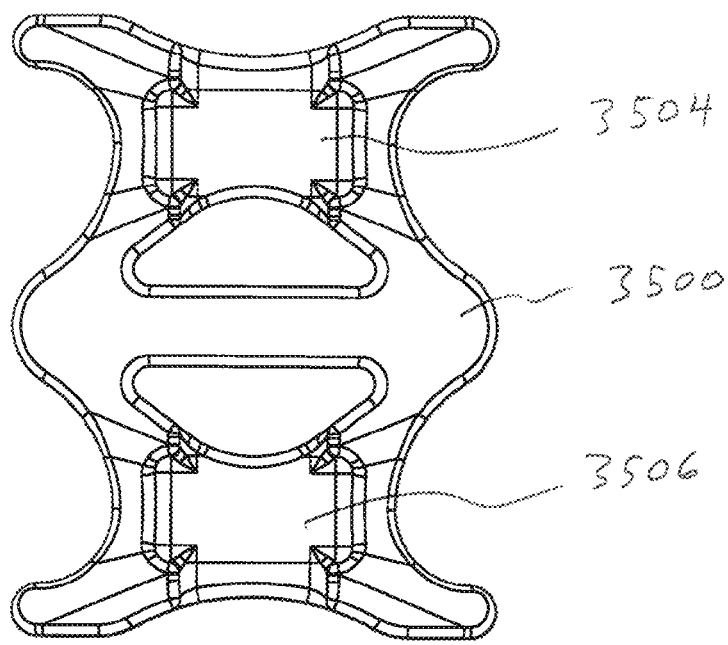
FIG. 78 is a top plan view of another plate member showing a scalloped outer profile of the plate member.

The teeth 3012 of the plate 3010 are designed to pierce the cortical bone and embed themselves fully into the superior surface of the sternum 3006. With the plate 3010 located along the midline bisection of the sternum 3006, it places a series of teeth 3012 on either side of the sternum 3006 which, when fully embedded into the sternum 3006, provide anchor points to transmit forces in tension through the plate 3010 to reinforce the sternum 3006. With reference to FIG. 72, a schematic view of the sternal halves 3002, 3004 is shown with only a wire or cable 3013 securing the halves 3002, 3004 together. Tension in the wire or cable 3013 applies reactive forces 3042, 3044 to resist separation of the sternal halves 3002, 3004. With reference to FIG. 73, a similar schematic view of the sternal halves 3002, 3004 is shown, except that the plate 3010 is secured to the halves 3002, 3004. Engagement of the teeth 3012 with the sternal halves 3002, 3004 resists separation of the halves 3002, 3004, adds to the resistance provided by the wire or cable 3013, and increases the strength of the entire construct.

The plate 3010 is low profile and may have scallops 3060 in its outer profile or surface which provide additional clearance to secure the cable or wire 3013 over the plate 3010 where desired. The scallops 3060 may also provide resistance to movement of the wires or cables along an upper surface 3015 of the plate 3010. More specifically, the wires or cables 3013 may be oriented across the upper surface 3015 so that the wires or cables 3013 extend across the upper surface at a narrow portion 3017 of the scallops 3060 (see FIGS. 65 and 66). Movement of one of the wires or cables 3013 in direction 3019 along the respective scallop 3060 brings the wire or cable 3013 into engagement with a wider portion 3021 which, due to the relatively fixed size of loop of wire or cable 3013, restricts movement of the wire or cable 3013 in direction 3019. Similarly, movement of the one wire or cable 3013 in direction 3023 brings the wire or cable 3013 into engagement with another wider portion 3025 of the scallop 3060, which restricts further movement of the wire or cable 3023 in direction 3025.

The teeth 3012 are designed for minimum penetration forces and have a reverse cut tip 3070 to increase tip strength. The quantity of teeth have two correlated design considerations: more teeth increase push-in forces; fewer teeth decrease pull through effectiveness. In one approach, tooth placement may be optimized by: Two teeth per level being located directly beneath the wire or cable 3013 which transmits tension forces directly into tooth engagement with the sternum 3006. Four teeth 3012 per level are located on either side of the wire or cable 3013 which indirectly transmit tension forces into tooth engagement with the sternum 3006. To reduce the quantity of teeth 3012, the middle teeth (between levels) may be shared. To reduce overall plate insertion forces, the teeth 3012 may be separated into two groups having different lengths, e.g., 1.5 mm difference.

With reference to FIGS. 74-77, a bone plate 3100 is provided having teeth 3102 of varying lengths. The long teeth 3104 (of which there are four on plate 3100) are located directly below the cable/wire and contact the harder cortical bone first and pierce it completely before the remaining shorter teeth 3106 (of which there are six on the illustrated plate) contact the harder cortical bone. This lowers insertion forces when compared to all eight teeth 3102 pushing through the hardest bone at the same time. The tips of all teeth 3102 have a wide 45 degree angle. This angle allows the teeth to slide along the sternal surface until the sternal halves 3002, 3004 are compressed and enough force is applied to embed the teeth 3102. The teeth 3102 have a flat surface 3110 which is perpendicular to an inferior surface 3112 of the plate 3100 to resist the teeth 3102 pulling through the sternal bone once implanted. Having the flat surface 3110 of the teeth 3102 extend perpendicular to the inferior surface 3112 of the plate 3100 may minimize the distance the halves 3002, 3004 of the cut sternum 3006 have to move apart in order to fully seat the teeth 3102. Moving the sternal halves 3002, 3004 apart from each other in order to fully seat the plate 3100 and the teeth thereof compromises compression of the sternal halves 3002, 3004. In some approaches, however, it may be desirable for the surface 3110 of the teeth 3102 to extend obliquely, rather than perpendicular, to the inferior surface 3112 of the plate 3100.

The thickness of the plate 3010 may be kept to a minimum, e.g., 0.08 inches to keep the plate 3010 low profile yet strong and moderately flexible. Tapered transition surfaces extend slightly past the teeth in all directions to allow for a smooth transition to the surface of the sternum without sacrificing tooth strength. The upper or superior surface 3120 of the plate 3010 may be convex to provide a smooth path for the wire or cable without edges that may snag or otherwise interfere with the wire or cable 3013.

The inferior surface 3112 of the plate 3010 may be flat to fit to the average sternal anatomy. The outer profile or upper surface 3120 of the plate 3010 includes scallops 3060 to help nest the wire or cable 3013 in predetermined locations about the plate 3010. This allows for variable spacing between the wire or cable 3013 levels (one size fits all). In one approach, the scallops 3060 permit a surgeon to position a wire or cable 3013 so that the wire or cable 3013 extends across the plate 3010 at a particular angle relative to a longitudinal axis 3080 of the plate 3010 once the wire or cable 3013 has been tightened. The surgeon may select the particular angle that best conforms to the patient's anatomy.

Four windows 3090 are located within the outer perimeter or edge of the plate 3010 and allow for visualization during insertion to achieve proper placement and soft tissue adhesion. The windows 3090 may be designed to maximize window size without sacrificing plate strength.

The plate 3010 may be made of a variety of biocompatible materials including metals, alloys, and plastics. For example, the plate 3010 may be made of polyether ether ketone (PEEK) which offers numerous advantages. Strength of the plate 3010 and teeth 3012 as well as sharpness of teeth 3012 may be improved over other plastics. Other advantages of PEEK include radiolucency, no increase in metallic mass during fluoroscopy/x-rays, bioinert, and PEEK is a good bearing material to minimize wear against the cable/wire. Metallic versions of the plate 3010 may include stainless steel and titanium.

With reference to FIGS. 79-82, a bone plate 3500 is provided that is similar in many aspects to the bone plate 3010 discussed above such that differences between the bone plates 3010, 3500 will be described. The plate 3500 has six teeth 3502 of the same length rather than teeth of varying length to provide a maximum amount of grip while utilizing fewer teeth. The plate 3500 also incorporates two upper recessed portions 3504, 3506 which provide a location for a locking mechanism of the cable or wire 3013 to reduce overall profile, such as cable crimps or wire twists. A ridge 3510 (see FIG. 81) runs beneath the two recessed portions along an lower or inferior surface 3512 of the plate 3500 to increase wall thickness and reduce the profile of the plate 3500 on the sternum 3006 as the plate 3500 will nest into a cut or midline incision 3003 of the sternum 3006 (see FIG. 65).

Those skilled in the art would recognize that a wide variety of modifications, alterations, and combinations can be made with respect to the above described embodiments without departure from the spirit and scope of the invention, in that such modifications, alterations, and combinations, are to be viewed as being within the scope of the invention.

What is claimed is:

1. An apparatus for stabilizing one or more bone portions, the apparatus comprising:
    a bone plate having a lower surface for facing a bone portion and an upper surface;
    a first elongate connector having a length and a bone plate end and a free end that are spaced apart from each other along the length of the first elongate connector, the bone plate end of the first elongate connector being configured to be secured to the bone plate and the free end of the first elongate connector being configured for engaging the bone portion;
    an elongate, flexible portion of the first elongate connector intermediate the bone plate end and the free end of the first elongate connector;
    a second elongate connector independent from the first elongate connector, the second elongate connector having a bone plate end configured for being secured to the bone plate, a free end configured for engaging the bone portion, and a flexible portion intermediate the bone plate end and the free end of the second elongate connector;
    first and second through openings of the bone plate extending through the upper and lower surfaces of the bone plate, the first and second through openings being spaced apart from each other on the bone plate;
    a lock member coupled to the bone plate and extending between the first and second through openings of the bone plate, the lock member having an unlocked configuration that permits the bone plate ends of the first and second elongate connectors to be connected to the lock member and a locked configuration which fixes the bone plate ends of the first and second connectors to the lock member;
    first and second receiving portions of the lock member each disposed in a respective one of the first and second through openings of the bone plate when the lock member is coupled to the bone plate, the first and second receiving portions of the lock member being configured to permit the bone plate end of the first elongate connector to be advanced through the first receiving portion and to permit the bone plate end of the second elongate connector to be advanced through the second receiving portion when the lock member is in the unlocked configuration, the first and second receiving portions being further configured to fix the bone plate end of the first elongate connector in the first receiving portion disposed in the first bone plate through opening and to fix the bone plate end of the second elongate connector in the second receiving portion disposed in the second bone plate through opening when the lock member is in the locked configuration;
    the free end of the first elongate connector being laterally enlarged relative to the flexible portion of the first elongate connector transverse to the length thereof for engaging the bone portion and capturing the bone portion between the bone plate lower surface and the free end of the first elongate connector at opposite sides of the bone portion; and
    the first and second receiving portions of the lock member include deformable material configured to be deformed to fix the receiving portions to the first and second elongate connectors when the first and second elongate connectors extend through first and second through openings of the first and second receiving portions.

2. The apparatus of claim 1, wherein
    at least one of the first and second receiving portions of the lock member is disposed substantially entirely between the upper and lower surfaces of the bone plate.

3. The apparatus of claim 1, wherein the bone plate includes at least one wall extending about the first through opening; and
    the lock member extends into the first through opening from the at least one wall in a direction away therefrom and the first receiving portion of the lock member is spaced from the at least one wall of the first through opening to provide clearance for a tool portion between the first receiving portion and the at least one wall of the through opening.

4. The apparatus of claim 1, wherein one of the first and second receiving portions of the lock member has an enlarged head section and a narrowed neck section adjacent the head section configured to be engaged by a tool and deformed to fix the one of the first and second receiving portions of the lock member to the bone plate end of the associated first or second elongate connector.

5. The apparatus of claim 1, wherein the flexible portion of the first elongate connector includes a cable member.

6. The apparatus of claim 5, wherein the free end of the first elongate connector includes a stop member connected to the cable member.

7. The apparatus of claim 1, wherein the lock member is elongated and has opposite ends that include the first and second receiving portions, the lock member further including a lower surface portion supported by the bone plate, and the first and second receiving portions being completely spaced from the bone plate with the lock in the unlocked and the locked configurations.

8. The apparatus of claim 1, wherein the free end of at least one of the first and second elongate connectors includes a plug having a flange.

9. An apparatus for stabilizing one or more bone portions, the apparatus comprising:
- a pair of independent connectors each including a flexible cable;
- a bone plate having an upper surface and lower surface and a pair of through openings spaced apart from each other on the bone plate and extending through the upper and lower surfaces of the bone plate;
- at least one wall of each of the through openings of the bone plate extending about the corresponding through opening of the bone plate;
- a lock member coupled to the bone plate and extending into each of the through openings of the bone plate, the lock member having an unlocked configuration that permits the flexible cables to be connected to the lock member and a locked configuration that secures the flexible cables to the lock member;
- openings of the lock member being sized to permit the flexible cables to be advanced therethrough when the lock member is in the unlocked configuration and sized to fix the lock member to the flexible cables when the lock member is in the locked configuration;
- a pair of head portions of the lock member that include the openings thereof and are each disposed in a respective one of the through openings of the bone plate completely spaced from the bone plate when the lock member is coupled to the bone plate with the lock member in the unlocked configuration and the locked configuration to provide clearance for a tool between the lock member head portions and the bone plate; and
- the lock member includes deformable material configured to be deformed to reconfigure the lock member from the unlocked configuration to the locked configuration and fix the lock member to the flexible cables when the flexible cables extend through the openings of the head portions.

10. The apparatus of claim 9,
at least one of the head portions of the lock member is disposed entirely between the upper and lower surfaces of the bone plate with the lock member in the unlocked and locked configurations.

11. The apparatus of claim 9, wherein each of the through openings extends through the upper and lower surfaces along a central axis of the through opening; and
the lock member extends into the through openings of the bone plate substantially perpendicular to the central axis central axes of the through openings of the bone plate.

12. The apparatus of claim 9, wherein the lock member includes narrowed neck portions adjacent the head portions configured to be deformed to reconfigure the lock member to the locked configuration.

13. The apparatus of claim 9, wherein at least one of the connectors includes a plug connected to the flexible cable of the connector and the plug includes a flange for engaging a bone portion.

14. The apparatus of claim 9, wherein the bone plate includes a channel and the lock member is received in the channel and extends into the through openings of the bone plate from the channel.

* * * * *